(12) United States Patent
Sorenson et al.

(10) Patent No.: US 10,452,813 B2
(45) Date of Patent: Oct. 22, 2019

(54) MEDICAL IMAGE IDENTIFICATION AND INTERPRETATION

(71) Applicant: TeraRecon, Inc., Foster City, CA (US)

(72) Inventors: Jeffrey L. Sorenson, Wake Forest, NC (US); David W. MacCutcheon, Marshfield, MA (US); Tiecheng Zhao, Concord, CA (US); Gael Kuhn, Montreuil (FR)

(73) Assignee: TeraRecon, Inc., Foster City, CA (US)

( * ) Notice: Subject to any disclaimer, the term of this patent is extended or adjusted under 35 U.S.C. 154(b) by 22 days.

(21) Appl. No.: 15/812,835

(22) Filed: Nov. 14, 2017

(65) Prior Publication Data

US 2018/0137244 A1 May 17, 2018

Related U.S. Application Data

(60) Provisional application No. 62/423,680, filed on Nov. 17, 2016, provisional application No. 62/453,945, filed on Feb. 2, 2017.

(51) Int. Cl.
*G06F 19/00* (2018.01)
*G16H 15/00* (2018.01)
(Continued)

(52) U.S. Cl.
CPC .......... *G06F 19/321* (2013.01); *A61B 8/565* (2013.01); *G16H 15/00* (2018.01); *G16H 30/40* (2018.01);
(Continued)

(58) Field of Classification Search
None
See application file for complete search history.

(56) References Cited

U.S. PATENT DOCUMENTS 6,700,589 B1 * 3/2004 Canelones .......... G06F 16/9577
345/660
6,785,410 B2 8/2004 Vining et al.
(Continued)

OTHER PUBLICATIONS

International Search Report and Written Opinion for PCT/US17/61756, dated Jan. 19, 2018.
(Continued)

*Primary Examiner* — Sultana M Zalalee
(74) *Attorney, Agent, or Firm* — Douglas L. Weller

(57) ABSTRACT

An artificial intelligence findings system includes an artificial intelligence findings system. An image identification engine receives new image data pertaining to a patient and past reports and image data pertaining to the patient. The image identification engine uses the past image data pertaining to the patient to identify for study images of patient anatomical structures, anatomical anomalies and anatomical features within the new image data. A findings engine receives new image data and processes the new image data to generate findings based on the new image data and based on the identified for study images of patient anatomical structures, anatomical anomalies and anatomical features within the new image data. A communication interface provides the findings to a diagnostic review system that presents the findings to a user. An adjustment engine receives notifications of changes to findings made by a user when using the medical image interpretation system.

20 Claims, 25 Drawing Sheets

(51) Int. Cl.
| | |
|---|---|
| *G16H 50/70* | (2018.01) |
| *A61B 8/00* | (2006.01) |
| *G16H 30/40* | (2018.01) |
| *G16H 50/20* | (2018.01) |
| *A61B 5/00* | (2006.01) |
| *G06N 5/02* | (2006.01) |
| *G06T 7/00* | (2017.01) |
| *G06N 5/04* | (2006.01) |
| *A61B 5/055* | (2006.01) |

(52) U.S. Cl.
CPC ............ *G16H 50/20* (2018.01); *G16H 50/70* (2018.01); *A61B 5/0013* (2013.01); *A61B 5/055* (2013.01); *A61B 2576/00* (2013.01); *G06N 5/022* (2013.01); *G06N 5/045* (2013.01); *G06T 7/0012* (2013.01); *G06T 2207/10116* (2013.01)

(56) References Cited

U.S. PATENT DOCUMENTS

| | | | |
|---|---|---|---|
| 8,145,503 B2 | 3/2012 | Backhaus et al. | |
| 8,331,637 B2 | 12/2012 | Bar-Aviv et al. | |
| 8,370,293 B2 | 2/2013 | Iwase et al. | |
| 2004/0196905 A1* | 10/2004 | Yamane | H04N 19/89 375/240.12 |
| 2006/0061595 A1* | 3/2006 | Goede | G06F 17/241 345/619 |
| 2006/0074633 A1 | 4/2006 | Mahesh et al. | |
| 2007/0127790 A1 | 6/2007 | Lau et al. | |
| 2007/0127795 A1* | 6/2007 | Lau | G06F 19/321 382/128 |
| 2008/0118130 A1* | 5/2008 | Pillai | G16H 10/60 382/131 |
| 2008/0133596 A1* | 6/2008 | Chang | G06F 19/321 |
| 2009/0063932 A1* | 3/2009 | Ishii | H04L 1/0086 714/758 |
| 2009/0103789 A1* | 4/2009 | Danner | G06F 19/321 382/128 |
| 2010/0049740 A1* | 2/2010 | Iwase | G06F 19/321 705/7.27 |
| 2010/0080427 A1* | 4/2010 | Yeluri | G06F 19/321 382/128 |
| 2011/0028825 A1 | 2/2011 | Dougas et al. | |
| 2011/0238618 A1* | 9/2011 | Valdiserri | G16H 40/63 707/608 |
| 2014/0324469 A1 | 10/2014 | Reiner | |
| 2015/0127379 A1* | 5/2015 | Sorenson | G06Q 50/24 705/3 |
| 2015/0200945 A1* | 7/2015 | Edson | G06F 16/00 726/28 |
| 2015/0331995 A1 | 11/2015 | Zhao et al. | |
| 2016/0092446 A1 | 3/2016 | Nye | |
| 2016/0314784 A1* | 10/2016 | Kleppe | A61B 5/167 |
| 2016/0350919 A1 | 12/2016 | Steigauf et al. | |
| 2016/0364862 A1* | 12/2016 | Reicher | G06F 19/00 |
| 2017/0076046 A1 | 3/2017 | Barnes et al. | |
| 2017/0337329 A1 | 11/2017 | Liu et al. | |
| 2018/0144244 A1 | 3/2018 | Masoud et al. | |
| 2018/0101645 A1* | 4/2018 | Sorenson | G06T 7/11 |

OTHER PUBLICATIONS

PowerScribe 360 Reporting, The leading radiology reporting platform; https://www.nuance.com/healthcare/medical-imaging/powerscribe-360-reporting.html; Downloaded Oct. 10, 2017.

mPower | Nuance: Measure performance. Demonstrate value.; https://www.nuance.com/healthcare/medical-imaging/mpower-clinical-analytics.html; Downloaded Oct. 10, 2017.

RADLogics Virtual Resident: We Help Radiologists Stay Firmly in Control; http://radlogics.com/#solution; Downloaded Oct. 10, 2017.

M*Modal: Market-leading solutions for efficient creation of high quality documentation with real-time intelligence and workflow management; https://mmodal.com/imaging-solutions/#; Downloaded Oct. 10, 2017.

Watson Health Imaging Discover new approaches to medical imaging; https://www.ibm.com/watson/health/imaging/; Downloaded Oct. 10, 2017.

Galileo: Clinical Decision Support. Speed Up Your Radiology Workflow; http://galileocds.com/machine-learning-radiology/; Downloaded Oct. 10, 2017.

Tianyi Wang, et al. "Intelligent Tools for a Productive Radiologist Workflow: How Machine Learning Enriches Hanging Protocols", 2013, availalbe from GE Healthcare, a division of General Electric Company.

vRad and MetaMind Collaborate on Deep Learning Powered WorkDows to Help Radiologists Accelerate Identification of Life-threatening Abnormalities; Image Technology News; Jun. 18, 2015.

* cited by examiner

| label | modality | body section | anatomy | orientation | sort type | contrast enhanced | study description | series description |
|---|---|---|---|---|---|---|---|---|
| tva | mr | chest | heart | short_axis | 4d | no | mri cardiac w/ cont w/flow quant-ross | sax-sorted |
| flow | mr | chest | heart | na | 2.5d | no | mri cardiac w/ cont w/flow quant-ross | float-quant_bh_ao |
| flow | mr | chest | heart | na | 4d | no | mri cardiac w/ cont w/flow quant-ross | float-quant_bh_ao_p |
| de | mr | chest | heart | short_axis | 3d | no | mri cardiac w/ cont w/flow quant-ross | dme_psir_single-short_mag |
| de | mr | chest | heart | short_axis | 4d | no | mri cardiac w/ cont w/flow quant-ross | dme_psir_single-short_psir |
| tva | mr | chest | heart | short_axis | 4d | no | cardiac^phi cardiac main | phase sort s7-17 |
| flow | mr | chest | heart | na | 2.5d | no | cardiac^phi cardiac main | fl3_retro_v150_bpc_bh_pa |
| flow | mr | chest | heart | na | 2.5d | no | cardiac^phi cardiac main | fl3_retro_v150_bpc_bh_pa_m |
| flow | mr | chest | heart | na | 2.5d | no | cardiac^phi cardiac main | fl3_retro_v150_bpc_bh_pa_p |
| de | mr | chest | heart | short_axis | 3d | no | cardiac^phi cardiac main | ss psir 300 ti default_mag |
| de | mr | chest | heart | short_axis | 3d | no | cardiac^phi cardiac main | ss psir 300 ti default_psir |
| | | | | | | | scmr_cardiac_b17_espree_18_z^arrhythmogen | |
| tva | mr | chest | heart | short_axis | 4d | no | ic_rv_cardiomypathy | phase sort s 10-21 |
| | | | | | | | scmr_cardiac_b17_espree_18_z^arrhythmogen | |
| flow | mr | chest | heart | na | 2.5d | no | ic_rv_cardiomypathy | flow pqa |

FIG. 19

| | Modality | |
|---|---|---|
| CT Modality | Angiography | MRI |
| CT 1 | Angio 1 | MRI 1 |
| CT Head | | |
| CT Back | | |

| | Body Part | |
|---|---|---|
| Head | Back | Unknown |
| CT Head | CT Back | MRI 1 |
| | | CT 1 |
| | | Angio 1 |

FIG. 27

MEDICAL IMAGE IDENTIFICATION AND INTERPRETATION

RELATED APPLICATIONS

This application claims the benefit of U.S. Provisional Application No. 62/423,680 filed Nov. 17, 2016 and U.S. Provisional Application No. 62/453,945 filed Feb. 2, 2017. The disclosures of the above applications are incorporated by reference herein in their entirety.

FIELD OF THE INVENTION

Embodiments of the present invention relate generally to medical information processing systems. More particularly, embodiments of the invention relate to medical image interpretation using artificial intelligence, iterative image processing engine training and a bidirectional interaction between an image processing engine results and a physician.

BACKGROUND

Today, in medical image reviewing processes, physicians often review a partially pre-completed report prepared for a physician's review. The pre-completed report includes, for example, patient history, medical findings, and medical images. The medical images may be pre-processed to generate the findings automatically or semi-automatically to include, for example, a set of two-dimensional or three-dimensional, or time-resolved four-dimensional findings, which can include lines, regions of interest, overlays, fused image, volumetric contours and other features extracted computational methods for extracting information, anatomic areas, pathology, physiologic indications, time-resolved findings and other advanced image processing techniques, or combinations thereof, from the images based on attributes found within the image data by the image processing engines. A current image data set can be compared with other similar previously diagnosed patient files to suggest possible findings, similarities or irregularities found in the latest study, in the serial set of current studies or in comparing and analyzing previous related images studies, or in comparing the new study to old studies. In addition to clinical findings and measurements, new images may be derived from the processing of the original images, or image overlays, or segmented anatomic regions as well as analytical values describing the features identified. In addition to being viewed in the clinical reporting system, these items are viewed on medical image viewers, Picture Archiving and Communication Systems (PACS) systems and Electronic Health Record (EHR) systems.

BRIEF DESCRIPTION OF THE DRAWINGS

Embodiments are illustrated by way of example and not limitation in the figures of the accompanying drawings in which like references indicate similar elements.

FIG. 19 illustrates a DICOM Header table.

FIG. 25, FIG. 26, FIG. 27 and FIG. 28 are graphical user interfaces (GUI) illustrating a workflow.

DETAILED DESCRIPTION

Figure 1:
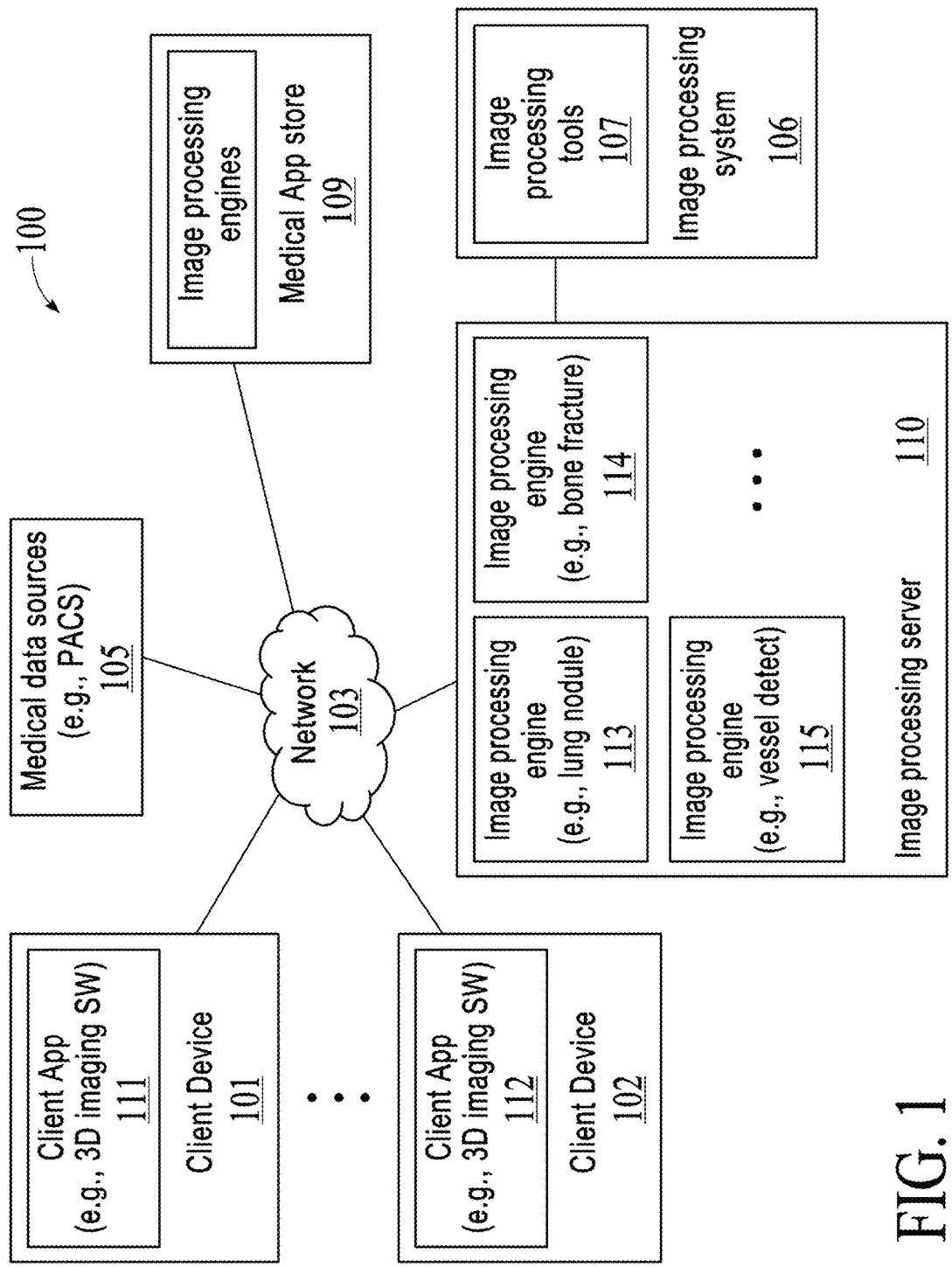
FIG. 1 is a block diagram illustrating a medical data review system according to one embodiment.

Various embodiments and aspects will be described with reference to details discussed below, and the accompanying drawings will illustrate the various embodiments. The following description and drawings are illustrative and are not to be construed as limiting. Numerous specific details are described to provide a thorough understanding of various embodiments of the present invention. However, in certain instances, well-known or conventional details are not described in order to provide a concise discussion of embodiments of the present inventions.

Reference in the specification to "one embodiment" or "an embodiment" means that a particular feature, structure, or characteristic described in conjunction with the embodiment can be included in at least one embodiment. The appearances of the phrase "in one embodiment" in various places in the specification do not necessarily all refer to the same embodiment.

According to one aspect, a locally-sited system and/or cloud-based platform is utilized to make it easy to anonymize studies, upload studies, register and access a new account, establish a community, specify a clinical advisory board and/or governance for the group, access tools to train and create machine learned algorithms/engines, upload or download algorithms/engines, access and run published algorithms/engines on studies and communicate the outcome/results such as number of uses, accuracy, and confidence level based on the confirmed or rejected findings. The system can have a framework for determining interpretation workflow best practices which incorporate machine learned algorithms, which is configurable based on an individual's beliefs or a group's beliefs, along with big data analyses to determine similarities and crowd-sourced common practices between them. Algorithms which are configurable based on an individual's beliefs or a group's beliefs can be shared to one or more medical institutions.

The system can be a local cloud system for one medical institute at one or more locations. The cloud-based system can be a private cloud for one medical institute at one or more geographic locations. The system can be a system that can connect one or more medical institutes at one or more locations. The cloud-based system can be a public cloud. There can be a main cloud system that can connect multiple local cloud systems. For example, there can be a main cloud system that can connect multiple private cloud systems from multiple institutes. The degree of access of information and tools from the main cloud system to the private cloud systems can depend on preconfigured settings by the medical institutes.

The image processing engines can work independently or in combination with one another when evoked or enabled on a multi-sided platform which utilizes machine learning, deep learning and deterministic statistical methods (engines) running on medical image data, medical metadata and other patient and procedure related content to achieve improved cohorts of images and information that have a higher or lower pre-test probability or confidence of having a specific targeted finding confirmed by the physician or clinician. The target findings are either held in blind confidence to see if the physician agrees independently, or the findings are presented within the physician interpretation process to evoke responses, and any feedback, adjustments, agreement or disagreement are captured and utilized as performance feedback for the engines which created the suggestions.

Findings represent any anatomy of interest, measurements, indications, reference materials which may relate, prior studies similar to this study, suggestion of tools, and almost any then-current information or automations tools that are desired to be used in a diagnostic or research interpretation process. The engines are interchangeable in the medical data review system. As such, the types of findings and functions of the engines will vary and change over time. The performance feedback received from both engines processing data and medical data review system utilization data is captured in the form of statistical interactions data, and is utilized to determine the relative value of the current image data cohort which was processed and reviewed, as well as the value and accuracy of any tool(s), automated interactions, findings and other data intentionally evoked in the process of preparing the studies or displaying the study for physician or clinician review, and/or the value of the engine(s) themselves as well as various combinations thereof.

As such, every intentional or incidental presentation of images, data and findings can be measured for physician agreement, adjustment or disagreement, in either a blinded or unblinded manner, and this generates valuable data allowing any or all of the following: a) engines to be improved when new feedback is returned to allow for higher confirmation rates and reduction of missed findings by physicians, b) workflow to be improved by measuring reviewer performance and adapting review tools and image/content display to reduce effort and access to the commonly required items within the medical image (or other) viewer c) physician quality to be measured when curated image cohorts with known findings are sent (or injected) for medical data review and blinded findings are compared to the actual known findings in the cohort, and d) prospective application of the medical data review system to pre-process studies which have not been read, allowing real-time physician first-time interpretations of medical image studies to prospectively incorporate parallel blinded or unblinded automatically generated medical data review system findings and e) assembly of a machine and human readable database(s) of such images, data, interactions, and findings which is/are up d iteratively or continuously to provide the ability to assess trends and/or to have supervised or unsupervised engines analyze this data continuously or iteratively in order to optimize the engine(s) that are used to create the next image cohort, tools and layout selection/suggestions, optional engine availability and other features and data necessary for medical data review and diagnostic interpretation of this cohort (engines of engines).

One embodiment allows for an unsupervised (or supervised) engine of engines (also referred to as a master engine, a supervisor engine, or a managing engine) to run autonomously and select the engines (e.g., secondary engines or slave engines) that run and the number of image studies or patient content sets that run per engine, for example concurrently (e.g., via multiple threads) in a distributed manner. To achieve an autonomous capability, the medical data review system administrator is required to provide the engine of engines limitations on the number of studies or content sets that it places in a cohort, or that it sends for medical data review, each limited by time period or by a limit of uses of an engine or engines in any cohort, limitations or targets for the type and quantity of findings, specifications regarding the group(s) of cohorts, or time period(s).

The unsupervised engine of engines is provided individual and/or collective limitations (minimum, maximum, mean, or other statistically relevant or set limits/targets) on the types and/or number/amount of images, image cohorts, content, findings, interactions and processing time to run these engines and/or for physicians to perform these processes in order to force the engine of engines to optimize its work and not consume too much of the physicians' time for medical data review and also not to consume too much computational resources, both of which have significant costs. To ensure alignment of the observations and selections of the unsupervised engine with maximized clinical value of the findings, annotation adjustments, assembly of image cohorts and physician/clinician feedback received in medical data review and clinical diagnostic interpretation, weighted values (equal or unequal) are placed upon one or more of the a) engines, b) the quantity and type of findings made by each engine (including no findings) c) multipliers applied to the cases where findings are confirmed or rejected by multiple engines, and d) multipliers applied to the cases where multiple engines worked on an image or content set to determine a finding (or non-finding).

Engines may be developed by the same or different individuals or companies that developed the medical data review system, with the engines utilizing commonalities in their input and output schemas to allow multiple engines to be run in serial or hierarchical fashion, also known as an ensemble engine. These ensemble engines can be assembled programmatically, using a supervised engine of engines, or an unsupervised engine of engines with values placed on the outputs or the running of engines or finding of findings. A pre-defined input and output schema for communications by and between engines and the medical data review system, or between engines and other engines, allows for abstraction of inputs and outputs into various forms as required by various engines. For example, if Engine 1 accepts data point coordinates with zero as the middle value of an infinite positive and negative range domain and Engine 2 accepts these with 0 being the lowest value in an infinite always positive range domain, then the abstraction occurring in the communication schema would be to map the range values of these two domains over a specified range of possible shared values. The implementation of the abstraction method to implement the operation of containerized engines and engines of engines, works across all possible value types and ranges.

Findings can include but are not limited to derived images, contours, segmentations, overlays, numbers, similarities, quantities and any other values commonly viewed, measured, derived or found in enterprise electronic health records systems, picture archiving and communications systems, content management systems, medical data review systems, laboratory systems and/or advanced visualization systems. Differences between the medical data review generated results and the physician or clinician generated results can be captured, compared and output by the medical data review system for future analyses and optimization of engines.

As a multi-tenancy platform, the medical data review system can be accessed by various stakeholders such as engine authors and end-users (healthcare providers with physicians and clinicians, researchers, industry entities, or groups of these). Access control to certain images, image cohorts, end-user physicians or clinician feedback, governance, engines for upload or deletion, engines for running images and clinical content, and user settings are able to be controlled to prevent comingling of images, engines or use without permission from its authorized owner(s). Any stakeholder can be an engine author which can create an algorithm which can be used by an end user, without the end user having access to the algorithm, code, or image data. This can be done by sending the studies to a private or multi-tenant secure server, which can be cloud based or locally sited to process the study with any number of containerized engines/algorithms. The access control allows algorithm developers to grant authentication and administration privileges.

On embodiment of algorithm and use authentication gives algorithm developers the ability to grant different end users the ability to use an algorithm, or allowing them to be published for use publicly while requiring the end user(s) to agree to platform and licensing agreements provided in written form or via click-through legal terms and conditions. While administrative privileges gives an algorithm developer the ability to have other algorithm developers modify the algorithm or create a new version of the algorithm, or engines or engines of engines to modify the algorithm. Version control allows algorithm developers the ability to create different generations of their algorithm, while tracking changes to the algorithms technical file for regulatory clearance. Similarly, different generations of image and clinical content cohorts and medical data review feedback data are also versioned and secured to protect the intrinsic value and avoid unintended proliferation of data.

In one embodiment, image processing engines (also referred to as image processing modules or image processing units, which may also process or only process data relating to or unrelated to any images) can be developed by a variety of developers which may be operated by a variety of organizations or enterprise entities. An image processing engine refers to an executable image or binary code that can be individually and independently launched and executed by a processor, in some cases, in combination of hardware processing resources (e.g., graphic acceleration devices such as graphic processing units or GPUs), to perform a specific image process on an image (such as shape recognition, size measurement, etc.). The image processing engines can be uploaded and listed in a Web server to allow a user to select and program the intended operation parameters and/or download one or more image processing engines to run in a specific location independently as an insular locally-sited medical data review system solution, and/or in communication and combination with another system (in hybrid mode). The selected image processing engines can be configured to a variety of configurations (e.g., in series, in parallel, or both) to perform a sequence of one or more image processing operations.

According to another aspect, image processing engines can be utilized to inject studies into other commercial or independently-developed medical data review systems which are designed to review the medical findings identified by a set of physicians. In one embodiment, the image processing engines are used to confirm or verify findings by the physicians, where the engines operate as medical data review systems. The image processing engines can also be utilized to screen and identify any images that are more likely to have abnormal findings and send those for medical data review on a third-party system, or evoke diagnostic review on the medical data review system.

The identified images are then reviewed by a set of physicians to verify and confirm the findings. In the latter case, the engines operate as preliminary reviewers. As a result, for thousands of medical images that need to be reviewed, the image processing engines can perform massive image processing operations to preliminary identify the abnormal images, and the engines can prospectively "learn" from the feedback when these images are reviewed by the physicians to during diagnostic interpretation. If the findings of the image processing engines and the reviewing physicians are consistent, the operations of the image processing engines involved can be validated, i.e., the algorithms used by the image processing engines are validated. Otherwise, such algorithms may need further fine tune or training, for example, using machine learning methods. Sometimes the function of an engine is called an algorithm. When a physician or engine performs an action, or applies an algorithm/input or tool, this is sometimes referred to as an operation. These operations result in findings, which are a part of the overall interpretation outcome of a medical data review study. Similar to medical data review workflow but involving engines, in the medical data review system, there is a first result (from a physician, engine, engine of engines, or operation), this is compared to a second result (from a physician, engine, engine of engines, or operation) and in the case of disagreement, these are adjudicated by a third result (from a physician, engine, engine of engines, or operation). As such, in the medical data review system, the enabling technology expands the roles and applications of medical data review in novel ways by performing operations either for the interpreting physician, before the physician, or after the physician, and using this interaction to support the comparison of human and machine (engine) found findings and providing a technology platform and method for human input, engines, content and findings to be captured, collated and combined in a real-time image interpretation environment, in addition to typical medical data review environments. In the case of the medical data review system, this includes interaction (synchronously or asynchronously) between any combination of physicians, engines (or engines of engines), content/image cohorts and 3$^{rd}$ party validated data sources.

The physician confirmations and rejections as well as other collectable workflow inputs they provide using the medical data review system can be used as training data in a closed-loop fashion whereby the engine becomes continuously or iteratively trained using machine learning techniques in a supervised or unsupervised fashion, If there is any inconsistency between the engine findings and the physician findings (including physician adjustments, confirmation, or rejections), a message is sent to the database recording the event, and optionally, a message can be sent to any predetermined device(s), individual(s) or groups even during the primary interpretation process or medical data review system process indicating that something needs to be paid attention. This may occur in an unsupervised fashion with engines providing feedback to other engines, still creating a closed loop learning scenario. In such cases, the first, second and even third result may be provided from engines (or engines of engines) and not humans, and used for the purpose of enhancing the engine(s) used by the medical data review system. When the first, second and third result are derived entirely from humans, this is typical medical data review and is not a part of the medical data review system. However, in such case, the image and content cohorts of these interpretations with the validated findings can be captured as an image/content cohort. Such cohorts can be used by engines retrospectively to learn, and these data can be injected into the medical data review process by the medical data review system to further verify the performance of physicians, further improve the image/content cohort, and to develop new engines and/or engines of engines.

Engines (and engines of engines) must perform well on live streams of incoming clinical data and not just the image/content cohorts. These real-time clinical images and content sets that need interpretation are often imperfect. This can occur because there are patient scanning defects such as scanning protocol errors, patient movement, metal artifacts, obese patients, etc. It may also happen due to a lack of availability of prior imaging studies that are related to the current one, or missing clinical information or medical errors, etc. For these reasons, real-time study evaluation is more challenging than processing image/content cohorts and various engines/operations can be expected to fail. The medical data review system can utilize cohorts of challenged or failed studies to determine the likelihood of any given ensemble, engine or operation succeeding given the use case and quality factors of the data presented. It can utilize this information in an engine of engines that analyzes data and influences which engines, ensembles and operations are run, to best deliver the required/desired findings for any particular study or even a challenging cohort of images. By optimizing this way, the medical data review system reduces wasted compute power, reduces wasted physician time reviewing inferior findings, and increases the consistency and performance of engines and ensembles, thereby utilizing the intelligence of the medical data review system to improve the performance of the medical data review system itself.

Alerts can be provided if there are consistent, inconsistent, normal, abnormal, high quality, low quality, failed, or successful results returned by one or many engines or ensembles. Additionally, a supervised or unsupervised machine learned engine can be used to monitor and learn the effectiveness of various engines in various situations and begin to optimize the use of various engines to be best applied to various use cases in order to increase the number of findings which need to be confirmed by a physician or that are likely to otherwise be missed by a physician if not marked or otherwise measured, mentioned, indicated or marked by the engine and supplied by the cloud platform, whether inside the Medical data review process or inside another physician or clinician image interpretation or review process, or within an electronic health record, viewing system, PACS or 3D advanced visualization system.

According to one embodiment, when a first set of medical images associated with a particular clinical study is received from a medical data source, one or more image processing engines are invoked to process (e.g., recognizing shapes, features, trends in the images or other data or measurements) the medical images (or data, used synonymously in this application) according to a predetermined or machine learned suggested order for performing the engine operations that is configured for the particular type of imaging study. The image processing engines are configured to perform image processing operations to detect any abnormal findings of the medical images, or to optimize clinical workflow in accordance with the preferences or computer-observed working ways of the end-user (based on the system that they are using for interpretation, or in an end-user customized manner as part of the medical data review system functionality) and to generate a first result describing the abnormal findings or preferred presentation of the images and normal and/or abnormal findings. The physician input represents the second result. The medical data review system detects agreement or disagreement in the results and findings and sends alerts for further adjudication given the discordant results, or it records the differences and provides these to the owner of the algorithm/engine allowing them to govern whether this feedback is accepted (i.e. whether or not the physician input should be accepted as truth, and whether this study should be included in a new or updated cohort.)

One embodiment regulates inferencing and image cohort collection based on image acquisition quality. Image quality needs to be checked and verified before or after any predictive engine is evoked in order to ensure engine standards are met. This may include the standards of regulatory and oversight bodies responsible for quality control in imaging informatics. One example of this pertains to pulmonary embolism studies. Sensitivity and specificity for detection of a pulmonary embolism is directly related to image acquisition quality. Artifacts that result in image degradation such as respiratory motion artifact or technical acquisition parameters (e.g. contrast bolus timing) directly impact the ability of an engine to confidently identify a given finding. For a pulmonary embolism detection engine result to be presented to the physician or verified, a quality control engine must assess contrast bolus timing and for respiratory motion artifact in order to modify the confidence of the pulmonary embolism detection engine. There may be engines that perform better or worse given the presence or absence of a given artifact which can be automatically selected to process the images. The combination of engines processed ensures the optimal and appropriate confidence of the finding output for a given finding. The presence or absence of a finding may therefore result as a range or function of the study quality and not necessarily a discrete value. This is one embodiment of the engine of engine selector with respect to quality control and handling of image artifacts and technical image acquisition quality variations.

A similar quality control paradigm applies to image cohort curation quality scoring. For each image stored in a given image cohort that is curated by a combination of physicians and engines, quality scores with the presence and absence of imaging artifacts are stored in a database along with findings. The automated quality control score can be accepted or rejected by a diagnostic image interpreter or provider. Both high and low quality label sets are curated. A given engine's performance is scored against both high and low quality data sets to determine if an engine can be used if certain artifacts are present.

Specifically, in one embodiment, the image processing engines are provided by one or more image processing engine developers which may be operated by the same or different entities or organizations. A second set of medical images is transmitted to a first review system, wherein the second set of medical images is a subset of the first set of the medical images. In one embodiment, the second set of medical images have been categorized by the image processing engines as abnormal images. The review system operating as a medical data review system is configured to review the second set of medical images to verify or confirm or unverify or reject the abnormality of the images, generating a second result. In response to the second result received from the review system, the operations of the image processing engines run on the medical data review system are validated or invalidated based on the first result and the second result (this is done on the $3^{rd}$ party conventional medical data review system or on the medical data review system described herein, which has such capability.

Machine learned engines may learn from this information and/or the governance and/or owner of the algorithm may accept or reject such feedback into the learning process, or an unsupervised engine may experiment with various scenarios on its own to find a statistically ideal combination of accepting some feedback and rejecting other feedback. Engine(s)/ensemble(s) performance can be verified against a reference standard image cohort that is not available to an engine author as training data in order to perform quality control, wherein versioning of an engine displays these performance metrics and/or versions a given algorithm and the cohorts of images provided to an author for traceability in accordance with typical healthcare regulatory and reference standards. The injected images or image cohorts specially assembled for algorithm verification and engine qualification are randomized in terms of the number and types of images provided to prevent overfitting of a given version of the algorithm (i.e. adjusting the data to make the algorithm look good or rate well). Such versioning ensures a defined separation between training data and validation data, in the case where it is not appropriate to perform validation using a reference standard cohort.

In one embodiment, by validating an image processing engine's results consistently and by many users, the image processing engine may become a "certified" or "approved" image processing engine by utilizing these data to support regulatory certifications, by an outside third party entity such as the FDA, or similar. If an image processing engine cannot be validated based on its results of use, the parameters or algorithm of the image processing engine may need to be adjusted or retrained, for example, using a machine-learning method based on these prior results (image cohorts and clinical content cohorts). Further, the revisioning of engines, image cohorts, clinical cohorts and the saving of all medical data review system utilization data provides a method for engines of engines to learn and adapt, and for engine authors to improve the performance of their engines based upon these recorded events.

According to some embodiments, a machine learned workflow system can receive image data. The machine learned workflow system can review the image data and propose one or more clinical protocols or one or more workflows. The proposed clinical protocols or workflows for each image data can be determined based on in-image analysis and/or metadata of the image data. The machine learned workflow system can allow the user to replace, remove, or add clinical protocols or workflows. The machine learned workflow system can track the user interactions. The machine learned workflow system can machine learn based on user interactions such that the next time a similar image data is received, the machine learned workflow system can propose optimized clinical protocols and workflows.

FIG. 1 is a block diagram illustrating a medical data medical data review system according to one embodiment. Referring to FIG. 1, medical data review system 100 includes one or more client devices 101-102 communicatively coupled to medical image processing server 110 over network 103. Client devices 101-102 can be a desktop, laptop, mobile device, workstation, etc. Network 103 may be a local area network (LAN), a metropolitan area network (MAN), a wide area network (WAN) such as the Internet or an intranet, a private cloud network, a public cloud network, or a combination thereof.

Image processing server 110 hosts a number of image processing engines 113-115 that can be invoked and configured to perform a series of one or more image processing operations or clinical content processing operations on medical images and clinical content, which may be provided by medical data sources 105. Medical data sources 105 can include Laboratory Information System (LIS), Radiology Information System (RIS), Enterprise Content Management Systems (ECM), Electronic Medical Record (EMR), Hospital Information System (HIS), Picture Archiving and Communication System (PACS), VNA (Vendor Neutral Archive), Advanced Visualization 3D systems, EMR data, various directories as well as other data sources such as HIE (health information exchange) servers and individual or organizational repositories. Medical data sources 105 may be managed and/or operated by different organizations or information providers than the organization which operates image processing server 110. Medical image data source 105 can include image data from cloud based storage, local drive, CD, hard drive, DVD, USB, web uploader, any DICOM repository or source, other sources of images and clinical content, or any combination thereof. Image processing server 110 can receive image data (e.g., studies, clinical reports, images, patient data, utilization data, or any combination thereof) over a network from the medical image data sources 105. For example, the image data includes security information to allow restriction of use. This can be accomplished, for example, by including within the security information including watermarks, embedded metadata with or without an underlying certificate or verification system.

The medical data review system recognizes the intrinsic value of labelled data, which requires human intelligence and verification, or the intentional collection of large amounts of unlabeled data. As an option to prevent reverse engineering of engines by way of labelled data theft, or to prevent duplicating a labelled data set by stealing an engine that can perform this task, the medical data review system includes a watermarking, image labelling and/or encryption capability with or without an underlying certificate or verification system, which can be utilized to prevent access, running, decrypting or export of labeled data, source data, or restrict engines/ensembles from running in the absence or presence of such marking without engine author permission.

One embodiment of the medical data review system can protect the authors of an engine's intellectual property by preventing the reverse engineering of an engine by collecting annotated data without permission of an author. This may vary based on EULA and permissions set by the author and end user. Several sample implementations of this feature include but is not limited to a) tracking of studies by annotating metadata or image data using a block chain based (e.g. etherum) DApp (decentralized application) b) watermarking image overlays generated by engines c) encrypting the output of an engine to be viewed with an authenticated viewer or PACS environment d) preventing bulk data export of annotated image data and or metadata e) logging use of annotated image cohorts, f) preventing the running of an engine/ensemble without the receipt of a verification certificate, and g) preventing an engine from running on data unless it contains specific markings or annotated metadata, or an encrypted access key, etc.

In one embodiment, the medical data provided by data sources 105 may include medical image data in a DICOM format, medical image data in a non-DICOM format, scheduling data, registration data, demographic data, prescription data, billing data, insurance data, dictation data, report data, workflow data, EKG data, best practices reference materials, reference materials, training materials, etc. These data may reside in several locations or systems including HIS, RIS, PACS, LIS, ECM, EMR or other systems. The non-DICOM data may be in several formats including A/V, MPEG, WAV, JPG, PDF, Microsoft Office™ formats and other formats. Generally, data in a PACS will include DICOM data, where data in the HIS, MS and LIS, ECM, EMR will include non-DICOM data, including both image and non-image data. HIE data includes data available via a health information exchange system. These data generally include data available across different organizations within a region, community or hospital system, and may be text-based, file-based, DICOM or non-DICOM image data. Other data may include any other relevant data, including data in directories on computers, databases, white papers and clinical repositories, research institutions and data collected from users, mobile devices, and in the course of clinical use, etc.

Image processing engines 113-115 can be developed and provided by a variety of vendors, which may be operated by a variety of organization or enterprise entities. One embodiment is an image processing engine as an executable image, container, virtual environment or binary code that can be individually and independently launched and executed by a processor, in some cases, in combination of hardware processing resources (e.g., graphic acceleration devices such as graphic processing units or GPUs), to perform a specific image process on an image (or data set, used synonymously), such as trends, comparisons, specific values, characteristics, shape or likeness (similarity) recognition, areas of interest, size, measurements, etc. The image processing engines 113-115 can be uploaded and listed in a Web server 109, in this example, an application store, to allow a user of clients 101-102 to purchase, select, and download one or more image processing engines as part of client applications 111-112 respectively. The selected image processing engines can be configured to a variety of configurations (e.g., in series, in parallel, or both) to perform a sequence of one or more image processing operations. The image processing engines 113-115 can be downloaded to client systems 101-102 to perform the operations. Alternatively, the image processing engines 113-115 can be hosted in a cloud-based system, such as an image processing server 110 as a part of software as a service (SaaS) and/or platform as a service (PaaS), to perform the operations and allow authors of engines to control access and maintain versions and regulatory compliance.

In one embodiment, each of image processing engines or modules 113-115 may be configured to perform a specific image processing operation on medical images, such as, for example, lung nodule detection, bone fracture detection, organ identification and segmentation, blood clot detection, image body part categorization, chronic obstructive pulmonary disease (COPD) detection, or soft tissue characterization. An image processing engine can perform such a detection based on the shape, texture, sphericity measurement, color, or other features obtained from the medical images or which are derived or implied by the clinical content. In one embodiment, multiple image processing engines provided by multiple vendors can be configured in series, in parallel, or a combination of both to perform image processing operations, which may be configured via a configuration interface of medical image processing server 110 or through client applications 111-112.

In one embodiment, when any one of image processing engines 113-115 is invoked, it may further invoke one or more image processing tools 107 of image processing system 106, which may be integrated as a part of image processing server 110 or alternatively, as a remote medical image processing system (or a cluster of systems or servers) communicatively coupled to image processing server 110. Image processing system 106 may be implemented as part of a TeraRecon® AquariusNET™ server and/or a TeraRecon® AquariusAPS™ server. Each image processing engine may invoke medical image processing system 106 to perform an image processing operation on an image of a body part of the patient which was navigated to or may be automatically detected by an engine or engine of engines, to produce certain image quantitative data or measurement data on such images. Similarly, clinical content may be investigated.

The image quantitative data may be used to manually or semi-automatically determine or measure the size and/or characteristics of a particular body part of the medical image. The image quantitative data may be compared with a corresponding benchmark associated with the type of the image to determine whether a particular medical condition, medical issue, or disease is present or suspected. The likelihood of such occurrence may further be predicted or determined based on a trend of same type of medical data of the patient as part of medical history of the patient and/or other patients' data. In one embodiment, Ensemble engines may be combined, for example, one which finds the body part, another that segments it, another that labels the anatomy within it, and another that detects signs of leading diseases in that area, and finally another that can match these findings with clinical information resources and recommendations to provide assistance and direction to the physician.

In one embodiment, a processing engine may be associated with a particular body part of a patient. Only certain engines will apply according to what part of the body it is pertaining to, or according to what imaging modality type (the imaging procedure type) that is used. This will help the engine of engines mentioned above make a good choice and learn what works.

Image processing server 110 can further include one or more e-suites (i.e., e-suites, also referred to as ensembles, can be a combination of one or more image processing engines). As such, ensembles can be cascaded for increasing granularity, thereby increasing sensitivity and specificity for the particular intended action of the ensemble engine.

The engine or e-suites can detect findings (e.g., a disease, an indication, a feature, an object, a shape, a texture, a measurement, insurance fraud, or any combination thereof). The one or more engines and/or one or more e-suites can detect findings from studies (e.g., clinical reports, images, patient data, image data, metadata, or any combination thereof) based on metadata, known methods of in-image analysis, or any combination thereof. The image processing engines 113-115 of image processing server 110 can flag image data with findings, for example, indicating that the image data is abnormal.

Flagging can include displaying the actual finding(s), or derived summary indication utilizing a combination of findings, found by the engine/e-suite, the engine/e-suite name, a simple mark representing that the study was processed by image processing server 110, marking that the study was normal/abnormal, a series of macro level indication choices (e.g., red, yellow, green, or orange) depicting the risk of the findings, marking with severity (e.g., mild, moderate, or severe) or icons denoting a finding (e.g., a simple mark denoting that there is a findings), relevant tools automatically evoked in the image viewing system, or any combination thereof, or otherwise, as provided by the engine/e-suite/ensemble or engine of engines.

Flagging can occur on the study or separately from the study. Flagging may be available and accessible through one or several Representational State Transfer (restful) services, API's, notification systems or pushed to a third-party application or on image processing server, or the database(s) of the medical data review system. In one embodiment, flagging can be displayed or viewed in a 3D medical imaging software application (e.g., client applications 111-112). The engines and/or the e-suites can machine learn or be trained using machine tearing algorithms based on prior findings periodically such that as the engines/e-suites process more studies, the engines/e-suites can detect findings more accurately. In other words, the confidence level of detecting findings increases as more studies are processed. Based on the findings of the engines and/or e-suites, image processing server 110 can prioritize and sort study worklist based on, for example, type of findings, severity of findings, risk to patient health, or any combination thereof. This is the final output of the platform including a list of results and macro findings that can be used in the process of primary image interpretation, and any of these findings can be opened or further interrogated in terms of the underlying assumptions for adjustment or the quality of the image data or clinical data can be assessed for appropriateness and possible exchange or editing.

An interface with restful services, or an API, provides bidirectional communication between the medical data review system, other common medical data review systems, and other medical image viewers, such that any feedback provided in these $3^{rd}$ part applications can be returned to the medical data review system to facilitate engine learning and the curation of additional image data cohorts and clinical content cohorts.

The application store 109 may be an e-commerce server that can store one or more engines, one or more e-suites, or any combination thereof. Image processing server 110 can store the same or different engines or e-suites as the application store 109. The engines or e-suites of image processing server 110 can process studies depending on which engines are selected by the user via a graphical user interface (GUI) or website (local or on the internet) of image processing server 110. Image processing server 110 can send updated/improved engines or e-suites to the application store 109. The application store 109 or image processing server 110 can store user profiles and/or group profiles. The user profiles can be specific to one or more users. The group profiles can be specific for one or more groups, for example, a governance board, a radiologist group, a cardiologist group, a technician group, a developer group, or any combination thereof. The user profiles and the group profiles can have access controls to tools, engines, e-suites, training tools, coding tools, or any combination thereof. Users and/or groups can expand or reduce access control to other users and/or groups.

Tools, engines, e-suites, training tools, coding tools, or any combination thereof can be displayed and used via image processing server 110 or in a 2D and/or 3D medical imaging software application, or medical data review system, or the novel medical data review system. A medical imaging software application is a client application that accesses the output of the image processing tools 107 of image processing system 106. For example, a first user can upload a first engine via the client device (e.g., a website, mobile phone, a workstation, a computer, an iPad, a laptop, or any other method or type, or combination thereof) that can be stored in the application store 109. The first user or a governance board can provide access to certain tools, for example machine learning/training tools, to a second user or group. The second user or group can use the machine learning/training tools and the feedback from this usage can be applied to train the first engine to detect findings with higher accuracy. The first engine can be updated by image processing server 110 and stored in the application store 109. The processing of image data by engines and updating of the engines can occur at image processing server 110, the image processing application store 109, or any combination thereof.

Note that these engines can have measured performance attributes that are either prescriptive, implemented through supervised learning, or allowed to be self-developed by the engines (engines of engines) through either supervised or unsupervised learning. Then, through governance, the person uploading the engine can either accept or reject the changes and/or publish them for use by others, or not.

Image processing server 110 can be implemented by engines or e-suites from one or more medical institutes at different locations, one or more users, one or more groups, or any combination thereof. Image processing server 110 can have a graphical user interface (GUI) such that one or more users can upload or download one or more engines or one or more e-suites. Image processing server 110 can have a GUI for one or more users or groups to train, code, develop, upload, delete, track, purchase, update, or process data on engines or e-suites. Image processing server 110 can have access controls. Image processing server 110 can be password protected to support a multi-tenant environment which provides independent security and cloud access controls to support controlled access to engines, ensemble engines, engines of engines and the configuration thereof. These passwords (and or authentication methods for integrated workflow with other systems) support separate access control of image cohorts, clinical data cohorts, engine accessibility and the interaction database.

Image processing server 110 can allow users or groups to give access control to tools and engines to other users or groups from the same medical institute or other medical institutes (e.g., multi-tenancy configuration). This can promote collaborative efforts among one or more users or groups from one or more medical institutes to improve engines or e-suites to detect findings. Image processing server 110 can have a GUI that can allow the users to run engines or e-suites to process image data. In one embodiment, the output of the medical data review system can be integrated and/or consumed by any third-party system that supports the restful and or API communications or is capable of read/write to the database of the platform. Alternatively, the viewing portion of the medical data review system may be the consumer of this content and/or be embedded into the third-party system or used as stand-alone. Any image processing engines 113-115 can further invoke image processing tools 107 of image processing system 106, depending upon the settings for security and governance which are applied by the engine owners and the medical data review system users performing medical data review and/or diagnostic interpretation.

An engine author can upload any image processing engine or e-suite through image processing server 110 to the application store 109 using its graphical interface such as web interface. Image processing server 110 can have a developer platform for one or more engine developers to update, change, train, machine-learn, or any combination thereof any of the engines on image processing server 110. The engines can be improved to detect the findings on a developer platform, for example, via training using machine-learning algorithms or via modifying a containerized version of a predict method for a given engine. One way this approach can be accomplished is by aggregating data to improve a given engine and versioning the data used for iterative training assessment and the versioning of engine source code within a given software container or wrapper asynchronously, allowing distribution and updating of algorithms in use either in the cloud or which are in use remotely in a deployed containerized algorithm player software that is administered and governed by the actions of the end-users and algorithm/engine authors collaborating and working in the platform.

One or more individual processing engines can be wrapped in a software container with a defined set of inputs and outputs. Processing engines having compatible inputs and outputs can be executed serially or in parallel (e.g., via multiple threads) to create a more accurate final output. In one embodiment, a standardized restful web services API (or similar) may be utilized that allows the abstraction of the needed inputs and outputs of a specific engine/algorithm to the standard published schema as supported and updated by the platform. This requires every engine to have an abstraction layer on the input and output side that allows the mapping and abstraction. Then one or more abstracted outputs can be mapped to one or abstracted inputs.

For example, an engine developer can train a lung nodule detection engine to detect lung nodules in studies on the developer platform of the application store 109 or a data analytic system (not shown) by training the engine based on various features of detecting lung nodules (e.g., geometric shapes, textures, other combination of features resulting in detection of lung nodules, or any combination thereof). In another example, the engine developer can train a blood clot engine on the developer platform. In another example, a bone fracture engine can machine-learn on the developer platform based on bone fracture engine data from image processing server 110. In another example, a COPD engine can machine learn based on the same COPD engine data, based on another COPD engine data, or any combination thereof.

Figure 2:
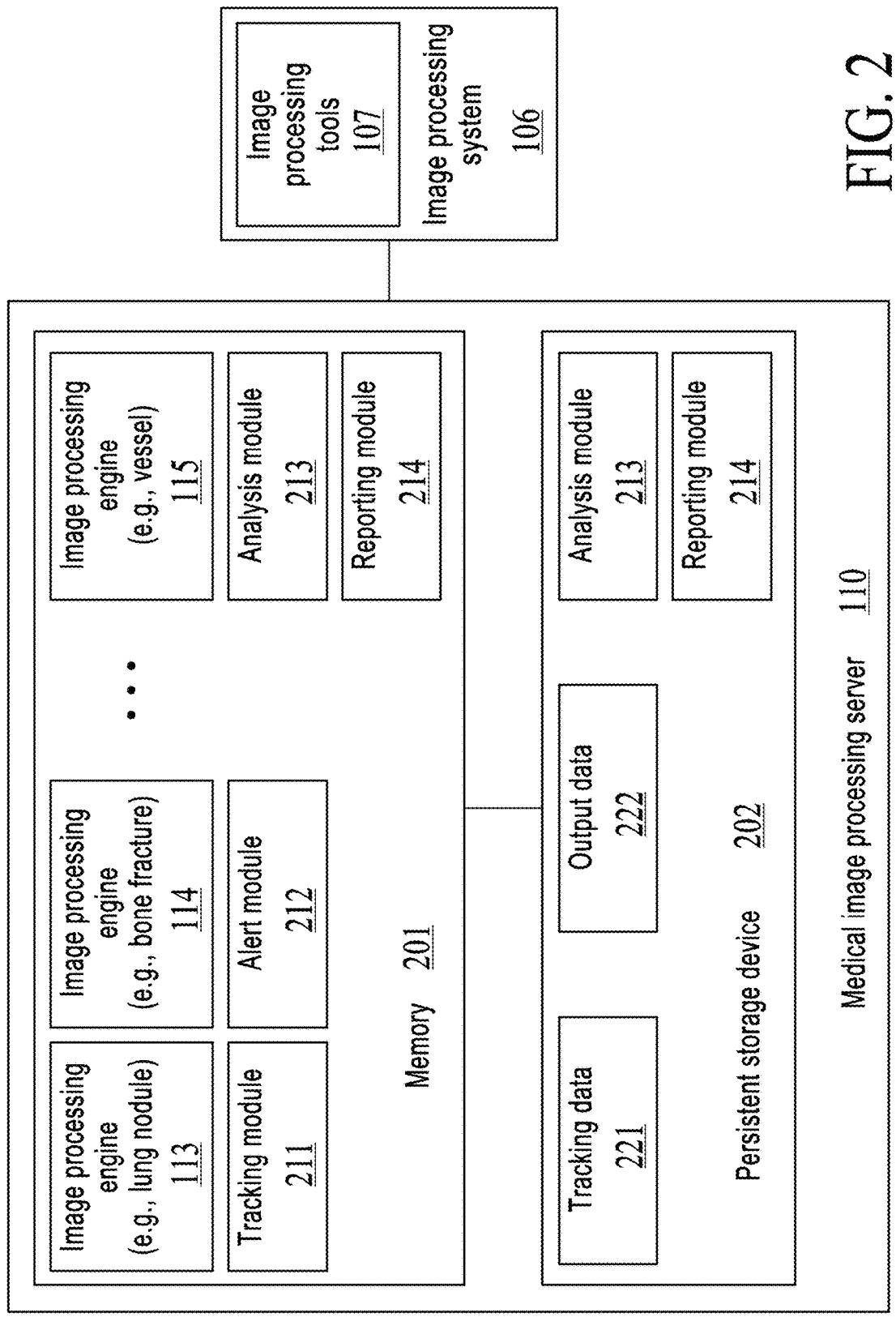
FIG. 2 is a block diagram illustrating an example of an image processing server according to one embodiment.

FIG. 2 is a block diagram illustrating an example of an image processing server according to one embodiment. Referring to FIG. 2, image processing server 110 includes memory 201 (e.g., dynamic random access memory or DRAM) hosting one or more image processing engines 113-115, which may be installed in and loaded from persistent storage device 202 (e.g., hard disks), and executed by one or more processors (not shown). Image processing server 110 further includes tracking module 211, alert module 212, analysis module 213, and reporting module 214. Image processing engines 113-115 can be configured in a variety of configurations according to process configuration 224. Process configuration 224 may be stored in a configuration file that is specifically configured by a user or for a particular study or images. Medical image processing server 110 may be multi-tenancy cloud server. There may be multiple configuration files, each may be associated with a user or a group of users, which may be configured via a configuration interface (not shown).

Figure 3:
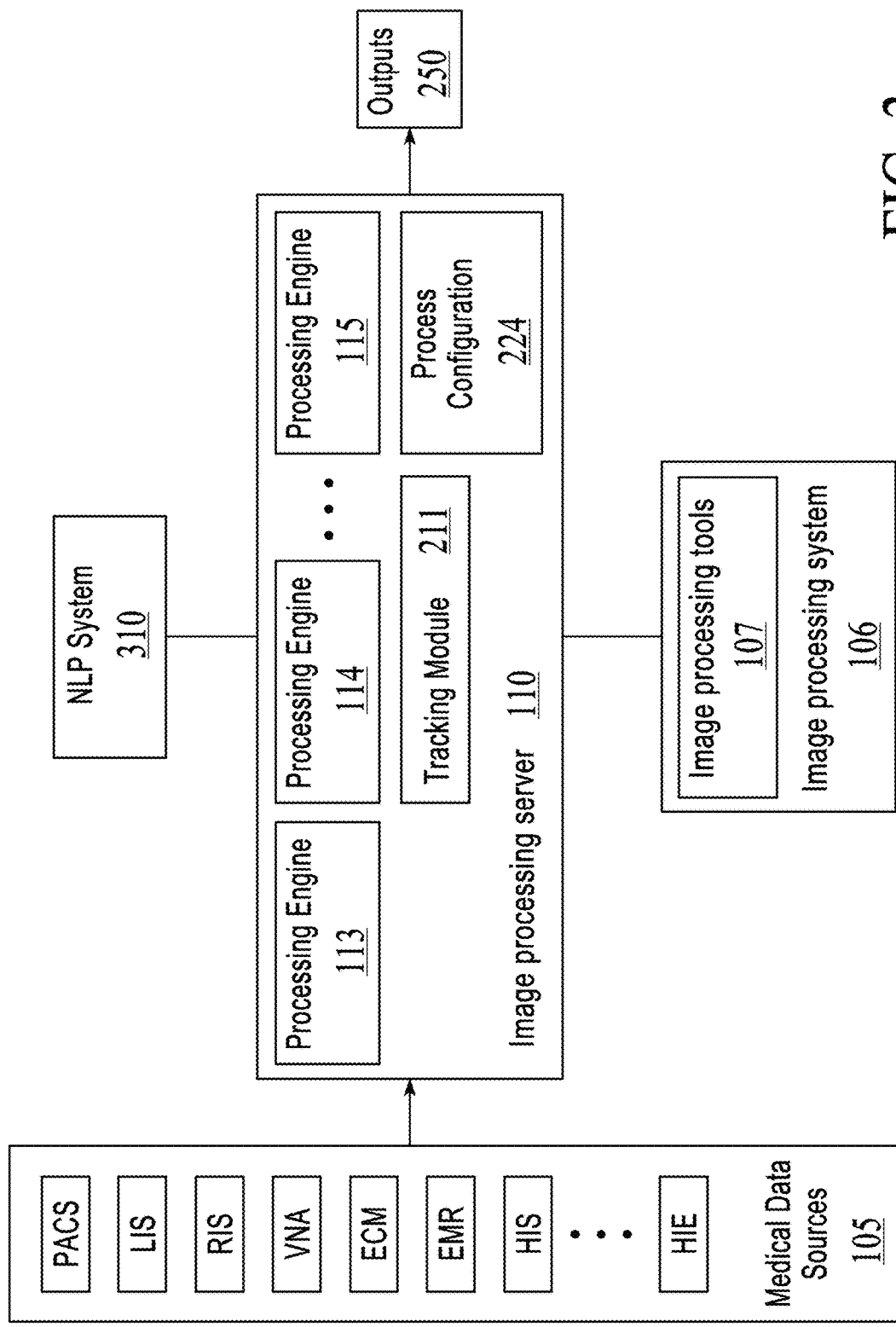
FIG. 3 is a flow diagram illustrating a processing flow of medical image processing according to one embodiment.
Figure 4A:
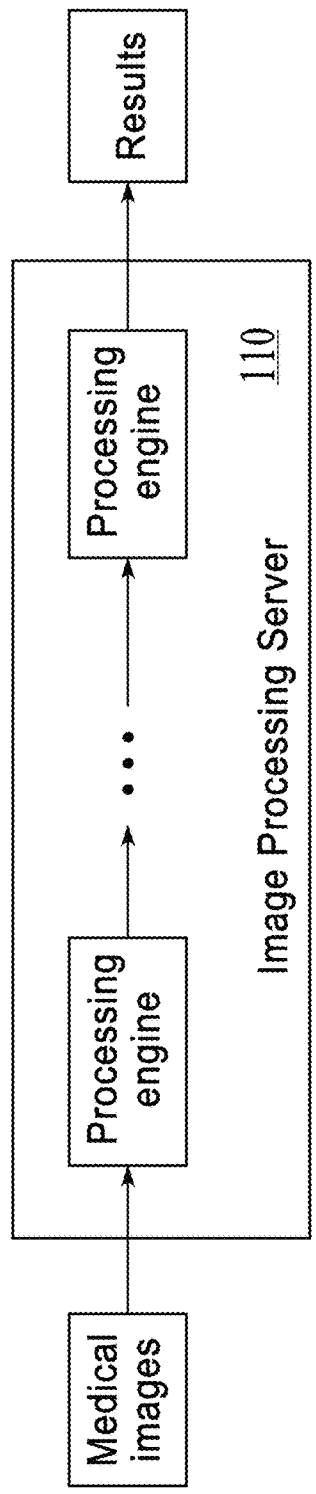
FIG. 4A, FIG. 4B and FIG. 4C are block diagrams illustrating examples of configurations of image processing engines according to certain embodiments.
Figure 4B:
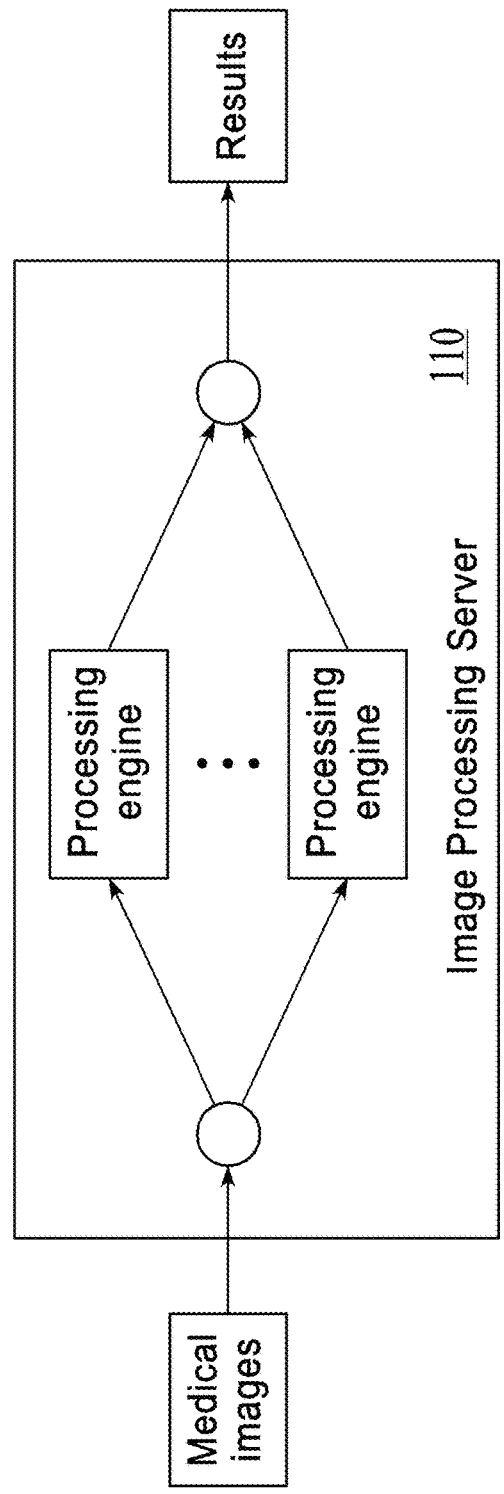
Figure 4C:
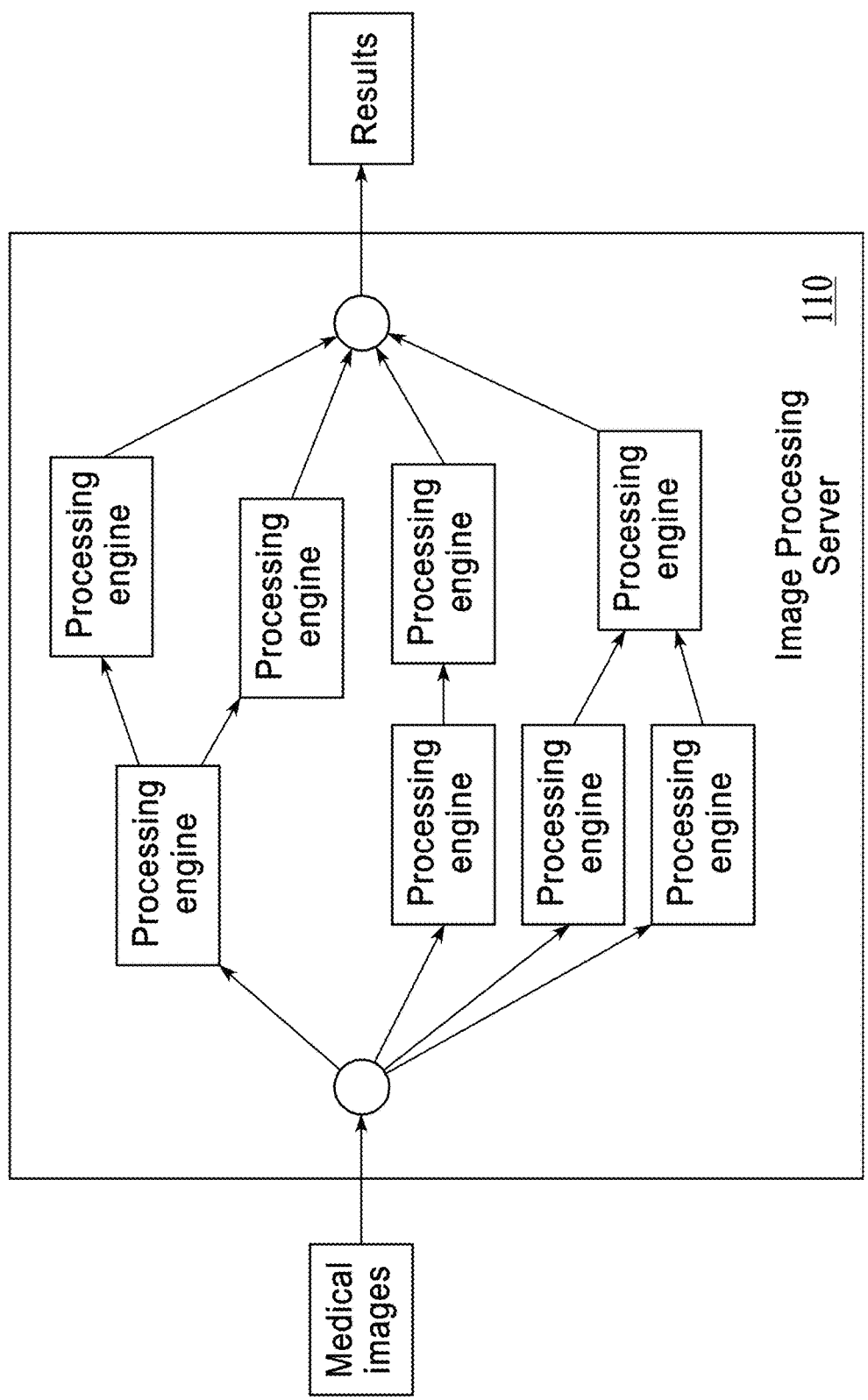

For example, referring to FIGS. 2 and 3, medical data (in this example, medical images) can be received from medical data source 105 at image processing server 110. One or more of image processing engines 113-115 can be arranged according to a sequential order based on process configuration data 224. The image processing engines 113-115 may further invoke image processing tools 107 of medical image processing system 106. One or more results 250 may be generated and stored in persistent storage device 224 as a part of output data 222. In one embodiment, image processing engines 113-115 can be arranged in series, in which an output of a first image processing engine can be utilized as an input of a second image processing engine, as shown in FIG. 4A. Alternatively, image processing engines 113-115 can be arranged in parallel to perform the same or different image processing operations concurrently as shown in FIG. 4B. The outputs of the image processing engines are then aggregated to generate a final result. Furthermore, image processing engines 113-115 can be arranged in both series and parallel as shown in FIG. 4C.

In one embodiment, image processing server 110 may further invoke a natural language processing (NLP) system 310 to process the texts or languages of outputs 250. NLP system 310 is able to scan, analyze, and match features extracted by image processing server 110 to identify studies with missed findings or misinterpreted findings to correlates with outputs 250. NLP is a field of computer science, artificial intelligence and linguistics concerned with the interactions between computers and human (natural) languages, and, in particular, concerned with programming computers to fruitfully process large natural language corpora. Many different classes of machine learning algorithms have been applied to NLP tasks. These algorithms take as input a large set of "features" that are generated from the input data.

For example, a first engine can run an algorithm to detect findings. The first engine can create an output of the findings of the first engine. The findings by the first engine can be included in the statistical interface, a report (not shown), in a diagnostic interpretation viewer (not shown, or any system or database capable of accessing results and cohorts through the restful services and/or API. A physician can review the output of the findings. The physician can validate/invalidate the findings of the first engine. The validation/invalidation of the findings of the first engine can be included as part of output data 222. The first engine can process studies from one or more medical institutes where the results can be included output data 222.

Any stakeholder can be an engine author which can create an algorithm which can be used by an end user, without the end user having access to the algorithm, code, or image data required to train the algorithm. This is done by sending the studies to a private or multi-tenant secure server, which can be cloud based or locally sited to process the study with any number of containerized engines/algorithms. The access control allows algorithm developers to grant authentication and administration privileges. On embodiment of algorithm and use authentication gives algorithm developers the ability to grant different end users the ability to use an algorithm, or allowing them to be published for use publicly while requiring the end user(s) to agree to platform and licensing agreements provided in written form or via click-through legal terms and conditions. While administrative privileges gives an algorithm developer the ability to have other algorithm developers modify the algorithm or create a new version of the algorithm, or engines or engines of engines to modify the algorithm. Version control allows algorithm developers the ability to create different generations of their algorithm, while tracking changes to the algorithms technical file for regulatory clearance. Similarly, different generations of image and clinical content cohorts and medical data review feedback data are also versioned and secured to protect the intrinsic value and avoid unintended proliferation of data.

In one embodiment, a post contrast CT scan of the abdomen is processed prior to a CT fluoroscopy procedure. The post contrast images are registered to a CT fluoroscopy data set using a registration engine. The results of the registration and anatomic segmentation can be toggled over the CT fluoroscopic data in order to display blood vessels on a non-contrast CT fluoroscopic image during a CT guided biopsy or ablation. Thus, resulting in virtual contrast enhanced fluoroscopic results. This may be supported similarly with other modalities, such as MRI. In one embodiment, the validation or invalidation of the output of findings of the e-suite can be included in tracking data 221 and/or statistics 223.

According to another scenario, for example, a PACS server or CT, MRI, ultrasound, X-ray, or other imaging modality or information system can send studies to a first engine of the e-suite. After the first engine processes the studies, the output of findings from the first engine can be sent to a second engine and a third engine. The second engine and the third engine can run in parallel. The output of findings of the second engine and the third engine can be combined. The combined output of the second engine and the third engine can become the output of findings of the e-suite. Alternatively, the process may begin with multiple engines receiving the data for processing and these send their results to one or more other engines as described. The final output can be sent back to the source modality, or a PACS, or the medical data review system to be reviewed by a physician to confirm or deny the findings of the output of the e-suite ensemble.

The output of the first engine can have a first weight factor. The output of the second engine can have a second weight factor, etc. The first weight factor and the second weight factor can be any percent ranging from −100%% to +100%, or a logarithmic scale, or any author-assigned scale of any kind that is appropriate for the type of test and cohorts being run. The weighted output of findings can enable one engine to have more weight than another engine, and one type of finding in an engine can have different weightings for each finding. The user can manipulate the weights of each engine from an interface on image processing server 110.

Alternatively, the engine of engines can be applied to set these values using supervised or unsupervised machine learning techniques.

For example, the first engine can be an engine for edge detection. The second engine can be an engine for soft tissue detection. A user can manipulate each engine such that the first engine is weighted at 20% and the second engine is weighted at 80%. The output of the first and second engines can reflect such weights. Multiple engines or e-suites can be run at the same time, in parallel, for identical studies. Multiple engines or e-suites can be run at the same time for different studies from the same patient or from different patients.

Similar engines which find similar findings can be run in parallel, in series, or any combination thereof can be different engines to detect the same finding. For example, a first engine, a second engine, and a third engine can be lung nodule detection engines, but they can be from different engine developers or different medical institutions. Such a configuration can enable comparing the findings from the three engines from different vendors, providing physicians with immediate access to multiple tools and a quick overview of the findings from each engine, immediately during the diagnostic interpretation process which occurs during medical data review. Alternately, the medical data review system can allow the diagnostic review to occur in the common PACS system and then the medical data review to occur after such review using the medical data review system to measure similar and different findings between these diagnostic interpretations.

The difference between typical medical data review and the medical data review system is that common medical data review only seeks to confirm agreement about the overall result of the interpretation, whereas the medical data review system allows for measurement of agreement on a more granular level, including findings, and therefore provides the detail necessary to train an image processing or data processing engine to provide improved future results. While the medical data review system may require more physician engagement time when it is initiated, the availability of highly tuned algorithms will be a result of continued use, and that will reduce the overall physician interpretation time in the future, and provide for improved medical data review results over time.

According to one embodiment, a processing engine can analyze multiple studies with a similar modality and produce an analysis result of "no significant interval change." For example, a processing engine can take two head CT studies, which occur at different times, but of the same modality and body part. An easily extracted report feature from the follow study is "no significant interval change." A processing engine would then run on both CT studies to compare the two to see if there are any differences. If the most recent report is deemed "no significant interval change," a medical data review system function can be to run an engine that can verify the similarity, and therefore provide the ability to agree or disagree with that statement. Often, the reported findings are maintained in reports, and electronic communications, which are inputs to the platform and the relevant contents are provided to the engine when it runs.

According to another embodiment, an engine running on a single study may call another engine or engines to run on a relevant comparison in order to assess stability of the abnormality. This may be multimodality, such as comparing a CT liver lesion engine to an MRI liver lesion engine on a comparison study. In this embodiment, a processing engine running a CT algorithm running on a CT image cohort calls another processing engine or the prior results of an inferenced engine running an MRI algorithm on an MRI image cohort for the same patient, to perform a single comparison task.

The engines and/or e-suites can be run in any configuration such that the probability to detect the findings (or to confirm no findings if that is the goal) is high and/or optimized. The engines and/or e-suites can be run in any configuration to maximize the confidence level to detect the findings. The engines can be run in any configuration such that a user can configure how the output of findings look like (e.g., high probability to detect the finding, low probability to detect the finding, exclude certain findings, include certain findings, selecting normal studies, or any combination thereof).

For example, if a user wants to detect COPD and/or features of COPD, the user can configure one or more COPD engines in parallel, in series, or any combination thereof (i.e., a COPD e-suite), such that the configuration of the engines can have a high probability of detecting COPD or features of COPD. This is an ideal use case for an engine of engines which can self-optimize the weighting of the detection algorithms if it is provided information in the report about which patients did have the targeted findings as confirmed by the physician. As more physicians use the COPD e-suite and confirm (i.e., validate) the output of findings of the COPD e-Suite, the higher ratings the e-Suite can have. High ratings and/or increased confirmations can allow other physicians to recognize which COPD e-suites has the best findings detection rates. This will be evident to users by providing a rating system in the e-commerce site.

In another example, if a user wants to detect lung nodules, the user can select engines that detect specific features of lung nodules, for example, an engine for texture, and engine for nodule shape, an engine for intensity, or any combination thereof. Such engines can be run in parallel, in series, or any combination thereof. Since many lung scans have findings, the most important thing to detect is findings that are likely to result in ordered follow up from the physician. As such, the engine or the engine of engines can be provided the report information or other clinical information in order to improve its detection of lung findings which are most likely to require follow up. Since incidental findings are not missed findings, then one embodiment is a system that filters out incidental findings in the medical data review and diagnostic interpretation process, either by not presenting these findings, or by presenting them and marking them as being likely incidental. Another way to embody the aforementioned process is as a clinical severity score as some incidental findings may or may not have clinical relevance, which affect clinical outcomes. A user can manually replace an engine with another engine through a configuration interface of image processing server 110 (not shown).

Referring back to FIG. 2, according to one embodiment, tracking module 211 is configured to track or record the assignments and processes of image processing engines 113-115. Note that image processing engines 113-115 can be executed in multiple instances (e.g., multiple threads) in a multi-tenancy operating environment. In the multi-tenancy operating environment, different users can log in and be authenticated. Once the users are authenticated and authorized, the users can configure and utilize the image processing engines according to their service or subscription agreements for different studies, different organizations, etc. Tracking module 211 is configured to keep track of which image processing engines are utilized for which medical studies or by which users, on which image cohorts and clinical content cohorts, which resulted in which indexed user data, then generating tracking data 221 (also referred to as engine data) stored in persistent storage device 202, also called a database or databases.

Figure 5:
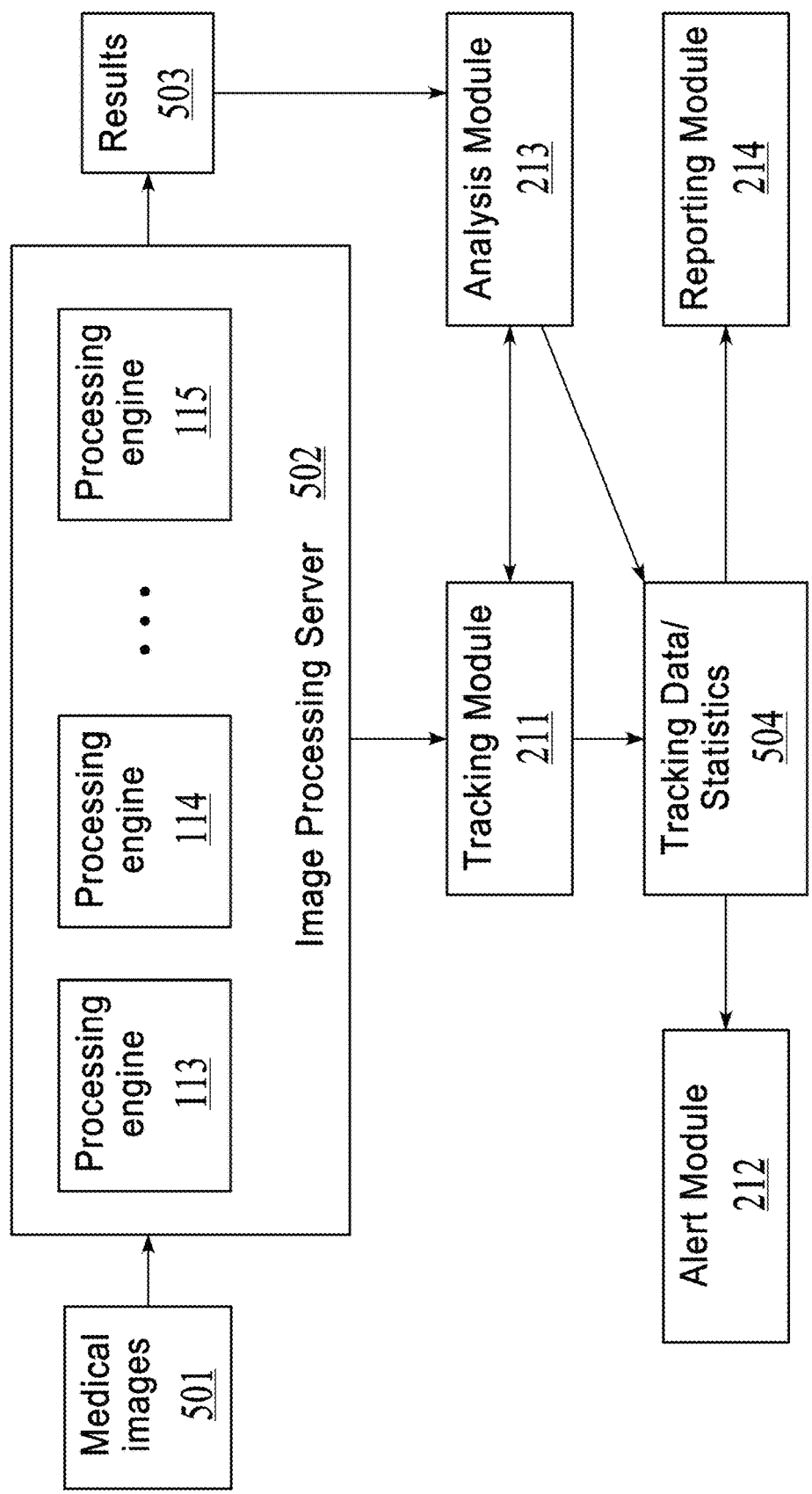
FIG. 5 is a flow diagram illustrating a processing flow of medical image processing according to another embodiment.

FIG. 5 is a processing flow of processing medical images according to one embodiment. Referring to FIG. 5, when medical images 501 are received, processing engines 502 having one or more of image processing engines 113-115 are configured to process the medical images and to generate results 503. Note that images 501 may represent multiple images within a single study, multiple series within a study, or a combination of series and images from multiple studies of different modalities. Results 503 is analyzed by analysis module 213 to generate statistics data. Meanwhile tracking module 211 is configured to track the operations of processing engines 502. Results 503 may be stored as a part of output data 222. Tracking data and statistics data 504 are generated which may be stored as a part of tracking data 221 and/or statistics 223. Based on the tracking data/statistics data 504, if there is any data satisfying a predetermined condition, such as abnormal findings or inconsistent findings, alert module 212 is configured to generate and send an alert to a predetermined device, database(s) or system(s). A report can also be generated based on tracking/statistics data 504 by reporting module 214.

The tracking module 211 can track the engine data (e.g., which studies have been sent to image processing server 110; which studies have been processed by which engines; which studies have been flagged by which engines; which studies have been flagged by multiple engines; which studies have been sent as part of the medical data review samples; engine name; findings; data on validated and/or invalidated machine learned possibly higher likelihood of disease studies; data on features of the images in the studies including, but not limited to, wall thickness, texture, slope, measurements, density, heterogeneity, standard deviation of a range of voxels, or any combination thereof; user interactions of the interpreting physicians, as well as any other persons using the system; time for diagnosis; flagging of studies based on, for example, risk to patient health; order of studies based on risk; or any combination thereof) for the one or more engines (e.g., the first engine). Engine data can be tracked and updated manually, continuously, or automatically after each study is run by one or more engines or e-suites. The medical data review function may involve more than one, two or three physician interpretations, and the medical data review system may be used for serial diagnostic interpretation of unrelated studies by a physician or clinical trial.

In addition, analysis module 213, also referred to as a statistical data engine, can perform an analysis on the tracked engine data for an image processing engine. The statistical data engine 213 can aggregate engine data from one or more image processing servers and one or more databases associated with the medical data review system as well as outside sources, including from one or more medical institutions which provide the engine, and others who only provide image and clinical content cohorts. The statistical data engine 213 can update the statistical data for the all engines and engines of engines based on the engine data, which can be updated on application store 109 as a part of engine ratings. The statistics data may also be stored in persistent storage device 202 as a part of statistics data 223. Similar feedback is collected and displayed for image cohorts and clinical data cohorts.

Note that some or all of the components as shown and described above may be implemented in software, hardware, or a combination thereof. For example, such components can be implemented as software installed and stored in a persistent storage device, which can be loaded and executed in a memory by a processor (not shown) to carry out the processes or operations described throughout this application. Alternatively, such components can be implemented as executable code programmed or embedded into dedicated hardware such as an integrated circuit (e.g., an application specific IC or ASIC), a GPU (Graphics Processing Unit), a digital signal processor (DSP), or a field programmable gate array (FPGA), or similar, which can be accessed via a corresponding driver and/or operating system from an application. Furthermore, such components can be implemented as specific hardware logic in a processor or processor core as part of an instruction set accessible by a software component via one or more specific instructions.

According to another aspect, image processing engines can be utilized as a part of medical data review systems to review the medical findings performed by a set of physicians. The image processing engines are utilized to screen and identify any images that highly likely have abnormal findings. The identified images are then reviewed by a set of physicians to verify and confirm the findings. As a result, for thousands of medical images that need to be reviewed, the image processing engines can perform massive image processing operations to preliminary identify the abnormal images. Those images are then reviewed by the physicians to confirm the findings. If the findings of the image processing engines and the reviewing physicians are consistent, the operations of the image processing engines involved can be validated, i.e., the algorithms used by the image processing engines are validated. Otherwise, such algorithms may need further fine tune or training, for example, using machine learning methods.

Alternatively, if there is any inconsistency between the machine findings and the physician findings, an indication in the database(s) and notifications in the restful services and/or API have the effect of sending notification to the desired systems and staff. These identified conflicting studies are then sent for secondary physician review. Once both review results are known, reconciliation through the analysis module can result in confirmation of the engine accuracy or improvement to the engine.

According to certain embodiments, a variety of image processing tools can be accessed by a user using the diagnostic image processing features of the medical data review system. Alternatively, such image processing tools can be implemented as image processing engines 113-115 which are then evoked in other third party systems, such as a PACS or EMR, or other clinical or information system. The following are examples of medical image processing tools present in a current leading semi-automated image viewing and advanced visualization system that may be included and/or further automated, or converted to engines, as part of the image processing system described above. These examples are provided for illustrative purposes and not intended to be a limitation.

Vessel Analysis tools may include a comprehensive vascular analysis package for CT and MR angiography capable of a broad range of vascular analysis tasks, from coronary arteries to aortic endograft planning and more general vascular review, including carotid and renal arteries. Auto-centerline extraction, straightened view, diameter and length measurements, CPR and axial renderings, and Vessel Track mode for automated thin-slab MIP may be included.

Calcium scoring tools may include identification of coronary calcium with Agatston, volume and mineral mass algorithms. An integrated reporting package with customization options may be included.

Time-dependent analysis (TDA) tools may include time-resolved planar or volumetric 4D brain perfusion examinations acquired with CT or MR. The TDA tools may support color or mapping of various parameters such as mean enhancement time and enhancement integral, with semi-automated selection of input function and baseline, to speed analysis. TDA tools may support rapid automated processing of dynamic 4D area-detector CT examinations to ensure interpretation within minutes of acquisition.

CT/CTA (Computed tomography angiography) subtraction tools are used in the removal of non-enhancing structures (e.g. bone) from CT angiography examinations, the CT/CTA option includes automatic registration of pre- and post-contrast images, followed by a dense-voxel masking algorithm which removes high-intensity structures (like bone and surgical clips) from the CTA scan without increasing noise, aiding with the isolation of contrast-enhanced vascular structures.

Lobular decomposition tools identify tree-like structures within a volume of interest, e.g. a scan region containing a vascular bed, or an organ such as the liver. The LD tool can then identify sub-volumes of interest based on proximity to a given branch of the tree or one of its sub-branches. Research applications include the analysis of the lobular structure of organs.

General Enhancement & Noise Treatment with Low Exposure tools may include an advanced volumetric filter architecture applying noise management techniques to improve the effectiveness of 3D, centerline, and contouring and segmentation algorithms even when source image quality is not optimum.

The Spherefinder tools perform automated analysis of volumetric examinations to identify the location of structures with a high sphericity index (characteristics exhibited by many nodules and polyps). Spherefinder is often used with Lung or Colon CT scans to identify potential areas of interest.

Segmentation, analysis & tracking tools support analysis and characterization of masses and structures, such as solitary pulmonary nodules or other potential lesions. Tools may identify and segment regions of interest, and then apply measurement criteria, such as RECIST and WHO, leading to tabulated reporting of findings and follow-up comparison. Display and management of candidate markers from optional detection engines may be supported, including Spherefinder.

Time volume analysis tools may provide automated calculation of ejection fraction from a chamber in rhythmic motion, such as a cardiac ventricle. A fast and efficient workflow may be included to enable the user to identify the wall boundaries of interest (e.g. epicardium and endocardium) and, based on these user-confirmed regions of interest, to report ejection fraction, wall volume (mass) and wall thickening from multi-phasic CT data. Tabulated reporting output is included.

Maxillo-facial tools support the analysis and visualization of CT examinations of the Maxillo-facial region, these tools apply the CPR tool to generate "panoramic" projections in various planes and of various thicknesses, and cross-sectional MPR views at set increments along the defined curve plane.

Applicable to endoluminal CT or MR investigations such as colon, lungs, or blood vessels, the Flythrough tools supports side-by-side review, painting of previously-viewed areas, percent coverage tracking, and multiple screen layouts including forward, reverse, fisheye and flat volume rendered views. Tools for contrast subtraction, "Cube View", and integrated contextual reporting may be supported. Display and management of candidate markers from optional detection engines may be supported, including iNtuition's Spherefinder.

The Volumetric Histogram tools allow a volume of interest to be segmented and analyzed for composition. Research applications include the analysis of low-attenuation regions of the lungs, threshold-based division of tumors into voxel populations, investigation of thrombosed vessels or aneurysms, or other pathology.

Findings workflow tools provide a framework for tracking findings across serial examinations. A database holds measurements and key images, and provides support for structured comparisons and tabulated reporting of findings over time, such as the RECIST 1.1 approach for presenting serial comparisons. The Annotation and Image Markup (AIM) XML schema may be supported, for automated integration with voice-recognition systems or clinical databases, and Word-based reports may be derived from the database.

With these tools, any two CT, PET, MR or SPECT series, or any two-series combination thereof can be overlaid with one assigned a semi-transparent color coding and the other shown in grayscale and volume rendering for anatomical reference. Automatic registration is provided and subtraction to a temporary series or to a saved, third series is possible. Support for PET/MR visualization is included.

Certain MR examinations (for example, Breast MR) involve a series of image acquisitions taken over a period of time, where certain structures become enhanced over time relative to other structures. These tools feature the ability to subtract a pre-enhancement image from all post-enhancement images to emphasize visualization of enhancing structures (for example, vascular structures and other enhancing tissue). Time-dependent region-of-interest tools may be provided to plot time-intensity graphs of a given region.

Parametric mapping tools are an enhancement to the Multi-Phase MR tools, the parametric mapping option pre-calculates overlay maps where each pixel in an image is color-coded depending on the time-dependent behavior of the pixel intensity. As an example, this tool can be used in Breast MR to speed identification and investigation of enhancing regions.

The MultiKv tools provide support for Dual Energy and Spectral Imaging acquisitions from multiple vendors, providing standard image processing algorithms such as segmentation or contrast suppression, as well as generic toolkits for precise analysis and development of new techniques.

These examples, and most functions of current advanced image analyses and clinical data analyses are capable of being supported in the Medical data review Platform. However, the capabilities of engines as well as engines of engines goes much further and can accommodate tools with higher intelligence and automation, as well as to deliver individually tailored workflows by adapting engines to the individual or group preferences.

The embodiments described above can be applied to a variety of medical areas. For example, the techniques described above can be applied to vessel analysis (including Endovascular Aortic Repair (EVAR) and electrophysiology (EP) planning). Such vessel analysis is performed for interpretation of both coronary and general vessel analysis such as carotid and renal arteries, in addition to aortic endograft and electro-physiology planning. Tools provided as cloud services of the platform for locally-sited or cloud sited deployment include auto-centerline extraction, straightened view, diameter and length measurements, color overlays, fusion mapping, Curved Planar Reformation (CPR) and axial renderings, as well as charting of the vessel diameter vs. distance and cross-sectional views. The vessel track tool provides a Maximum Intensity Projection (MIP) view in two orthogonal planes that travels along and rotates about the vessel centerline for ease of navigation and deep interrogation. Plaque analysis tools provide detailed delineation of non-luminal structure such as soft plaque, calcified plaque and intra-mural lesions.

In addition, the techniques described above can be utilized in the area of endovascular aortic repair. According to some embodiments, vascular analysis tools provided as similar cloud services support definition of report templates which captures measurements for endograft sizing. Multiple centerlines can be extracted to allow for planning of EVAR procedures with multiple access points. Diameters perpendicular to the vessel may be measured along with distances along the two aorto-iliac paths. Custom workflow templates may be used to enable the major aortic endograft manufactures' measurement specifications to be made as required for stent sizing. Sac segmentation and volume determination with a "clock-face" overlay to aid with documenting the orientation and location of branch vessels for fenestrated and branch device planning, may also be used. Reports containing required measurements and data may be generated.

The techniques described above can also be applied in the left atrium analysis mode, in which semi-automated left atrium segmentation of each pulmonary vein ostium is supported with a distance pair tool, provided as cloud services, for assessment of the major and minor vein diameter. Measurements are automatically detected and captured into the integrated reporting system. These capabilities can be combined with other vessel analysis tools to provide a comprehensive and customized EP planning workflow for ablation and lead approach planning.

The techniques described above can also be utilized in calcium scoring. Identification of coronary calcium is supported with Agatston, volume and mineral mass algorithms being totaled and reported. Results may be stored in an open-format database along with various other data relating to the patient and their cardiovascular history and risk factors. A customized report can be automatically generated based upon these data. Also includes report generation as defined by the Society of Cardiovascular Computed Tomography (SCCT) guidelines.

The techniques described above can also be utilized in a time-volume analysis (TVA), which may include fully-automated calculation of left ventricular volume, ejection fraction, myocardial volume (mass) and wall thickening from multi-phasic data.

The techniques described above can also be utilized in the area of segmentation analysis and tracking (SAT), which includes supports analysis and characterization of masses and structures in various scans, including pulmonary CT examinations. Features include segmentation of masses, reporting of dimensions and volume, graphical 3D display of selected regions, support for follow-up comparisons including percent volume change and doubling time, and support for application and review of filter results (e.g., sphericity).

The techniques described above can also be utilized in the area of flythrough which may include features of automatic segmentation and centerline extraction of the colon, 2D review includes side-by-side synchronized supine and prone data sets in either axial, coronal or sagittal views with representative synchronized endoluminal views. 3D review includes axial, coronal and sagittal MPR or MIP image display with large endoluminal view and an unfolded view that displays the entire colon. Coverage tracking is supported to ensure 100% coverage with stepwise review of unviewed sections, polyp identification, bookmark and merge findings, as well as a cube view for isolating a volume of interest and an integrated contextual reporting tool. Support is provided for use of filter results (e.g., sphericity).

The techniques described above can also be utilized in the area of time-dependent analysis (TDA), which provides assessment analysis of the time-dependent behavior of appropriate computerized tomographic angiography (CTA) and/or MRI examinations, such as within cerebral perfusion studies. Multiple time-dependent series are analyzed at the same time, and a procedural workflow for selecting input and output function and regions of interest is provided. Exportation of values for blood flow, blood volume and transit time maps are supported or exported in DICOM or other image formats. Other outputs include calculation of various time-dependent parameters.

The techniques described above can also be utilized in the area of CTA-CT subtraction, which includes automatic registration of pre- and post-contrast images, followed by subtraction or dense-voxel masking technique which removes high-intensity structures (like bone and surgical clips) from the CTA scan without increasing noise, and leaving contrast-enhanced vascular structures intact.

The techniques described above can also be utilized in dental analysis, which provides a CPR tool which can be applied for review of dental CT scans, offering the ability to generate "panoramic" projections in various planes and of various thicknesses, and cross-sectional MPR views at set increments along the defined curve plane.

The techniques described above can also be utilized in the area of multi-phase MR (basic, e.g. breast, prostate MR). Certain MR examinations (for example, breast, prostate MR) involve a series of image acquisitions taken over a period of time, where certain structures become enhanced over time relative to other structures. Function include the ability to subtract a pre-enhancement image from all post-enhancement images to emphasize visualization of enhancing structures (for example, vascular structures and other enhancing tissue). Time-dependent region-of-interest tools are provided to plot time-intensity graphs of a given region.

The techniques described above can also be utilized in parametric mapping (e.g. for multi-phase Breast MR), in which the parametric mapping module pre-calculates overlay maps where each pixel in an image is color-coded depending on the time-dependent behavior of the pixel intensity.

The techniques described above can also be utilized in finding sphericity in objects within image datasets. This is often used with lung or colon CT scans to identify potential areas of interest.

The techniques described can also be utilized in fusion for CT/MR/PET/SPECT. Any two CT, PET, MR or SPECT series, or any two-series combination can be overlaid with one assigned a semi-transparent color coding and the other shown in grayscale and volume rendering for anatomical reference. Automatic registration is provided and subtraction to a temporary series or to a saved, third series is possible.

The techniques described above can also be utilized in the area of Lobular Decomposition. Lobular Decomposition is an analysis and segmentation tool that is designed to detect and segment anatomical structures. For any structure or organ region which is intertwined with a tree-like structure (such as an arterial and/or venous tree), the tool calculates volumes of interest, as well as the trees related to it, and partitions the volumes into lobes or territories which are most proximal to the tree or any specific sub-branch thereof. This generic and flexible tool has potential research applications in analysis of the liver, lung, heart and various other organs and pathological structures.

The techniques described above can also be utilized in the area of volumetric histogram calculations. Volumetric histogram partitions a given volume of interest based on constituent voxels creating groups or populations of different intensity or density ranges. This can be used, for example, to support research into disease processes such as cancer (where it is desirable to analyze the composition of tumors, in an attempt to understand the balance between active tumor, necrotic tissue, and edema), or emphysema (where the population of low-attenuation voxels in a lung CT examination may be a meaningful indicator of early disease).

The techniques described above can also be utilized in the area of motion analytics. Motion analytics provides a powerful 2D representation of a 4D process, for more effective communication of findings when interactive 3D or 4D display is not available. Any dynamic volume acquisition, such as a beating heart, can be subjected to the motion analysis, to generate a color-coded "trail" of outlines of key boundaries, throughout the dynamic sequence, allowing a single 2D frame to capture and illustrate the motion, in a manner that can be readily reported in literature. The uniformity of the color pattern, or lack thereof, reflects the extent to which motion is harmonic, providing immediate visual feedback from a single image.

Figure 6:
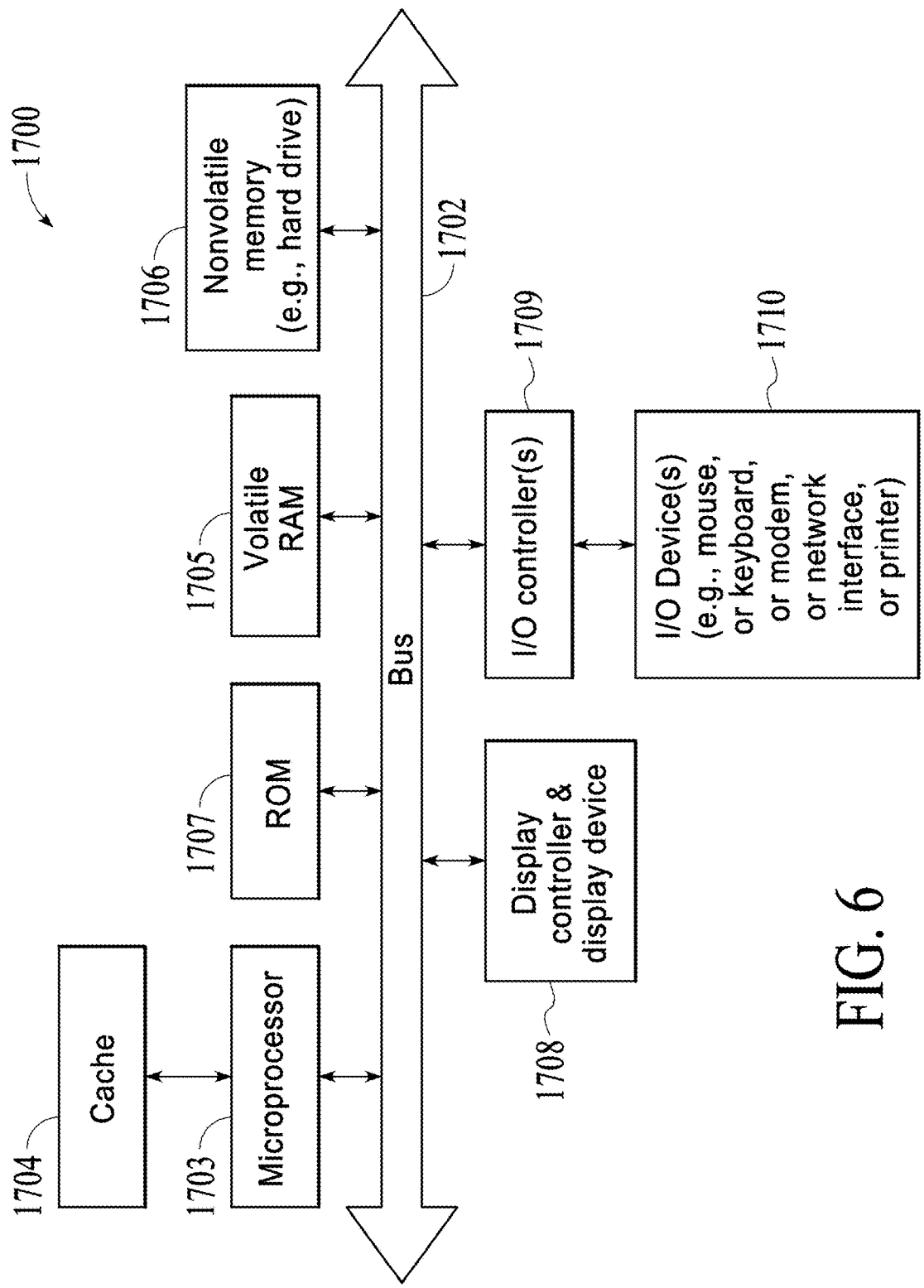
FIG. 6 is a block diagram of a data processing system, which may be used with one embodiment.

FIG. 6 is a block diagram of a data processing system, which may be used with one embodiment. For example, the system 1700 may be used as part of a server or a client as described above. For example, system 1700 may represent image processing server 110 described above, which is communicatively coupled to a remote client device or another server via network interface 1710. Note that while FIG. 6 illustrates various components of a computer system, it is not intended to represent any particular architecture or manner of interconnecting the components; as such details are not germane to the present invention. It will also be appreciated that network computers, handheld computers, cell phones and other data processing systems which have fewer components or perhaps more components may also be used with the present invention.

As shown in FIG. 6, the computer system 1700, which is a form of a data processing system, includes a bus or interconnect 1702 which is coupled to one or more microprocessors 1703 and a ROM 1707, a volatile RAM 1705, and a non-volatile memory 1706. The microprocessor 1703 is coupled to cache memory 1704. The bus 1702 interconnects these various components together and also interconnects these components 1703, 1707, 1705, and 1706 to a display controller and display device 1708, as well as to input/output (I/O) devices 1710, which may be mice, keyboards, modems, network interfaces, printers, and other devices which are well-known in the art.

Typically, the input/output devices 1710 are coupled to the system through input/output controllers 1709. The volatile RAM 1705 is typically implemented as dynamic RAM (DRAM) which requires power continuously in order to refresh or maintain the data in the memory. The non-volatile memory 1706 is typically a magnetic hard drive, a magnetic optical drive, an optical drive, or a DVD RAM or other type of memory system which maintains data even after power is removed from the system. Typically, the non-volatile memory will also be a random-access memory, although this is not required.

While FIG. 6 shows that the non-volatile memory is a local device coupled directly to the rest of the components in the data processing system, the system may utilize a non-volatile memory which is remote from the system; such as, a network storage device which is coupled to the data processing system through a network interface such as a modem or Ethernet interface. The bus 1702 may include one or more buses connected to each other through various bridges, controllers, and/or adapters, as is well-known in the art. In one embodiment, the I/O controller 1709 includes a USB (Universal Serial Bus) adapter for controlling USB peripherals. Alternatively, I/O controller 1709 may include an IEEE-1394 adapter, also known as FireWire adapter, for controlling FireWire devices.

When reviewing a pre-completed report, a physician can use a reporting solution, such as the product PowerScribe 360 Reporting available from Nuance Communications, Inc., which allow the physician to use dictation or typing of natural language to amend a pre-completed report. Alternatively, or in addition, structured reporting solutions that use programmed logic to select related words based on the patient condition and previous selections can be used by a physician to create more uniform reports. Such features utilize a one-way communication between the physician findings and the report.

There is also an emerging field of artificial intelligence or machine learning applied to image processing and report creation such that information or inferences drawn from the images can be used to populate some or all of the image interpretation report. See for example, the Galileo Clinical Decision Support system available from Galileo CDS, Inc., machine learning solutions for medical imaging analysis available from RadLogics, Inc., and clinical support products available from Enlitic, Inc.

As described below, a system allows bidirectional communication between an image viewer and solution reporting solution. The system includes the ability to demonstrate computer generated findings within the viewer such that the generated findings can be seen, accepted, adjusted, deleted or replaced by the reviewing physician. Such report changes by the physical automatically update the report based on physician supplied information. Similarly, if a physician replaces a number in a report with a different measurement value made via a different measurement in the image viewer, the system will prompt the physician to accept the deletion of the old measurement that was replaced, or automatically do this based on this and other preferences.

Such a system that allows bidirectional communication between an image viewer and solution reporting solution assists a physician's natural predisposition to start with the images, and helps to prevent the creation of bias through a priori knowledge. This also helps to avoid the case where physician starting with a pre-populated report would either need to accept the computer-generated findings blindly, or verify them bouncing between the findings and the images. Workflow is not broken because changes in the findings within the image viewer may not update the results in the report. More importantly, the changes in the findings in the report which were made by the physician's further interrogation and measurements within the images are coordinated such that the original measurements or annotations made in the images by the computer automation methods are removed or replaced. This avoids confusion in the patient record that can occur when images are stored along with the final report, and avoids unnecessary work to delete computer generated findings in the case they are duplicated and not updated. Such workflow confusion and inefficiency is resolved by a bidirectional updating of physician-adjusted, added, or deleted findings within the report and the diagnostic interpretation viewer, irrespective of the point of the change, whether it be the report value that is changed, or the measurement or image process used in the image viewer being adjusted to create a new resultant value.

The artificial intelligence findings within the image interpretation environment (collectively referred to as artificial intelligence finding) system and method can have bidirectional data flow from the image interpretation environment to structured reports. The artificial intelligence finding can have bidirectional flow from the image interpretation environment report to a cloud (e.g., WIA Cloud).

The reports can be structured or unstructured so that the system is valuable to allow a physician using manual reporting methods to create measurements in the viewer that are linked to the values that are placed in the report. With a more advanced structured or other reporting system or image processing engines, there may be a plurality of measurements and findings already created, up to and including a completely finalized report which has had no prior physician input.

The artificial intelligence finding can have bidirectional flow from the image interpretation environment and with the image processing system generating the automated findings within images. Additionally, artificial intelligence finding can communicate the changes that the physician has made back to the image processing system to allow it to improve based upon this 'training data' and physician ground-truthing so that the computer-generated findings are adjusted and/or accepted by the physician, as further described above.

The artificial intelligence finding can have findings that can be adjusted by users in the image interpretation environment, which in turn adjusts the reported findings. The reported findings can be within a structured report. The artificial intelligence finding can have workflows that enable users' eyes/vision/concentration to remain within the image interpretation environment with artificial intelligence findings presented efficiently within the images. The artificial intelligence finding can allow user adjustments in the images that can be tracked, categorized, learned, and optimized to provide improved workflow. The artificial intelligence finding can generate findings within the image interpretation environment and machine learn and/or deep learn based on adjustments to the findings by a user or a group of users. Based on machine learning and/or deep learning, artificial intelligence finding can predict and/or generate findings for a specific user and/or group.

For example, a computer processing engine running in an image processing system can indicate the area of the maximum diameter of the patient's abdominal aorta by first placing a centerline through the vessel in three dimensions, then create a contour or surface edge along the circumference of the long vessel wall which is irregular and not a perfect circle. The computer processing engine then places many planes at a ninety-degree angle to this centerline and finds the location where this plane resides within the plane. These regions of interest are measured using various methods such as calculating the RESIST measurement or the total area to determine which has the highest value and is therefore the greatest. This edge contour and measurement is returned to the interpretation viewer and the reporting system with a link that allows both systems to know that this measurement, of that type, in the specific location it was made are correlated.

In addition, computer processing engine can adapt the viewer to the preferences of the physician to allow for an optimized workflow when interpreting studies that have certain types of findings. Further, the auto-generated findings themselves can become individualized and/or improved based on the 'training' that the physician, a group of physicians, or the totality of users of the system provide over time.

Figure 7:
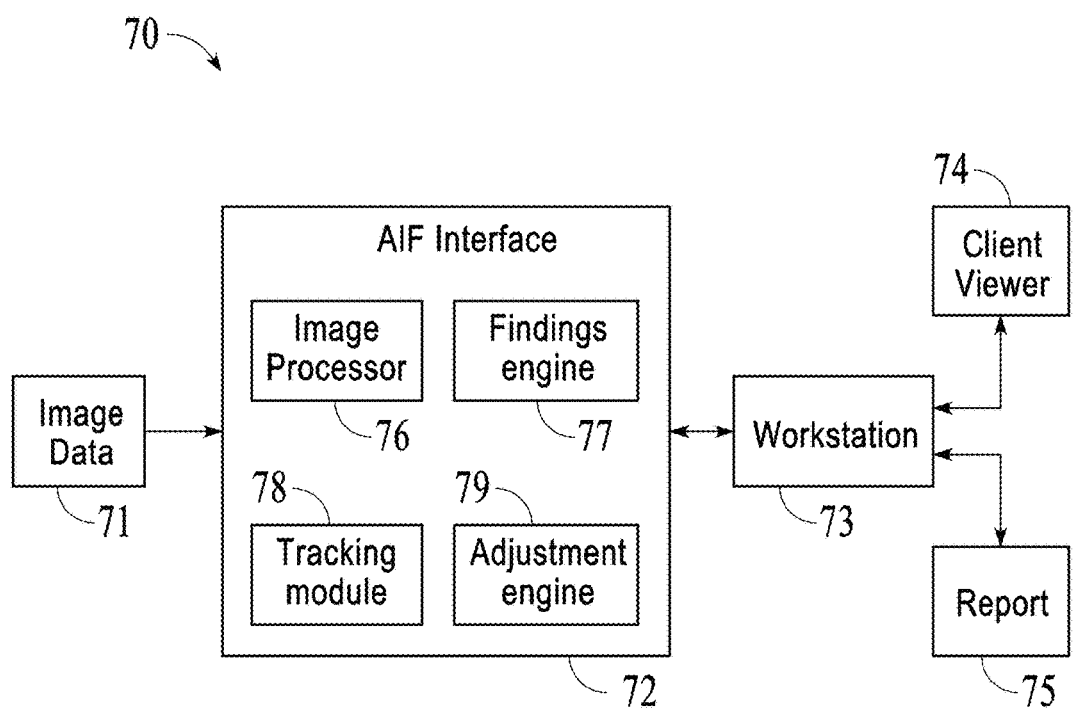
FIG. 7 is a block diagram illustrating an artificial intelligence findings system in accordance with an embodiment.

FIG. 7 is a simplified block diagram illustrating an artificial intelligence findings system 70 within a medical image interpretation system or another image interpretation environment. For example, artificial intelligence finding system 70 can include image data 71 sent to an artificial intelligence finding interface 72 over a network. The artificial intelligence finding interface 72 can be, for example, communicatively connected to at least one workstation over a network, as represented by workstation 73. Work station 73 can be, for example, a tablet, mobile device, laptop, desktop, or any combination thereof. Work station 73 functions as a diagnostic review system that can include a client viewer 74, a report 75 (that can be structured or unstructured), web page output, results available for pickup by any system capable of communicating with the interface or any combination thereof. The diagnostic review system allows the user to view and confirm findings. The diagnostic review system tracks whether the findings are unviewed, viewed, unconfirmed or confirmed. The diagnostic review system allows the user to modify the images to produce derived images. Changes made to the report are reflected in the images displayed by the viewer. Changes made to the images displayed by the viewer are reflected in report. While FIG. 7 shows a diagnostic review system including both a client viewer 74 and a report, a diagnostic review system may include just the client viewer without a report or a reporting system or may include just a report or reporting system without a client viewer.

FIG. 7 is a simplified block diagram illustrating an artificial intelligence findings system 70 within a medical image interpretation system or another image interpretation environment. For example, artificial intelligence finding system 70 can include image data 71 sent to an artificial intelligence finding interface 72 over a network. The artificial intelligence finding interface 72 can be, for example, communicatively connected to at least one workstation over a network, as represented by workstation 73. Work station 73 can be, for example, a tablet, mobile device, laptop, desktop, or any combination thereof. Work station 73 functions as a diagnostic review system that can include a client viewer 74, a report 75 (that can be structured or unstructured), web page output, results available for pickup by any system capable of communicating with the interface or any combination thereof. The diagnostic review system allows the user to view, adjust and confirm findings in either user experience interface. Findings can be shown in the viewer only, in the report only, or the viewer and the report together. Settings and user preferences along with tracked user behavior are capable of modifying the type and quantity of findings which exhibit these behaviors. The diagnostic review system tracks whether the findings are unviewed, viewed, adjusted, unadjusted, unconfirmed, confirmed, unreported or reported. The diagnostic review system allows the user to modify the images to produce new or adjusted findings, delete findings, create new derived images with findings or create new derived series without findings. Changes made to the report are reflected in the findings displayed in the viewer or which images are displayed by the viewer. Changes, additions or deletions made to the findings in the images or the images displayed by the viewer are reflected in report.

For example, report 75 represents a reporting data structure that is completed by a physician reporting findings based on the image data. The report 75 can be pre-populated with candidate finding based on interpretations of the image data by AIF interface and/or client viewer 74. The user (e.g., a physician) upon reviewing the report and/or interacting with client viewer 74 adjusts the candidate findings to finalize the report. Changes made to candidate findings in report 74 are used by the medical image interpretation system to make adjustments to the images shown in client viewer 74. Likewise, changes made to the images shown in client viewer 74 are used by the medical image interpretation system to made adjustments to findings in report 74. When the user is finished adjusting the findings, report 74 is in final form.

The arrows between artificial intelligence findings system 70 and work station 73 indicates that artificial intelligence findings system 70 includes a communication interface that provides findings from artificial intelligence findings system 70 to a diagnostic review system within work station 73. For example, artificial intelligence findings system 70 and work station 73 are both within a medical image interpretation system.

Image data 71 can include any modality of images (e.g., X-ray, CT, MRI, or any combination thereof). Image data 71 are interpreted by findings engine 77 to produce the findings. The findings can be, for example, something of medical significance such as a disease, an indication, a feature, an object, a shape, a texture, a measurement, a flag, a rendering, a contour, or any combination thereof. Data-only elements (non-image data) are simultaneously or independently supported. Typically, these findings are of clinical significance, but may be of workflow significance or even system performance significance. Such findings may be using industry standard communications and/or methods but may be unique to the image or information processing engine used, with no difference in the functioning of artificial intelligence finding system 70. Findings engine 71 that receives image data and processes the image data to generate findings based on the image data, associated patient information, and based on image interpretation algorithms that take into account stored preferences for a user The artificial intelligence finding interface 72 can include an image processor 76, a findings engine 77, a tracking module 78, an adjustment engine 79, storage (not shown), or any combination thereof. Image processor 76 can process image data 71, for example, to generate findings. For example, image processor 76 can have processing functions such as a color map overlay, where the density or signal intensity of a certain pixel or nearby pixel changes over time during the image acquisition. This is also known as parametric mapping. The processing functions can also include contours which define the area if high and low intensity or signal changes, defining an edge or "contour" which can then be used to define the edges of an organ or specific region of interest within an organ, such as the ventricle of the heart, or any one of the clinically defined segments of the liver. Quite often, these contours and segmentation procedures are used as the basis for an analytical calculation such as the volume of an organ, the differentiation of tissue types, etc. As such contours can be in one dimension (point to point), or can be a group of points connected at intervals in three dimensions, or even tracked over time as a series of multi-point contours over time (e.g., four dimensions). Such contouring and segmentation are often implemented by selecting a threshold that adjusts the brightness or signal to get the desired result according to clinical knowledge. The goal of the artificial intelligence engine is to look at hundreds of these physician thresholded and contoured images and to simulate the actions of a physician to generate images for a reviewing physician. This allows a reviewing physician to accept or make minor adjustments to the generated images, avoiding many other steps. In some cases, the quantification may be tangential but appreciated by the physician and accepted without further evaluation. For example, the amount of calcium in the coronary arteries can be calculated by a manual, semi-automated or fully automated system. If the physician is reviewing the cardiac function, it may well be acceptable to include the fully automated calcium score and push this into the report as described above. The report becomes richly populated and clear about which are physician reviewed and which are automatically generated. In the case that these data are included often, the physician can be prompted as to whether this is a default behavior. The report may contain status indications for each finding as to whether that particular finding has been adjusted, accepted, replaced or rejected, or made as an original independent finding by the end user. The preferences and actions of the report user can be tracked and measured to improve the quality of the initial report and to require less and less input in order to achieve an accepted report, potentially not needing any input over time.

Adjustment engine 79 can enable a user to adjust findings within the image interpretation environment (i.e., client viewer 74) such that the adjustments can be viewed in report 75 and/or the image interpretation environment. Adjustment engine 79 can enable a user to adjust findings within report 75 such that the adjustments can be viewed in the image interpretation environment. The adjustments can be in real-time, periodically, or any combination thereof. Any adjustment can have a confirmation indication to indicate to the user to confirm such adjustments of findings. For example, the adjustments prompted by the communication interface within artificial intelligence interface 72, when notified of changes to findings by a client viewer or reporting system within workstation 73.

Findings engine 77 can generate findings based on image data 71 and/or image processor 76. Findings engine 77 can generate findings related to the image processing functions. Tracking engine 78 can track initial findings, manipulated findings, adjusted findings, or any combination thereof. For example, the user can be provided a summary of findings the user has not looked at, or that the user has not adjusted, so as to avoid missing any. Alternatively, the physician may want to start with the image interpretation and happen across unvalidated measurements that the physician can accept or reject. This means in the report, the measurements that were not looked at, were deleted, were adjusted, and were added completely new and by the user should be able to be uniquely indicated in the report (via color or a note, or categorization in the report) etc. For example, the user is prompted to review findings that have not been viewed, confirmed, rejected, reported or adjusted. A user option is provided for the system to mark findings as rejected or to omit findings from the report when the findings are displayed on the client viewer to the user and the user makes no further interaction with the displayed findings or does not confirm the displayed findings.

For example, artificial intelligence finding interface 72 can be, for example, implemented by the medical image interpretation system shown in FIG. 7 or by a similar app store system. Alternatively, artificial intelligence finding interface 72 can be, for example, implemented on a single server, a combination of servers, applications available on a cloud, or some other system. Alternatively, instead of a single separate server, a communication interface can be, for example, used where the viewer supports receiving measurements from an image processing cloud, and provides adjustments back.

Figure 8:
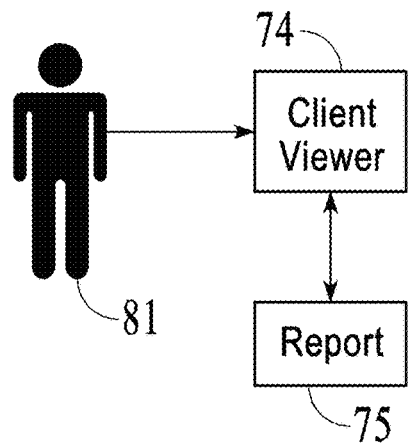
FIG. 8, FIG. 9 and FIG. 10 are block diagrams illustrating bidirectional flow of data within an artificial intelligence findings system in accordance with various embodiments.
Figure 9:
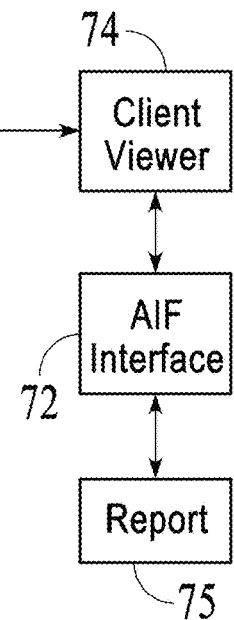
Figure 10:
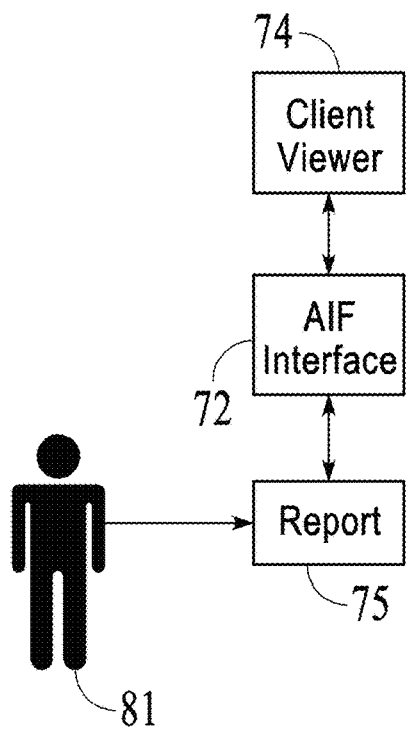

FIG. 8, FIG. 9 and FIG. 10 are block diagrams illustrating bidirectional flow of data according to certain embodiments. In FIG. 8, a user 81 can adjust the initial findings displayed in client viewer 74, report 75, or any combination thereof generated by the artificial intelligence finding interface 72. For example, user 81 is a physician, a radiologist, a technician, another type of medical professional, or any user of artificial intelligence finding interface 72. When user 81 manipulates the findings in client viewer 74, the findings can be updated in report 75.

FIG. 9 illustrates that user 81 can adjust the initial findings displayed in client viewer 74 generated by the artificial intelligence finding server. The manipulated findings can be sent to the artificial intelligence finding interface 72 to be tracked, updated, optimized, machine learned, or any combination thereof. The artificial intelligence finding interface 72 can send the manipulated findings to report 75 such that the initial finding can be replaced by the manipulated finding. Report 75 can display the manipulated finding.

FIG. 10 illustrates that user 81 can manipulate initial findings displayed in report 75 such that the manipulated findings can be sent to the artificial intelligence finding interface 72. The artificial intelligence finding interface 72 can update client viewer 74 with the user manipulated finding which can be displayed in client viewer 74.

Figure 11:
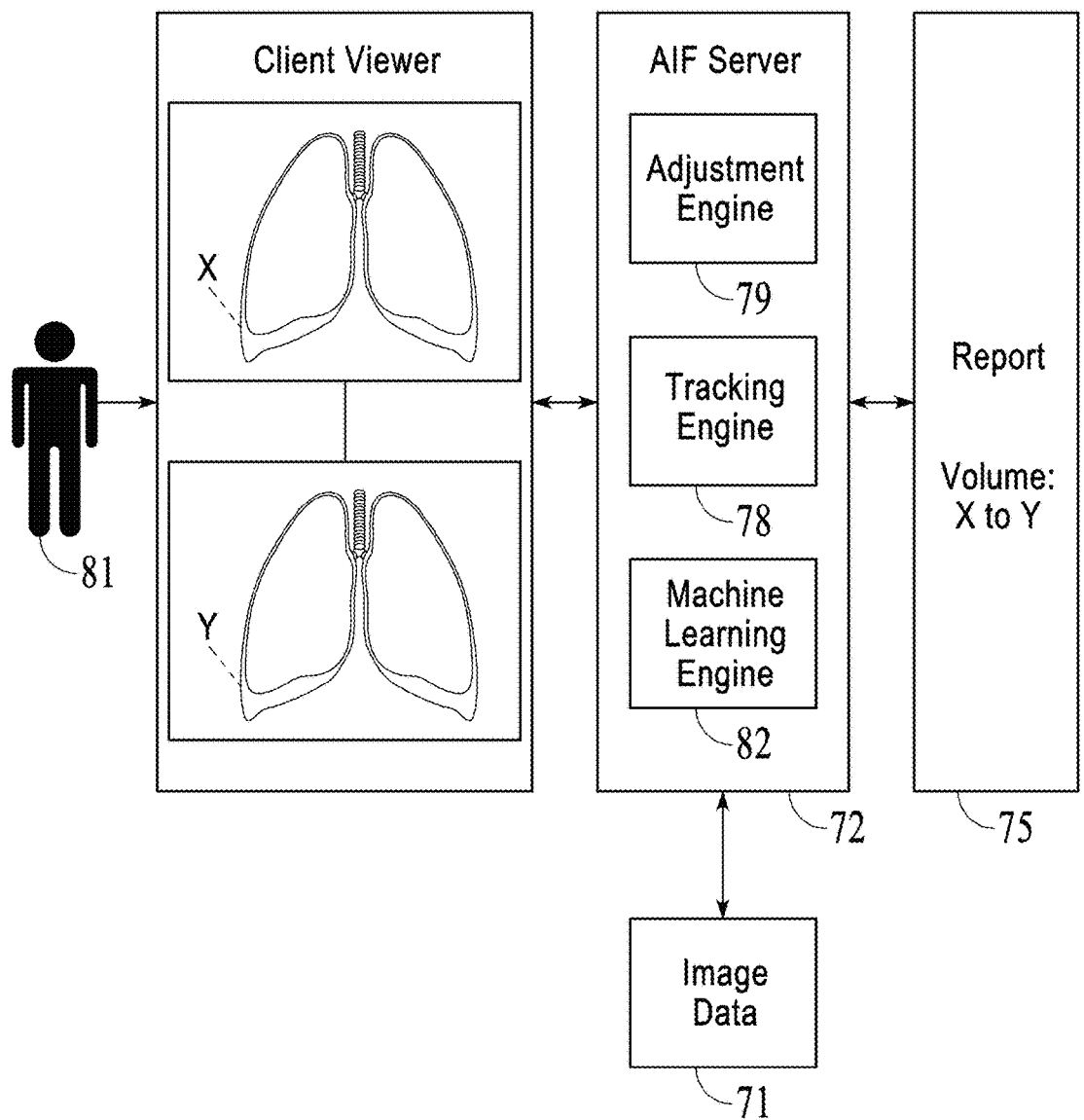
FIG. 11 is one example of artificial intelligence finding system in accordance with an embodiment.

FIG. 11 is one example of artificial intelligence finding system 70. Image data from a lung can be processed by the artificial intelligence finding interface 72. The initial findings, for example volume X of a portion of a lung, based on the image data can be generated by the artificial intelligence finding interface 72 and displayed in the image interpretation environment (i.e., client viewer 74) and/or report 75. The initial findings can be tracked via tracking module 78. For example, tracking module tracks findings and adjustments made to findings by a user when the user uses a diagnostic review system, such as implemented within workstation 73. For example, tracking module 78 produces tracking information based on the findings and adjustments made to the findings by a current user and usage patterns ascertainable based other users User 81 can manipulate the initial findings and/or change the initial contours to change the volume, for example from volume X to volume Y, within the image interpretation environment, as shown in FIG. 11. Tracking engine 78 can track the manipulated finding such that tracking module 78 can store in memory the initial findings from image data 71 and the manipulated finding. Adjustment engine 79 can update client viewer 74 and/or report 75 to display the manipulated finding (i.e., replace the initial finding of volume X with the manipulated finding of volume Y). Such a workflow can allow user 81 to adjust findings within client viewer 74 which in turn can automatically update report 75 allowing user 81 to focus on the images. The machine learning engine can learn based off of the user adjustments, for example, user 81 changing the lung volume from volume X to volume Y. Such machine learning can allow precise findings for user 81 for subsequent findings.

In one embodiment, automated contours can generate measurements. When a measurement does not match what user 81 measured or they adjust it, it can be flagged as not matching. The artificial intelligence engine can learn (deep learn, machine learn, log or any combination thereof) the difference and begin to notice trends in the feedback in order to suggest improved findings to the user, or to suggest changes in system settings, or even to suggest changes in clinical workflow that better match best practices, group practices, or the practices of certain colleagues, which are individually tailored based on the current user preferences and detected practice differences. In addition, some differences can be accommodated, such as the case where one physician contours anatomy consistently larger or more generously than others do. Rather than changing the practice of the physician or considering that the best practice variance is a problem, the system can accept that the physician has this preference and try to use its bidirectional learning capabilities to instead present the physician with findings adjusted in a way that they will accept them more often without adjustment. This can be done with user to user adaptation so that someone who contours lesions large and someone who contours lesions small can have individualized suggestions.

For example, the processing engines working in combination with tracking module 78 can essentially "learn" the display preferences and adapt them to user preferences or belief system. For example, there is sometimes a 40% or greater inter-physician variance in the areas or volumes they measure, when all other variables are constant. In such case, a processing engine can learn a "group think" ground truth normal result based on collective use. Then, it can consider information from tracking module 78, to adapt which findings are important to user 81 and to adjust these initial findings in accordance with the measured variance between her beliefs and adjustment actions and such ground truth group think norm result. This can be applied not only to findings, but to the layout of images, and which tools are evoked or available during interpretation. This will increase the physician adoption of this automation by increasing the likelihood that the computer-generated result will be accepted with little or no adjustment, or that physician productivity and usability of the interpretation system is enhanced over time with increased use and learning. Further, future interpretation systems using this approach will require significantly reduced system pre-configuration. For example, the processing engine can also suggest that certain tools or image views be used, based on a comparison of the current user or users practices as compared to best practice user groups, or compared to clinically accepted practice guidelines. For example, a diagnostic review system such as within workstation 73 uses a viewer to display images incorporated into a physician interpretation workflow. The user uses the diagnostic review system to view and confirm findings. For example, the tracking module 78 or the diagnostic review system tracks whether the findings are unviewed, viewed, unconfirmed or confirmed, adjusted, unadjusted, deleted, added, reported or unreported. For example, the diagnostic review system allows the user to modify findings 77 in report 75 and these changes are reflected when the user (e.g., a physician) views images and findings using workstation 73. In both report 75 and workstation 73, the status of findings can be synchronized. For example, image processor 76 relies on some combination of the findings engine 77, tracking module 78 and adjustment engine 79 to produce derived images with or without the findings, overlays, contours, measurements or other indications included.

In one embodiment, user 81 can adjust thresholds and so if the first threshold the image processing engine picked as 2 and user 81 disagrees during the read and uses a tool perhaps a thresholding tool and selects 4, then the report that the reporting system completed can be updated to 4. The adjustment engine then knows that it should have used 4. The image processing engine can either a) determine through training (automatic or by an expert) that a new algorithm or filter is needed or b) simply set the threshold different in the viewer, when making the findings calculations, or producing derived images. The image(s) and other physician validated output can be pushed to the system of record, for example a VNA, PACS, ECM or EMR.

For example, key types can include adjusting thresholds, adjusting settings for parametric mapping, and specifically inputting a file (similar to the TeraRecon COF file, or a JSON structured object file, or similar in function) which allows all of the editing, contours and measurements made to a study to be recalled and the image volume restored to the point where user 81 left off. In this file, there are many forms of adjustable metadata possible which incorporate any digitally recorded object, edits, conversions, look up tables, vector files and other data that make up a processed medical image made of pixels or voxels.

In one embodiment, artificial intelligence finding system 70 can be used to determine a user and/or group preferred hanging protocol. A hanging Protocol is a standard way of viewing different images on a radiology interpretation system, called a PACS viewer. In the hanging protocol images on a computer screen are displayed in a certain order with multiple images on multiple monitors. For example, artificial intelligence finding system 70 receives feedback about how user 81 likes the images ordered, and begins to learn on its own which images go where. For example, the measurable difference between what one user believes is the right way, and the measured behavior of a group of users is used to make suggestions such as where the group engine's result is adapted to the individual's belief system and preferences. These systems (see GE patent for display protocols) use the DICOM image header information to determine the image type and then monitor use by the end user as to how they prefer image ordering. With the artificial intelligence system, one embodiment allows image processing engines that look within the images form landmarks to determine the image type without full regard to the DICOM image header. For example, any big measurable differences between how the individual is reading, versus the group belief can provoke changes and suggestions for that user which can be accepted or rejected as user preference settings, and that response is learned as a part of the individual's reading and tool preference protocols. In one embodiment, the artificial intelligence findings which represent possible preference settings are automatically evoked. In another embodiment, these possible preference settings are presented to the end user for confirmation to keep them in control of system behavior while providing prompting toward the best practices for their reading style and measured activity. Similarly, the image processing engines that are used to process images before, during and after the interpretation may be able to be adjusted, either a) in accordance to the individual user selected preferences or b) in accordance with data-provoked suggestions determined through machine learning and use of the data from the use or application of the tracking engine and adjustment engine to perform supervised or unsupervised training of these engines, as well as system prompts which can be accepted or rejected by the end-user.

The artificial intelligence finding can create a best in class or group belief system hanging protocol (i.e., layout of images and tools) and this is then compared to the individual belief system or changed layout. This can influence the statistical best practice or improvements which can be suggested.

In one embodiment, the artificial intelligence finding can have a red light, yellow light green light indicator to show in the patient list or in each image presentation panel that shows the status and overall output finding from engines, such as good, fair, bad, run or not run (i.e., within the image interpretation environment). It can be possible to have multiple indicators for an image or study. Multiple imaging studies can also be represented simultaneously in the viewer providing the physician the ability to review multiple studies in the viewer simultaneously. It can provide a quick look alert from the image processing engines producing findings. The level of finding or number of findings which represent each level can be adjusted and set by the author of the image processing engine, as a setting in the artificial intelligence system, or in the interpretation system. Any indicator can be used, for example, lights, letters, numbers, sounds, or any combination thereof.

The artificial intelligence finding system as described herein allows physicians to keep their eyes on a view viewer to review automatically generated findings, which correlate to the findings in the report. This provides a clean one-to-one relationship between the findings in the viewer and the findings in the report. Even if multiple different measurements in the viewer result in one finding of "moderate" it is still possible when the finding in the report is changed to provoke user 81 to validate the underlying findings. And, when any finding is adjusted that results in a change in the level, for example to severe, then the report is updated and user 81 is notified of that change being made. When the report is finalized, it can be stored with the resultant labelled images, along with a record of what was looked at and what was not, and which findings were validated by observation and which were not. This report can have the option to show all results, only selected results, no results, or only physician validated results from the system.

Figure 12:
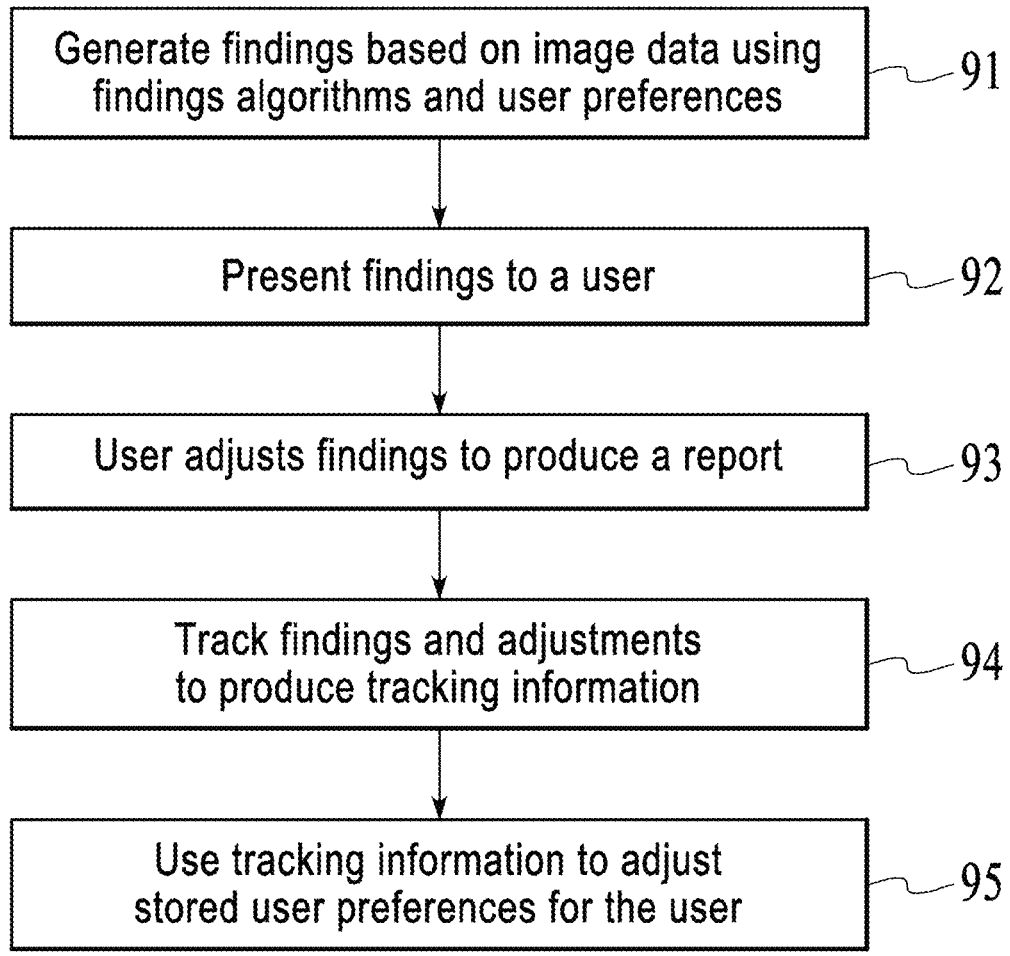
FIG. 12 is a simplified flowchart that illustrates logic flow within an artificial intelligence finding system in accordance with an embodiment.

FIG. 12 is a simplified flowchart that illustrates logic flow within an artificial intelligence finding system 70. In a block 91, findings engine 77 receives image data 71 and processes the image date to generate findings based on image data 71 and based on image interpretation algorithms that take into account stored preferences for user 81. For example, the stored preferences for a user can additionally be adjusted manually by the user, system administrators or other users of the medical image interpretation system. For example, the stored preferences can also be adjusted based on a machine learning engine that receives tracking information and based on the tracking information adjusts the stored preferences for the user. For example, the findings are abnormalities within medical images. For example, the finding may be a disease, a medically significant anatomic anomaly, a medically significant indication, a medically significant feature, a medically significant object, a medically significant shape, a medically significant texture, a medically significant measurement, a medically significant flag, a medically significant rendering, a medically significant contour, a medically significant defect in source image data, a medically significant similarity to reference images or data, a medically significant variance between measured activity and best/normal practice viewer use and/or interpretation workflow or some other finding of interest to the use in preparing report 75 or a medically significant defect in the provenance of the image processor engine 76 or the image data 71 used. For example, the image interpretation algorithms are based on studies that determine current best practices, common practices of users of the artificial findings system, clinical reference guidelines, group practice, are deterministic formulas, or some other criteria. Alternatively, or in addition, the findings are based at least partially on statistically derived information about practices of users of the artificial findings system or based on machine learned information about practices of users of the artificial findings system.

In a block 92, the findings are presented to user 81. For example, the findings are presented by a diagnostic review system composed of client viewer 74 and report 75. For example, the findings are presented to user 81 in data images that includes adjustments to image data 71 available from client viewer 74. For example, the adjustments to image data 71 can include contours that define an edge in 2D, 3D or 4D space within a medical image or a volume represented by many medical images, segmentations showing regions of interest of a medical image, image overlays or other information of interest to user 81 in preparing report 75, Alternatively, the findings are presented to user 81 in data images that includes adjustments to image data 71 available from client viewer 74 and in candidate findings within a prepopulated version of report 75. For example, the prepopulated report includes adjustments to the findings in the images in real-time. For example, adjustment to the candidate findings in the report result in adjusted measurements or the provocation of the physician to adjust the measurement and these are therefore reflected in adjustments to the image data. The adjustments include, for example, at least one of the following: an indication of contours that define an edge within a medical image or are a part of a measurement within an image; segmentations showing regions of interest of a medical image or within a volume of medical images, or uses the regions of interest as a starting point to define a clinical area of interest for a physician review, a measurement, or both a physician review and a measurement; image overlays showing color maps of varying opacity or transparency; derived images that use contours, segmentations and image overlays to produce a new source image data set; an image series that use contours, segmentations and image overlays to produce a new source image data set.

In a block 93, adjustment engine 79 allows user 81 to adjust the findings to produce a final version of report 75. Changes made to image data using client viewer 74 are reflected in report 75. Changes made within report 75 are reflected in changed made to the image data shown using client viewer 74.

In a block 94, tracking module 78 tracks findings and adjustments made to the findings by user 81 when producing the final version of report 75. The tracking module producing tracking information that reflects both changes made to report 75 and changes made to the image date within client viewer 74.

In a block 95, machine learning engine 82 receives the tracking information and based on the adjustments made to the findings by user 81 adjusts the stored preferences for user 81. For example, when the image interpretation algorithms are based at least partially on statistically derived or machine learned information about practices of users of the artificial findings system, the adjustments made to the findings by user 81 are included with the derived information about practices of users of the artificial findings system.

Figure 13:
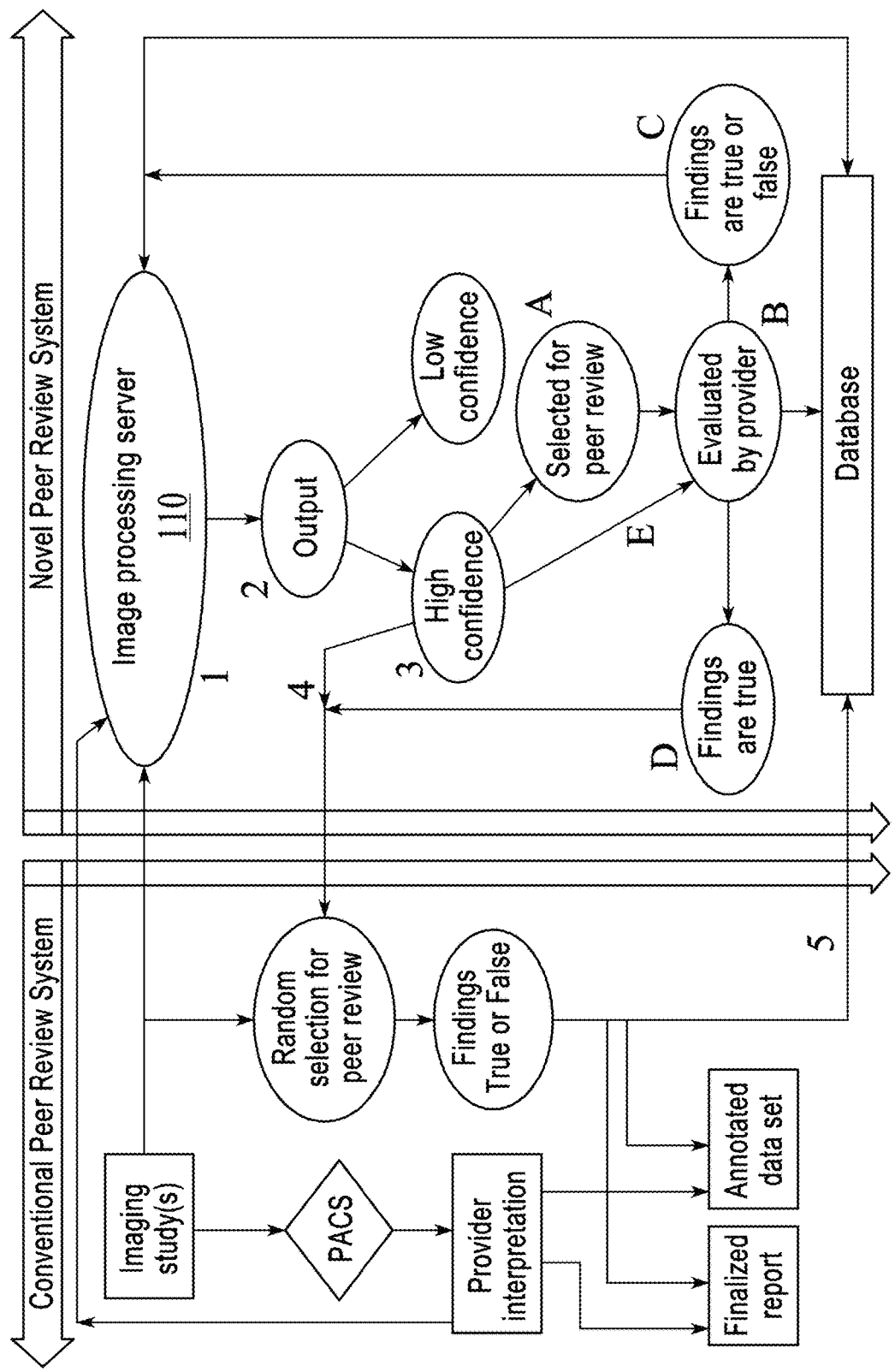
FIG. 13 is a flow diagram illustrating a workflow of a peer review process according to one embodiment.

Image processing server 110 can be incorporated into a peer review system as shown in FIG. 13. FIG. 13 shows a workflow loop diagram demonstrates examples of novel workflows of a peer review system according to one embodiment. Referring to FIG. 13, the workflow includes a peer review high confidence injection workflow loop. During this workflow loop, image processing server 110 is initiated by imaging studies or image studies and provider interpretation (also noted as a report) arriving at image processing server 110 notes as step 1. After a plurality and combination of engines process the image study, the output is noted as step 2. Studies or images with findings determined to have a high confidence of a potential finding or potential discrepancy with the provider interpretation are injected into the selection for peer review in Step 3. In step 4, this injected study is evaluated by a physician (who did not make the initial provider interpretation, if applicable). The results of that interpretation along with the peer review system interpretation are stored in the database as step 5 and can be used for future training of engines and engines of engines within image processing server 110 and the peer review system. In addition, in Step B, user interaction data is stored in the database as well.

The workflow further includes a peer review injected physician confirmed findings workflow loop. During this workflow loop, image processing server 110 is initiated by imaging studies or image studies and provider interpretation (also noted as a report) arriving at image processing server 110 notes as step 1. After a plurality and combination of engines process the image study, the output is noted as step 2. Studies or images with findings determined to have a high confidence of a potential finding or potential discrepancy with the provider interpretation are injected into the selection for peer review in Step 3. In step A, studies are selected via an engine of engines weighing the value of the high confidence findings and choosing a certain optimized number and type of studies (or images) for physician review. In Step B, the study is evaluated by a physician (who did not make the initial provider interpretation, if applicable). Positive results of that interpretation cause an automatic injection of the study into the peer review system in Step D, which does not occur if the physician finds the study to be negative. In both the positive or negative case, both the results of this interpretation (and any prior interpretations) as well as the peer review system interpretation are stored in the database as step C and can be used for future training of engines and engines of engines within image processing server 110 and the peer review system. In addition, in Step B, user interaction data is stored.

The workflow further includes a routine first read diagnostic interpretation with blinded peer review engine training workflow loop. During this workflow loop, image processing server 110 is initiated by imaging studies or image studies and provider interpretation (also noted as a report) arriving at image processing server 110 notes as step 1. After a plurality and combination of engines process the image study, the output is noted as step 2. Studies or images with findings determined to have a high confidence of a potential finding during the provider primary interpretation are calculated for comparison to the actual physician findings in Step E. In Step B, the study is evaluated by a physician (who did not make the initial provider interpretation, if applicable). In Step C, both the results of this interpretation (and any prior interpretations) as well as the peer review system interpretation are stored in the database and can be used for future training of engines and engines of engines within image processing server 110 and the peer review system. In addition, in Step B, user interaction data is stored.

For example, peer review by the peer review system is invoked in response to an initiation from natural language process system 310 or in response to generated findings based on the medical image data or user adjustments to the findings. For example, a pre-defined input and output schema for communications by and between findings engine 77 and the peer review system, and between findings engine 77 and other engines so as to allow for common methods of abstraction of inputs and outputs.

Figure 14:
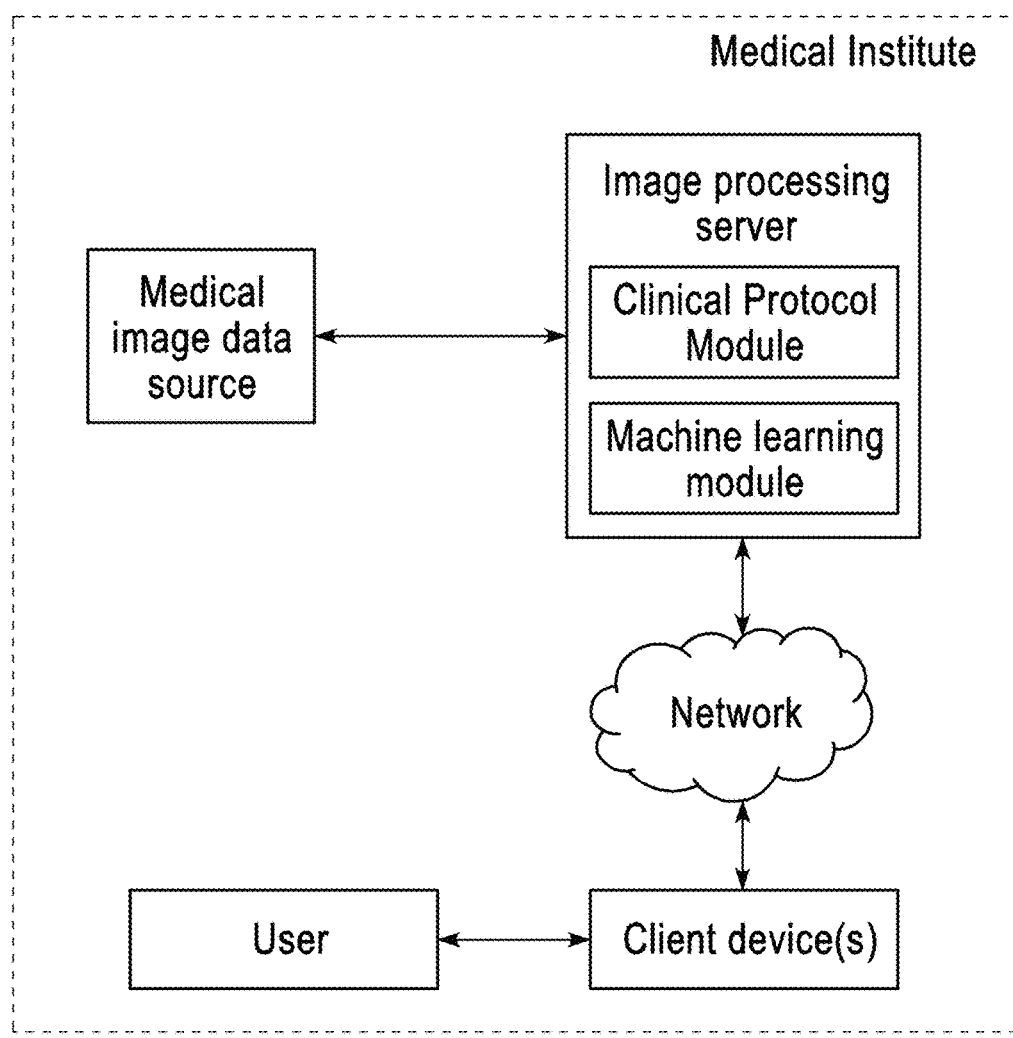
FIG. 14 is a block diagram illustrating a machine learned workflow system according to an embodiment.

FIG. 14 is a block diagram illustrating the machine learned workflow system according to one embodiment. Referring to FIG. 14, image processing server is configured to provide image data to a variety of clients, such as the client shown in FIG. 14. The image data is provided, for example, over a network (e.g., local area network (LAN), a metropolitan area network (MAN), a wide area network (WAN) such as the Internet or an intranet, or any combination thereof. Image processing server may be implemented using machine learning, artificial intelligence (AI) technology, deep learning, or any combination thereof. In one embodiment, image processing server performs several functions, including receiving information from a viewer or user, based on a user's input; collecting data from medical image data source and/or user inputs from clients; and integrating, processing, and transmitting the data received from the data sources such as medical image data source and client. In one embodiment, image processing server can perform an iterative machine learning process to learn/train based on user inputs.

A clinical protocol module can contain clinical protocols related to, for example, volumetric, CT Cardiac, CT Chest, CT Body, CT Head and Neck, MR Body, Body fusion, interventional radiology, maxilla facial, EVAR planning, TAVR planning, vessel analysis, Cardiac MR, Lung Segmentation, Liver Segmentation, Autobatch, any clinical protocols related to the medical areas described in this specification, or any combination thereof. Each clinical protocol can have one or more workflows (not shown). A workflow arranges activities into a process flow according to the order of performing each activity. Each of the activities in the workflow has a clear definition of its functions, the resource required in performing the activity, and the inputs received and outputs generated by the activity. Each activity in a workflow is referred to as a workflow stage, or a workflow element. Workflows can require specific image data to complete the workflows. Currently, users must select the specific image data to use in each workflow which is time consuming. Recommending image data for each workflow for the clinical protocol can reduce physician time. A workflow can include, but is not limited to, vessel analysis, calcium scoring, Time Dependent Analysis, CT/CTA subtraction, lobular decomposition, segmentation analysis and tracking, time volume analysis, flythrough, volumetric histogram, fusion CT/MR/PET/SPECT, multi-phase MR, parametric mapping, spherefinder, multi-kv, flow dynamic-MR, autobatch, ejection fraction, centerline extraction, straightened view, diameter and length measurements, CPR and axial renderings, V-Track mode for automated thin-slab MIP, measurement calculations, flow, perfusion, stress, rest, DE, and T1 mapping, any other workflow related to the medical areas described in this specification, any other workflows related to the clinical protocols described in this specification, or any combination thereof.

A machine learning module can receive image data from a medical image data source. The machine learning module can correlate image data from the medical image data source to a workflow based on in-image analysis and metadata. This workflow can be a unique machine learning module or a collection of machine learning (ensemble) which can provide a unique or a collection of results to be consume within a third-party application. The correlation of the medical data to a machine learning module or collection of machine learning can be done based on pattern extraction, feature extraction or image processing which result of a medical image classification (clusterization). Over time, the machine learning module can optimize and improve the association between the workflow and image data by machine learning based on a series of individual user's inputs, a group of user's inputs from one or more medical institutes over a network, information from the in-image analysis, information from metadata, or patient context or any combination thereof. The machine learning module can associate the series (i.e., image data) with the workflow based on metadata, for example within the DICOM file (e.g., DICOM headers and tags), such as patient ID, accession number, date, time frame, body part, body area, medical condition, encounter, procedure, symptom, description, or any combination thereof, or for example within the HL7 message containing clinical relevant information about the exam request (ORM, ORU etc. . . . ). The machine learning module can associate the series with the workflow based on in-image analysis, for example, by reconstructing the image or analyzing the pixel characteristics (e.g., intensity, shading, color, etc.) to determine the anatomy or modality. This correlation can be done based on organ (liver, kidney, heart, brain . . . ), body part (head, head and neck, chest, abdomen . . . ) or general feature extraction. For example, if the user opens the Time Volume Analysis (TVA) clinical protocol, an ejection fraction workflow can be included in the workflow table. The machine learning module can read image data from the series list and determine that based on the metadata and in-image analysis of the image data, a specific image data should be recommended to the user for the ejection fraction workflow. This correlation will be reinforce based on end-user feedback up to the point where the machine learning module will be able to automatically select the relevant data to be processed by other machine learning module or read using a particular clinical protocol. The user can remove the recommended image data and replace with another image data which will update the weight of the result and optimize machine learning module. Over time, through numerous iterations, the machine learning module can propose specific image data by machine learning based on, for example, the user's interactions and the information from the in-image analysis, metadata and patient clinical context or exam order.

For example, a machine learning module that is part of an artificial intelligence findings system includes an image identification engine that can extract features from a new medical image being analyzed to match this data to data present in the archive with the same characteristic (disease). Additionally, for example, the machine learning module can analyze data to extract a feature and prebuild a hanging protocol for a better viewing experience. Additionally, for example, the image identification engine within the machine learning module can analyze data to extract a feature and find similar data for the same patient to automatically present the data with its relevant prior information. For example, the similar data can pertain to anatomical structures such as body parts, anatomic anomalies and anatomical features. The similar data can also pertain to image type, and/or modality type, whether a same modality or a different modality.

In another embodiment, the machine learning module can receive image data. The machine learning module can process the image data and propose an applicable clinical protocol and/or workflow. The machine learning module can propose the clinical protocol and/or workflow based on metadata and/or in-image analysis of the image data. Over time, the machine learning module can optimize and improve the association between image data and the proposed workflow and/or clinical protocol by machine learning based on a series of individual user's inputs, a group of user's inputs from one or more medical institutes over a network, information from the in-image analysis, information from metadata, or any combination thereof. For example, the machine learning module can receive image data and determine that based on the metadata and in-image analysis of the image data, the perfusion workflow should be recommended to the user. The user can change the workflow associated with the image data from perfusion to flow. Over time, the machine learning module can learn based on, for example, the user's interactions and the information from the in-image analysis and metadata such that when a similar image data is loaded, the machine learning module can propose the flow workflow.

Image processing server can communicate over the network using a variety of communication protocols over a network that are compatible with the medical image data sources and patient information exchange (e.g., Laboratory Information System (LIS), Radiology Information System (RIS), Enterprise Content Management Systems (ECM), Electronic Medical Record (EMR), Hospital Information System (HIS), Picture Archiving and Communication System (PACS), VNA (Vendor Neutral Archive), EMR data, various directories as well as other data sources HIE (health information exchange) servers, or any combination thereof). However, more or fewer medical image data sources may be applied dependent upon the specific configuration and/or the medical data in demand. Medical image data sources may be managed and/or operated by different organizations or information providers than the organization which operates the image processing server.

In one embodiment, the medical data provided by data sources may include medical image data in a DICOM format, medical image data in a non-DICOM format, scheduling data, registration data, demographic data, prescription data, billing data, insurance data, dictation data, report data, workflow data, EKG data, best practices reference materials, reference materials, training materials, or any combination thereof. These data may reside in several locations or systems including HIS, RIS, PACS, LIS, ECM, EMR or other systems.

In one embodiment, the medical data provided by data sources may include medical image data in a DICOM format, medical image data in a non-DICOM format, scheduling data, registration data, demographic data, prescription data, billing data, insurance data, dictation data, report data, workflow data, EKG data, best practices reference materials, reference materials, training materials, or any combination thereof. These data may reside in several locations or systems including HIS, RIS, PACS, LIS, ECM, EMR or other systems.

The non-DICOM data may be in several formats including A/V, MPEG, WAV, JPG, PDF, Microsoft Office™ formats and other formats.

Since the various data sources (e.g., LIS, RIS, ECM, EMR, HIS, PACS, etc.) may use different communication standards, formats, or protocols, such as DICOM, HL7 (health level seven), XDS, HIE, ORU, etc., the machine learning module and other elements in this specification can use specific connectors or data source interfaces to access the data. Types of data connectors that can be used in the machine learned workflow system can include, but are not limited to, mobile, EMR plugin API (application programming interface), Web services, Web browser uploads/downloads, HL7, directory scanners, DLL (dynamic link library) APIs, XDS (cross-enterprise document sharing), VNA (vendor neutral archive), indexing servers, etc. In one embodiment, a router (not shown) can route data from the data source to the image processing server.

Clients may represent a variety of client devices such as a desktop, laptop, tablet, mobile phone, personal digital assistant (PDA), workstation, etc. Some clients may include a client application to access resources such as medical image processing tools or applications hosted by image processing server over a network. The viewer or client may have applications such as a thick client application or a thin client application, such as a web browser on a computer, a mobile device application on a mobile device, etc. The viewer may or may not require any software or plug-in download/installation. The viewer may have one or more viewer/viewing areas to display the data collected from the various data sources. The viewing areas may be in frames and/or tabs within a Web browser or application. The viewing areas may overlap, or be integrated with each other. The viewing areas may be within one another. The viewer can have more than one viewing area.

Figure 15:
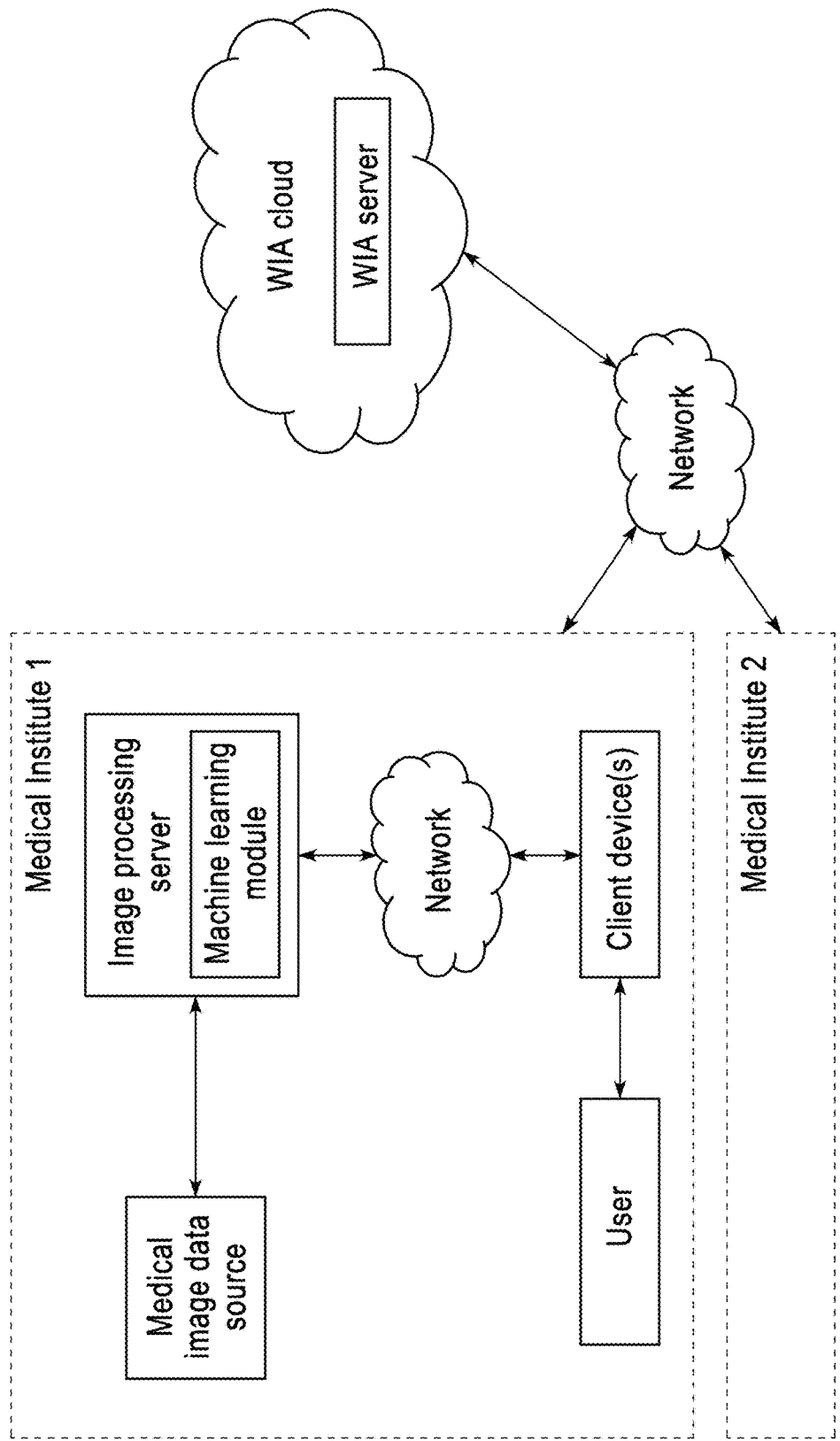
FIG. 15 is a block diagram illustrating a machine learned workflow system according to an embodiment

FIG. 15 is a block diagram illustrating the machine learned workflow system according to one embodiment. Referring to FIG. 15, there can be multiple medical institutes such that each machine learning module from each medical institute can be uploaded to a WIA server in a WIA cloud over a network. The WIA server can aggregate the machine learned data of multiple machine learning modules such that there can be a group machine learned workflow engine (not shown) that can have a high confidence level of correlating image data and workflows. Such a group machine learned workflow engine can be used by any medical institute via the WIA cloud. Each workflow engine (not shown) from each medical institute can be uploaded to the WIA server in the WIA cloud. The WIA server can aggregate each workflow engine to create a group workflow engine (not shown).

In one embodiment, a user's workflow engine (not shown) can be uploaded to the WIA server for other users to use. A group of users at a single medical institute can upload a workflow engine to the WIA server for other users to use. The WIA server can combine users and/or group workflow engines to optimize the confidence level for a specific workflow. The WIA cloud can combine users and/or group machine learned data to create an optimized workflow engine with a high level of confidence.

Figure 16:
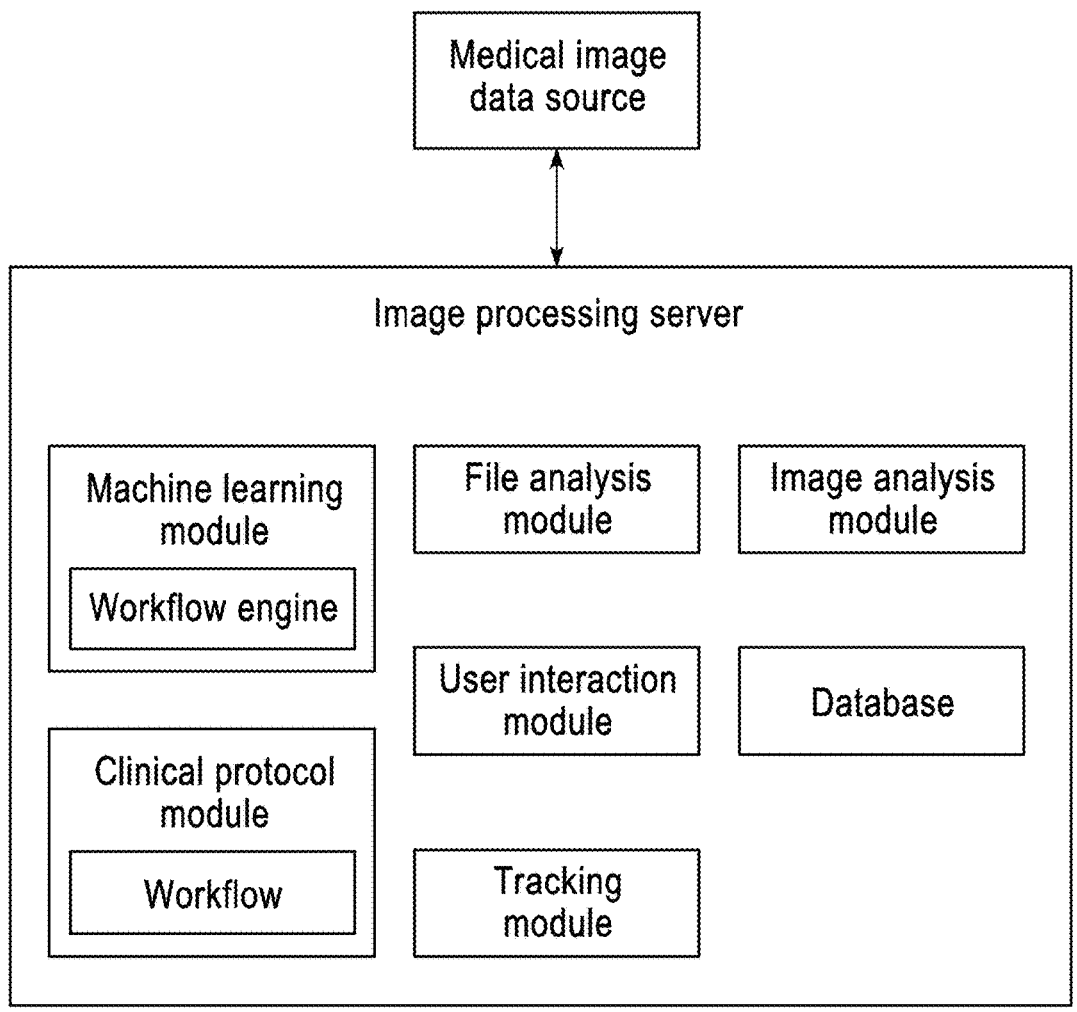
FIG. 16 is a block diagram illustrating a machine learned workflow system according to an embodiment.

FIG. 16 is a block diagram illustrating the Machine Learned Workflow System according to one embodiment. The image processing server can comprise of the machine learning module, the clinical protocol module, a file analysis module, a user interaction module, a tracking module, an image analysis module, a database, or any combination thereof. Any of the elements can be integrated within one another or further separated.

Database may be a data store to store medical data such as digital imaging and communications in medicine (DI-COM) compatible data, image data, files, or any combination thereof. Database may also incorporate encryption capabilities. Database may include multiple databases and/or may be maintained by a third-party vendor such as storage providers.

Database may be implemented with relational database management systems (RDBMS), e.g., Oracle™ database or Microsoft® SQL Server, etc.

The image processing server can receive image data. The image data can be received by the machine learning module. The image analysis module and the file analysis module can be integrated within the machine learning module or separate from the machine learning module, as shown in FIG. 16. When the image data is received by the machine learning module automatically or at the request of the client, the machine learning module can categorize the image data. The machine learning module can categorize the image data based on in-image analysis and/or metadata (e.g., DICOM headers or tags). The machine learning module can identify any image information from the image data such as the modality, orientation (e.g., axial, coronal, sagittal, off axis, short axis, 3 chamber view, or any combination thereof), anatomies (organs, vessels, bones, or any combination thereof), body section (e.g., head, next, chest, abdomen, pelvis, extremities, or any combination thereof), sorting information (e.g., 2D, 2.5D, 3D, 4D), study/series description, scanning protocol, sequences, options, flow data, or any combination thereof. Based on the image information from the image data, the machine learning module can recommend image data (i.e., series) for specific workflows. Based on the image information from the image data, the machine learning module can recommend workflows for specific image data.

The file analysis module can, for example, look at the DICOM header and determine the modality, orientation (e.g., axial, coronal, sagittal, off axis, short axis, or any combination thereof), anatomies (organs, vessels, bones, or any combination thereof), body section (e.g., head, next, chest, abdomen, pelvis, extremities, or any combination thereof), sorting information (e.g., 2D, 2.5D, 3D, 4D), study/series description, scanning protocol, sequences, options, or any combination thereof.

The image analysis module can perform an in-image analysis of image data. The in-image analysis can determine the body section, the orientation, anatomies, modality, sorting information, or any combination thereof. The image analysis module can use known methods of in-image analysis for medical image data such as time intensity changes, pixel intensities, reconstruction of image data to compare to known curves, convolutional neural network based on deep learning framework and naïve Bayes classifier, or any combination thereof. For example, the in-image analysis can reconstruct image data into smaller boxes with known coordinates, plot each coordinate on a graph, and compare it with a known graph to determine image information including, but not limited to, organs or modality.

Image information found in the metadata and/or from in-image analysis can be extracted for each image data and tracked by the tracking module. The tracking module can create a log file (not shown) that can include the image data, user interactions, image information, or any combination thereof. The tracking module can track and update the log file based on user interactions and/or changes in the image information.

The user interaction module can track the user's interactions with the client. User interactions can include, but are not limited to, user's preference for study layouts, states of image display, adjusting display protocols, image properties, preferences, work patterns, mouse selection, mouse movement, series move, image setting change, tool selection, tool settings, mouse mode, image navigation, image manipulation, series navigation, comparison study selection, navigation, zoom, layout, overlay data preferences, contour changes, any other movement or selection performed on the client, or any combination thereof. The user interaction module can send user interaction to the tracking module to be tracked and logged into the log file. The log file can be updated continuously or periodically. The log file can be stored in the database.

Figure 17:
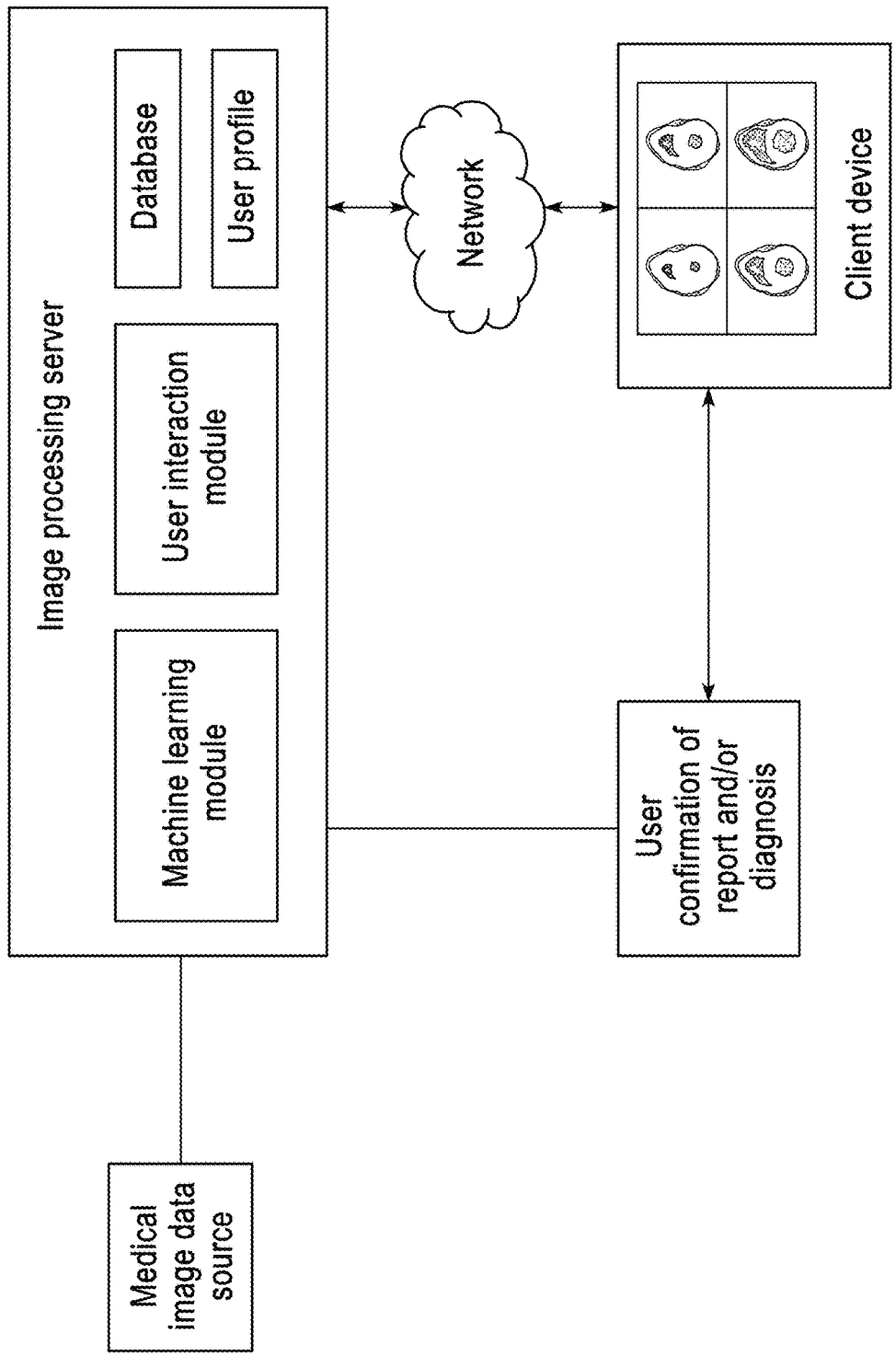
FIG. 17 is a block diagram illustrating a machine learned workflow system according to an embodiment.

User interactions can be assessed for usage patterns. FIG. 17 is a block diagram illustrating the Machine Learned Workflow System according to one embodiment. The image processing server can receive image data from the medical image data source. The image processing server (e.g., an engine (not shown) that is part of the image processing server) can analyze and send the image data to the client device to be displayed over a network (e.g., WAN or LAN). The display of the image data and application settings/preferences on the client can be a default preference based on the user's default preferences or the image processing server/client application's default preference. The user can manipulate the display preferences by user interactions, for example, by changing the study layout or tool preference. The user interaction module can track such user interactions. Such user interactions can be sent and tracked in the user profile. The machine learning module can assess the user interactions for usage patterns. The machine learning module can suggest to the user by sending a prompt to the client to automatically change the default preference based on the usage patterns of the user the next time image data is loaded and displayed on the client. If the user accepts the change based on the usage patterns, the user's user profile is updated such that the machine learning module can automatically update the default preference to include the usage patterns accepted by the user. In other words, if the user accepts the change based on the usage pattern, the user profile can be updated to reflect the updated user interaction, for example, workflow, display protocol, tool selection, or image setting. This embodiment can allow the system to track the user interactions and give the user the option to automate common steps and/or remove redundant steps in their study navigation.

Figure 18:
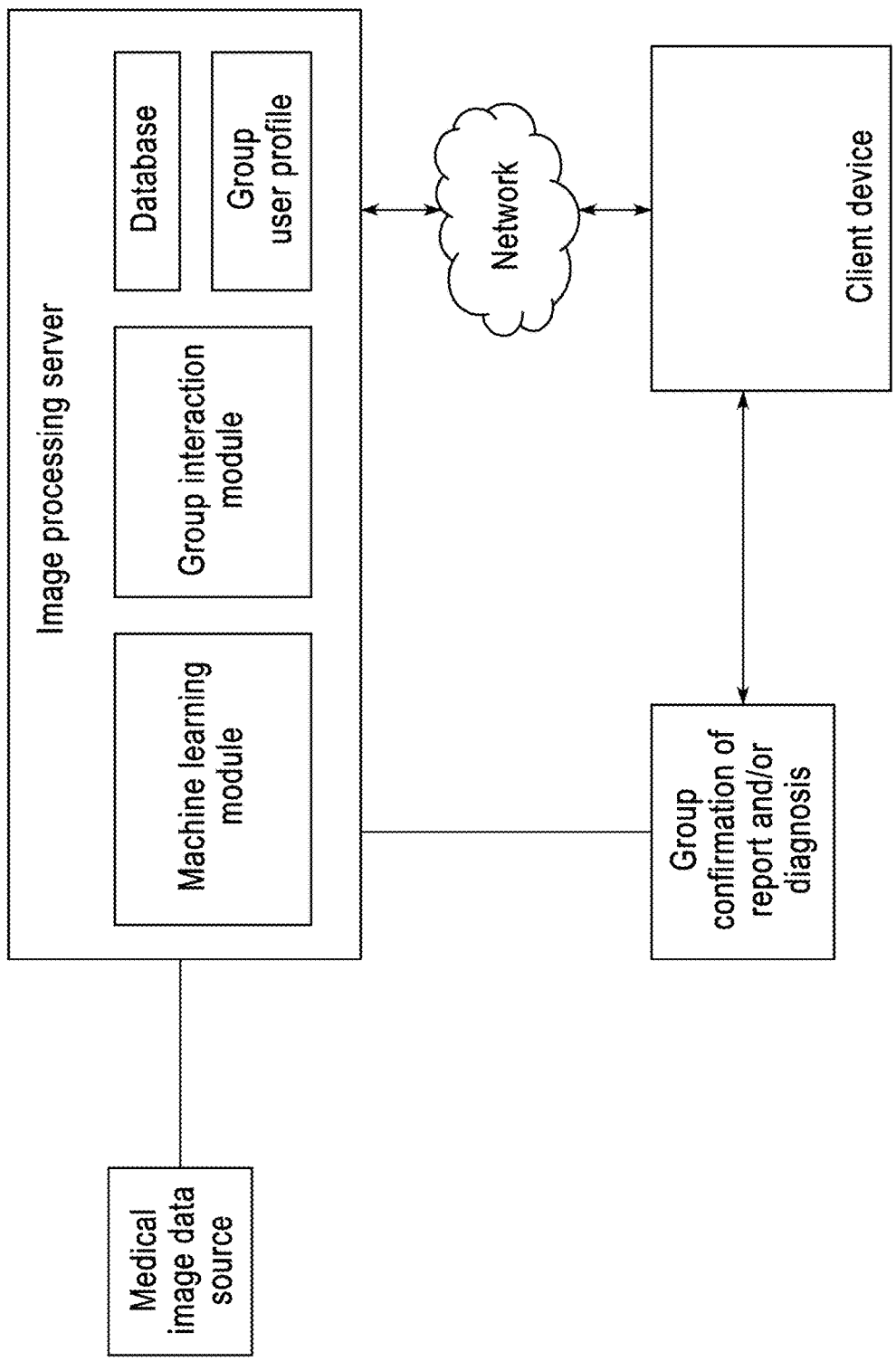
FIG. 18 is a block diagram illustrating a machine learned workflow system according to an embodiment.

FIG. 18 is a block diagram illustrating the Machine Learned Workflow System according to one embodiment. The Machine Learned Workflow System can be local or cloud-based for one or more medical institutes at one or more different locations. The image processing server can have a group interaction module and a group user profile such that usage patterns of a group (one or more users) can be tracked. The group user profile can be updated based on the group usage patterns. The machine learning module can automatically update the default preference to include the group usage patterns accepted by the group or governance body/best practice body. The group can be part of one medical institute, a combination of one or more medical institutes, or any combination thereof.

In another embodiment (not shown), the machine learning module can look for patterns of use consistent among users of the same group such as Radiologist to create a new default group user setting string. Such a default group user setting string can be assigned to any new members of the group. A user can reject the suggestion and keep their initial default preference and adjust such preferences manually.

For example, FIG. 19 illustrates a DICOM Header table to map MR series to functions such as Time Volume Analysis (TVA), Flow, DE, and Perfusion by the file analysis module according to one embodiment. The first column can be the label. The other columns can be the feature vector. In one embodiment, the file analysis module can break the strings in each column to words. The file analysis module can create a mapping function (e.g., Ax=B) such that the machine learning module can learn every time image data (e.g., a series) is loaded into the function. This process can be repeated until x converges for all of the label requirements. For example, in FIG. 19, A=[mr chest heart short_axis 4$d$ no mri cardiac cont flow quantross sax sorted]; Label, B='TVA'; and Mapping function, x, such that: Ax=B. Such a process is known as a Bayesian Inference. All of the image information and mapping functions can be tracked in the log file.

For example, a similar Bayesian approach can be performed by the image analysis module during in-image analysis. In one embodiment, the in-image analysis module can determine information such as anatomy or modality based on analysis of the image/image volume. Such image information can be extracted and processes in a similar function as described above. Such information can be included in the log file by the tracking module. The log file can be stored in the database and updated.

The in-image analysis module and the file analysis module can be run at the same time, different times, for specific image data series, pre-selected by the user, or any combination thereof.

Other machine learning approaches for in-image analysis and metadata can be implemented such as decision tree learning, association rule learning, artificial neural networks, deep learning, inductive logic programming, support vector machines, clustering, reinforcement learning, representation learning, similarity and metric learning, sparse dictionary learning, genetic algorithms, rule-based machine learning, learning classifiers systems, convolutional neural network based on deep learning framework and naïve Bayes classifier, or any combination thereof.

Figure 28:
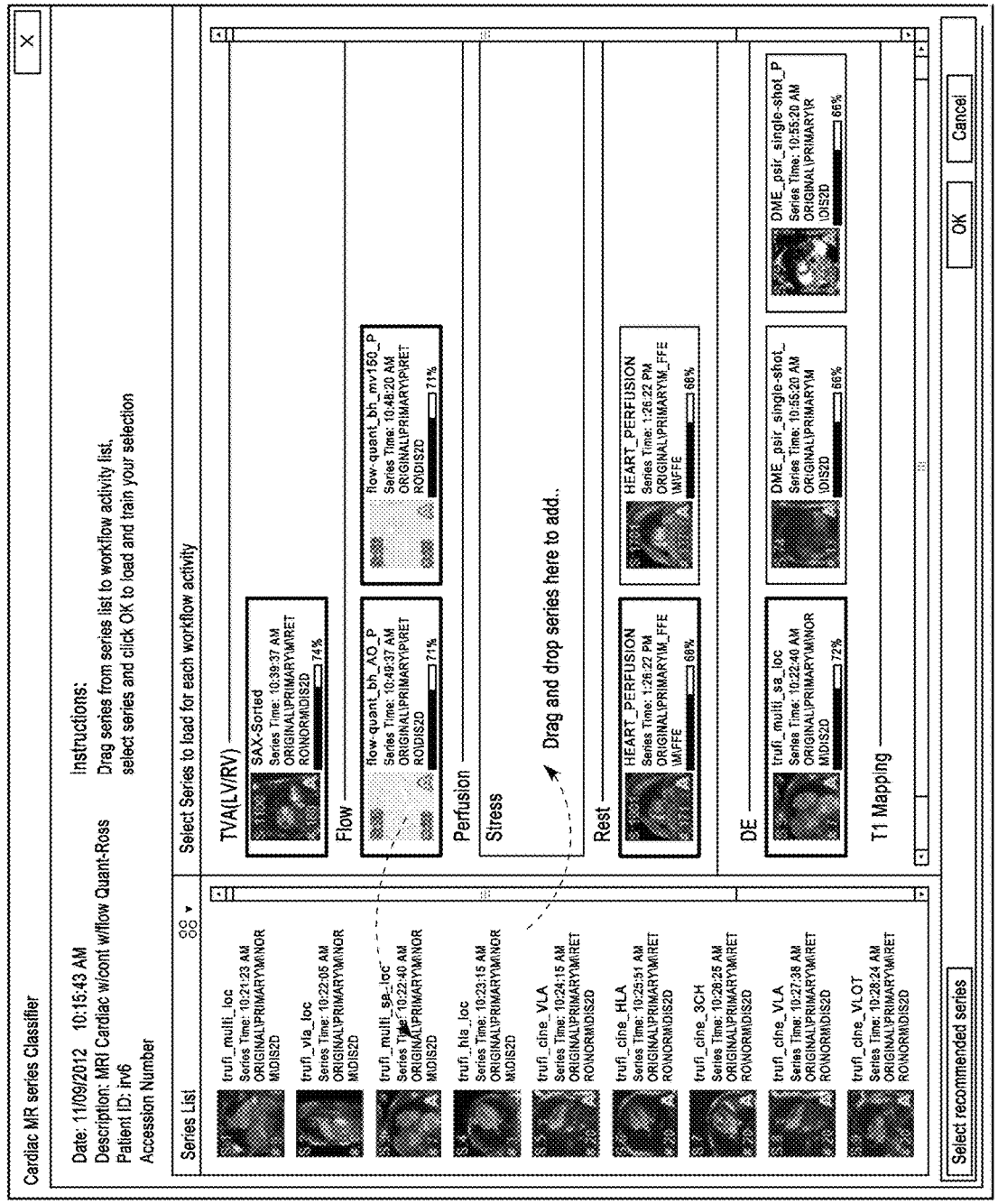

The clinical protocol module can contain clinical protocols. The workflow can arrange activities into a process flow according to the order of performing each activity. Each clinical protocol can have one or more workflows organized in a workflow table, as seen in FIG. 28.

In one embodiment, based on the image data (e.g., series volume) received by the machine learning module, the machine learning module, the file analysis module, and/or the image analysis module can propose a default clinical protocol. In one embodiment, based on the image data (e.g., series volume) received by the machine learning module, the machine learning module, the file analysis module, and/or the image analysis module can propose default workflows and recommend which image data can be included in each proposed workflow.

In one embodiment, the machine learning module can include proposed image data from a series list for each workflow based on user interactions, the image analysis module, and/or the file analysis module. The user can drag and drop the image data from the series list to the workflow in the workflow table if the user deems that the proposed image data for any workflow needs to be updated. The user interaction module can track the user's interaction of removing, replacing, or adding image data to the workflow. The user interaction module can send such information to the tracking module to update the log file. The machine learning module can train the workflow engine based on the user's interactions such that the next time image data is received by the machine learning module, the workflow engine can learn and suggest optimized proposed image data for the workflow. A similar technique can be used for suggesting workflows based on image data.

Figure 20:
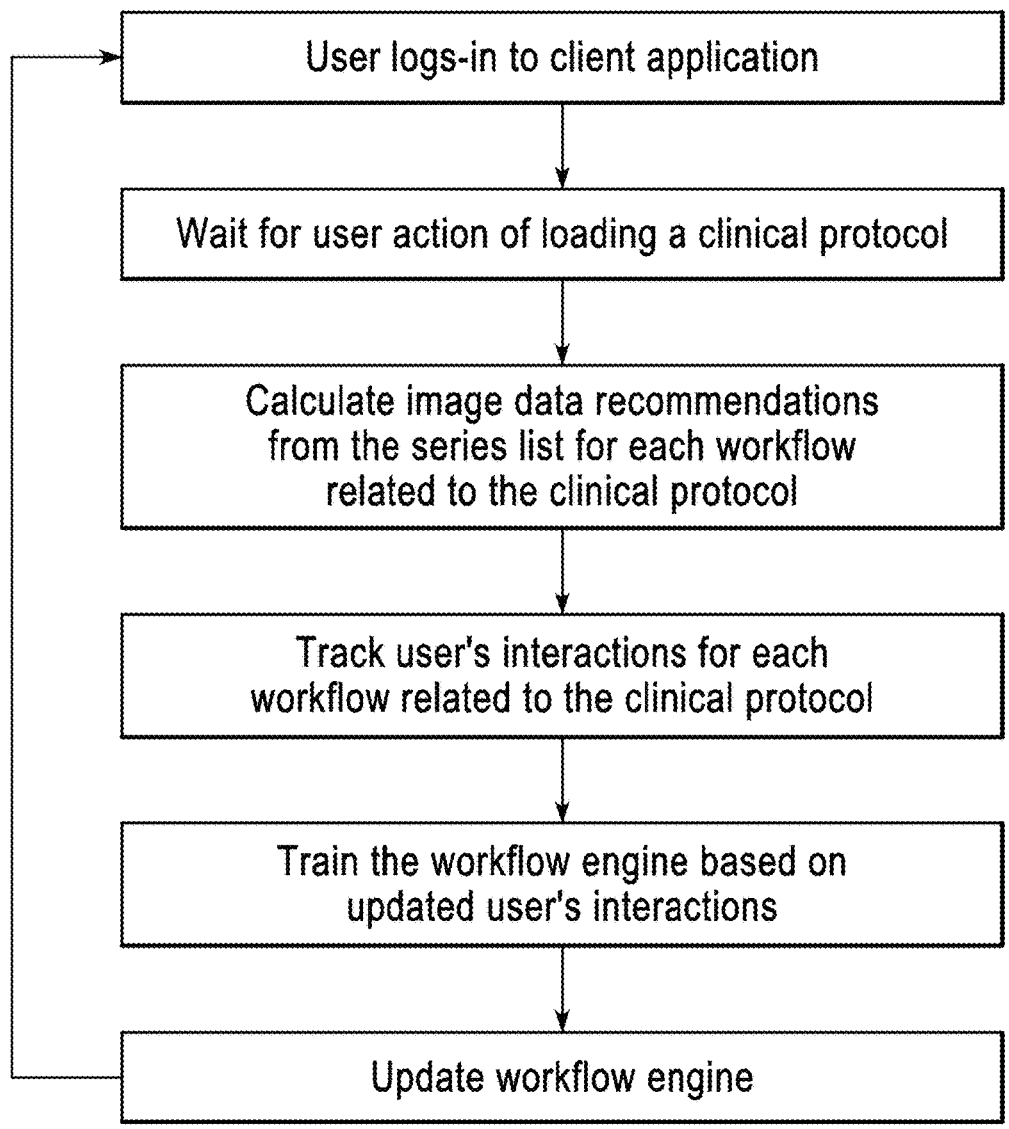
FIG. 20 is a process flow illustrating a machine learned workflow system according to an embodiment

FIG. 20 is a process flow illustrating the machine learned workflow system according to one embodiment. The user can log-in to the client. The server can wait for user action of loading the clinical protocol. Based on the selection of the clinical protocol, applicable workflows can be displayed. Based on the selection of the clinical protocol, the machine learning module and/or the workflow engine can calculate image data recommendations from the series list for each workflow related to the clinical protocol. The user interaction module can track user's interactions for each workflow related to the clinical protocol. The machine learning module can train the workflow engine based on updated user's interactions. The machine learning module can update the workflow engine based on updated user's interactions. Note that the tracking module can track the user interactions in the log file along with related image data, metadata, in-image analysis data, image information, or any combination thereof. Such log file can be used to train the workflow engine.

Figure 21:
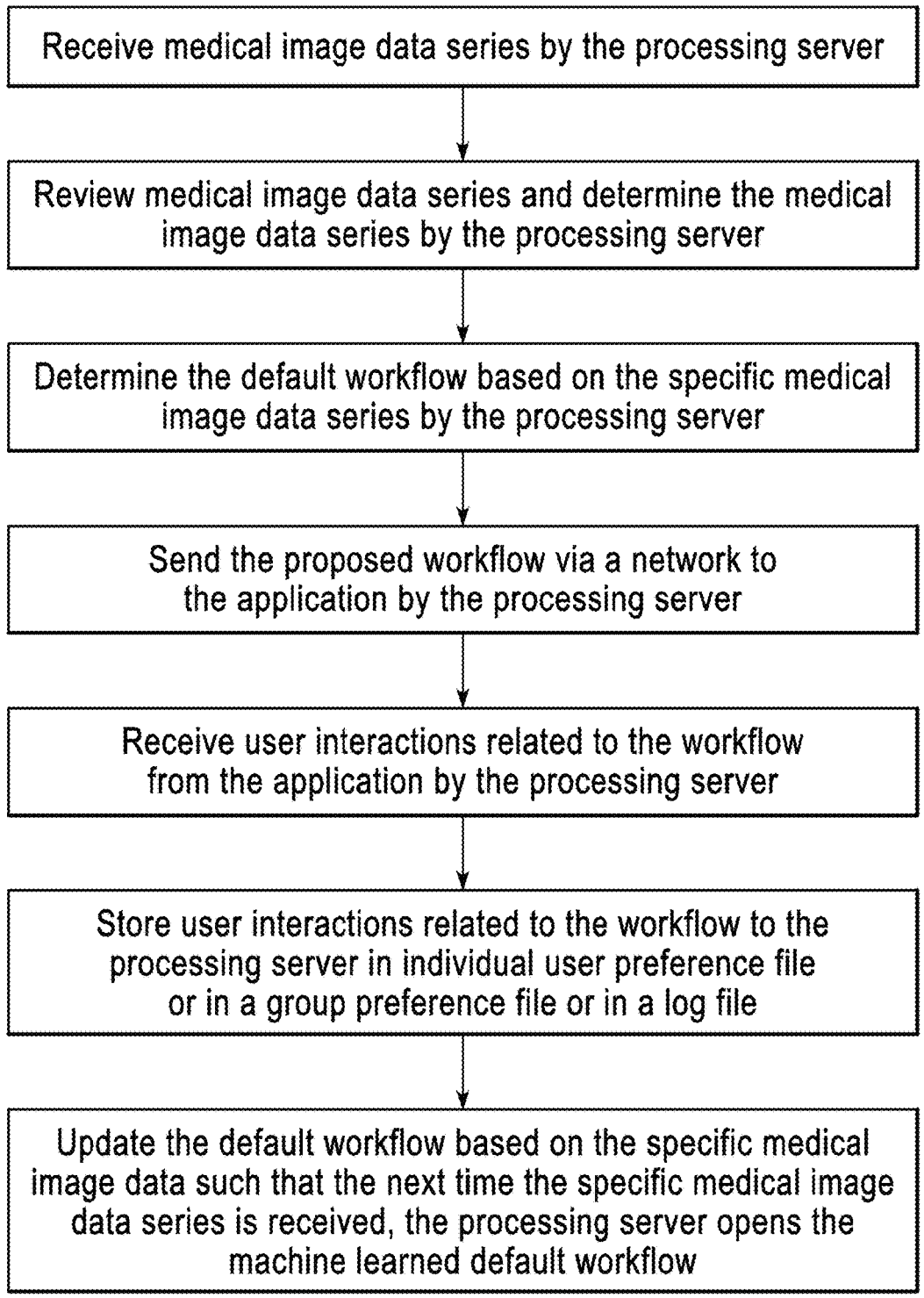
FIG. 21 is a process flow illustrating a machine learned workflow system according to an embodiment

For example, the user can log-in to the client. The server can wait for user action of loading a clinical protocol. The user can select Cardiac MR as the clinical protocol. Based on the selection of Cardiac MR, there can be workflows such as TVA, flow, perfusion, stress, rest, DE, T2 mapping, and T1 mapping. Each workflow can have a related machine learning module (e.g., TVA machine learning module, flow machine learning module, etc.) and a workflow engine (e.g., TVA workflow engine, flow workflow engine, etc.). The TVA workflow engine can calculate image data recommendations (by in-image analysis, metadata, user interactions, etc.) from the series list for the TVA workflow. The user can validate the recommended image data for each workflow, or the user can remove, add, or replace the recommended images data by dragging and dropping image data from the series list/workflow to the workflow/series list. The user interaction module can track user interactions for each workflow related to the clinical protocol (e.g., the user interaction module can keep track of the user removing a recommended image data from TVA workflow and replacing with another image data from the series list). Over time, through such an iterative process, the TVA machine learning module can train the TVA workflow engine based on the updated user interactions (i.e., the workflow engine can recommend image data multiple times and the user can correct the recommended image data each time so that such user interactions are logged into the log file and used to train the workflow engine). The machine learning module can update the TVA workflow engine based on the updated user's interactions such that the next time the user selects Cardiac MR as the clinical protocol, the TVA workflow engine can calculate optimized image data recommendations for the user. Note that the user can be an individual, a group of individuals, or multiple medical institutes. FIG. 21 is a process flow illustrating the machine learned workflow system according to one embodiment. The processing server can receive medical image data. The processing server can review medical image data and determine the category of the medical image data. The processing server can determine the default workflow based on the specific medical image data. For example, the processing server can review image data and determine that the medical image data belongs to the perfusion workflow because based on the metadata and the in-image analysis, all of the criteria for perfusion were met. The processing server can send the proposed workflow via a network to the client application. The processing server can receive user interactions related to the workflow from client application by the Processing Server. The processing server can store user interactions related to the workflow in individual user preference file or in a group preference file or in a log file. The processing server can update the default workflow based on the specific medical image data such that the next time the specific medical image data series or similar medical image data series are received, the processing server opens the machine learned default workflow.

Figures 22, 23, 24:
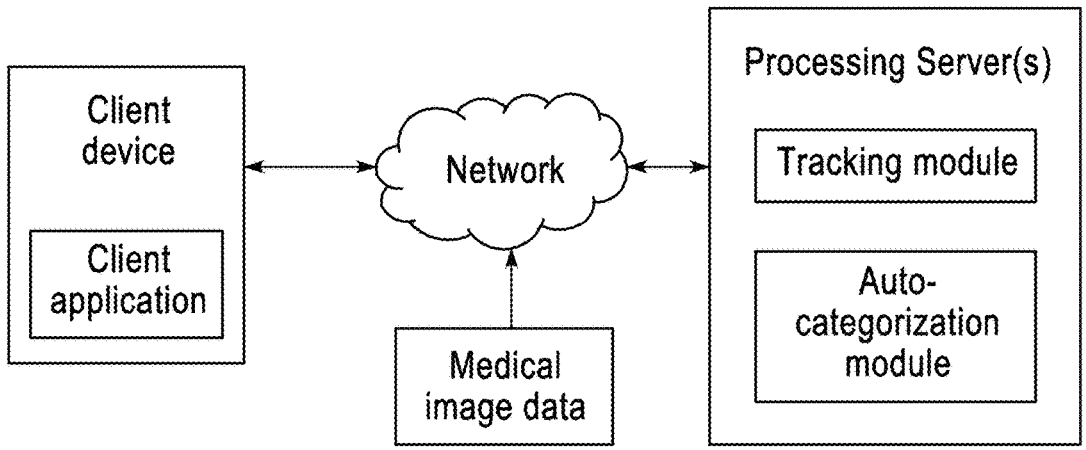
FIG. 22 is a block diagram illustrating a machine learned workflow system according to an embodiment.
FIG. 23, FIG. 24 and FIG. 25 illustrate a tracking module can track images based on tables of categories.

FIG. 22 is a block diagram illustrating the machine learned workflow system according to one embodiment. The client application can auto-categorize images via an auto-categorization module of the processing server. The medical image data can be sent via a network to the Processing Server where the auto-categorization module can categorize each of the images sent to the processing server. The processing server can perform preprocessing steps, for example, to the medical image data in order to prepare the image for viewing on the client application. For example, the processing server can convert raw image data into a DICOM Standard format, attach a DICOM Header, insert landmarks within the image, determine the modality, determine the anatomy, perform modality-specific enhancements (e.g., contrast or frequency compensation functions), or any combination thereof.

The auto-categorization module can categorize the images based on rules, training based on user, machine learning, DICOM Headers, in-image analysis, analysis of pixel attributes, landmarks within the images, characterization methods, statistical methods, or any combination thereof. The tracking module can track the images based on categories, for example, modality, orientation (e.g., axial, coronal, sagittal, off axis, short axis, 3 chamber view, or any combination thereof), anatomies (organs, vessels, bones, or any combination thereof), body section (e.g., head, next, chest, abdomen, pelvis, extremities, or any combination thereof), sorting information (e.g., 2D, 2.5D, 3D, 4D), study/series description, scanning protocol, sequences, options, flow data, or any combination thereof.

In one embodiment, the tracking module can track the images based on modality, as shown in FIG. 23. In one embodiment, the tracking module can track the images based on anatomical structures such as a body part, as shown in FIG. 24. FIG. 23 and FIG. 24 illustrate that the tracking module can track the images based on tables of categories.

In one embodiment, the machine learned workflow system can perform traceability recording in workflow engine over time (i.e., through iteration, the workflow engine can be optimized). Cloud based preprocessing engine can be optimized by the machine learned workflow system.

Figure 25:
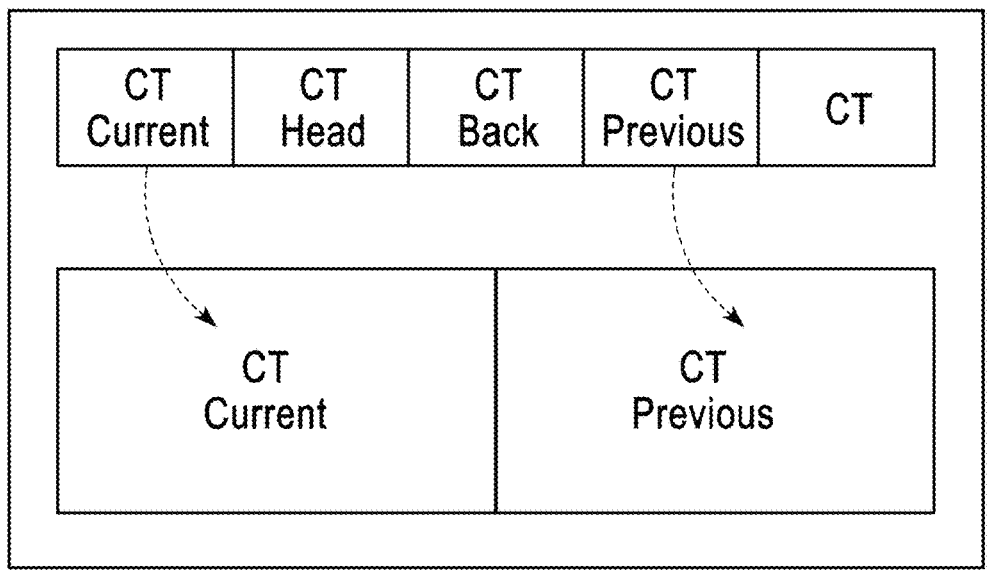
Figure 26:
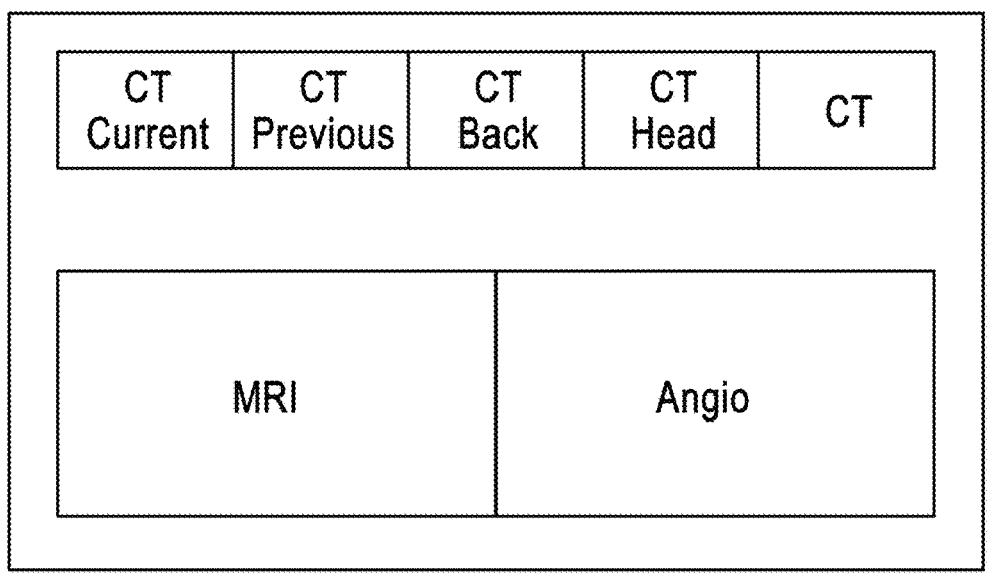

FIG. 25 and FIG. 26 are graphical user interfaces (GUI) illustrating a workflow where the user can drag images from a display ribbon at the top of the template to a viewing area according to one embodiment. The display ribbon can display the images based on categories. The user can select the category that the user would like to view the images in the ribbon. The display ribbon can then automatically display such chosen image categories. The user interactions can also be tracked by the auto-categorization module such that the Processing Server can learn the user preferences. For example, if a first user selects viewing CT Scans, the Processing Server can track such interactions. The processing server can display in the display ribbon in the client application the CT Scans the next time the user opens the template, as shown in FIG. 25. For example, if the first user drags the current CT Scan and the previous CT scan in the viewing window of the client application, the Processing Server can track such user interactions. The processing server can display in the viewing window the current CT Scan and the previous CT Scan the next time the user opens the template, as shown in FIG. 25. The system can learn based on a series of user interactions (i.e., iterative).

A graphical user interfaces can allow a user to drag, for example, tools in a certain order preferred by the user according to one embodiment. The tools can be displayed in a default preference. The user can drag the tools in a preferred order. The processing server can track the user interactions and include the user interactions in a user profile. The processing server can track usage patterns based on user interactions. The processing server can prompt the user to change the default preferences of the tools (e.g., in the order of tool 2, tool 1, tool 3, tool 5, tool 4) based on the usage patterns. If the user accepts the change, the next time the application is opened, the default preferences of the tools can be updated to include the change.

A user may prefer viewing all CT image data on the ribbon and other modalities in the viewing area, as shown in FIG. 26. The user can drag and drop images based on preference to/from the ribbon. The processing server can track the user preferences over time and optimize the presentation of the display by machine learning.

Figure 27:
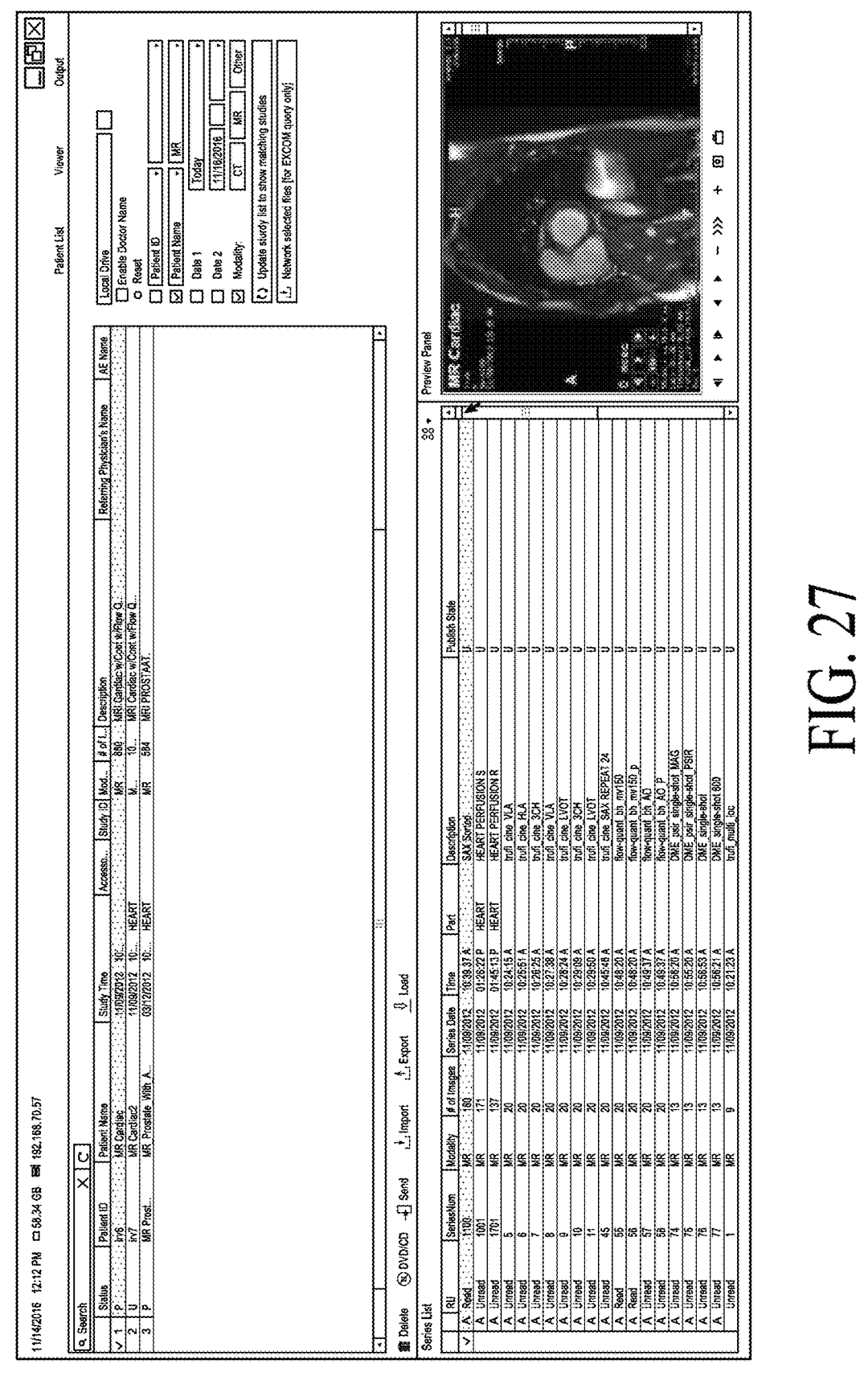

FIG. 27 is a graphical user interface (GUI) illustrating a workflow where the image process server has read the image data according to one embodiment.

FIG. 28 is a graphical user interface (GUI) illustrating a workflow where the image processing server has read the image data and assigned the image data to a specific workflow. The GUI can include a series list that comprises image data from a patient. The GUI can have a workflow table. The workflow table can have workflows. The workflows can have image data. The image data associated with the workflow can have a confidence level between about 0% to 100% or rating. The GUI can include a button that states "Select Recommended Series" which can enable the processing server to review each of the image data in the series list and associate image data with each workflow in the workflow table. The GUI can enable the user to drag and drop to remove, add, or replace image data to any of the workflows in the workflow table. Such user interactions are tracked as described above.

The machine learned medical imaging workflow selection system leverages the user's (e.g., physician) expertise to train the workflow engine.

Figure 29:
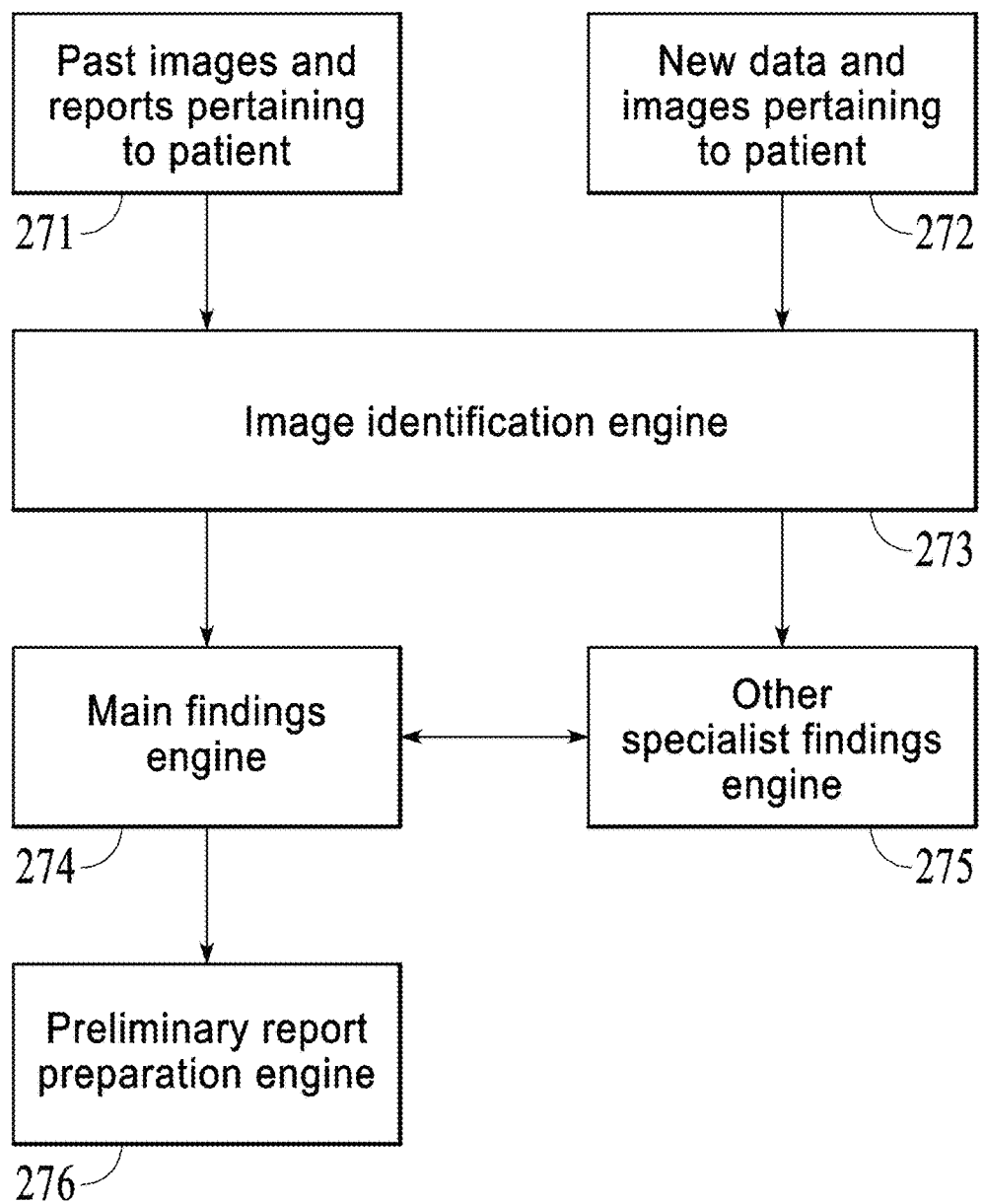
FIG. 29 is a simplified block diagram illustrates and arrangement of engines used in a medical image interpretation system.

FIG. 29 is a simplified block diagram illustrates and arrangement of engines used in a medical image interpretation system. An image identification engine 273 receives new image data 272 pertaining to a patient and past image data and reports 277 pertaining to the patient. Image identification engine 273 uses past image data and reports 277 to identify for study images of patient organs, body parts, and features within new image data 272.

For example, this allows one or multiple engines to use to one or more medical imaging studies of a patient to identify the anatomical structures, anatomical anomalies and anatomical features identified for study from a look at the image data and not the DICOM header information, or in addition to the DICOM header data. This allows successful operation if the DICOM header information for image data is wrong. This is an improvement over other systems such that only looks at the DICOM header and the user preference for how to display the images on a PACS.

A main findings engine 274 receives new image data 272 and processes new image data 272 to generate findings based on new image data 272 and based on the identified for study images of patient anatomical structures, anatomical anomalies and anatomical features within new image data 272.

For example, image identification engine 273, based on the new image data 272 and based on the identified for study images of patient anatomical structures, anatomical anomalies and anatomical features within the new image data, calls additional finding engines 275 to produce findings. Additional findings engines 275 are selected to be called by image identification engine 273 is based on the identified for study images of patient organs, body parts, and features within the new image data 272 and based upon the expertise of each of the additional findings engine 275. This allows an engine or engine of engines to process one or more medical imaging studies of a patient to determine the organs, body parts or even features found in the body parts or organs and even classifiers of these features, and uses this information to select pertinent other engines that can be run on all of these, and combinations of the images to provide precision-application of engines to image data.

For example, a tracking module that tracks findings and adjustments made to the findings by the user when using the diagnostic review system. The tracking module, as described above, produces tracking information based on the findings and adjustments made to the findings by the user and usage patterns ascertainable based on other users. A machine learning engine, such as described above, receives the tracking information and based on the tracking information adjusts categorization preferences that are used by the image identification engine when identifying study images for patients.

For example, this allows many imaging studies that include many image acquisitions, many image series, and the use of manual end-user interaction to select and categorize these series prior to evoking image post-processing workflows. An engine of engines driven with the above types of intelligence and awareness about body parts, organs, anatomic segmentation and features of these, can be used to automatically perform this categorization. For example, the end user can refine the categorizations before or after such artificial intelligence work, and then the artificial intelligence engine will learn to perform these tasks better from that input. Eventually, it becomes totally automatic.

The embodiments described above can be applied to a variety of medical areas. The machine learned workflow system can automatically load image data to specific workflows in the areas listed below. The machine learned workflow system can review image data and determine the workflow based on the image data in the areas listed below.

For example, the techniques described above can be applied to vessel analysis (including Endovascular Aortic Repair (EVAR) and electrophysiology (EP) planning). Such vessel analysis is performed for interpretation of both coronary and general vessel analysis such as carotid and renal arteries, in addition to aortic endograft and electro-physiology planning.

In addition, the techniques described above can be utilized in the area of endovascular aortic repair and measurements for endograft sizing. Multiple centerlines can be extracted to allow for planning of EVAR procedures with multiple access points. Diameters perpendicular to the vessel may be measured along with distances along the two aorto-iliac paths. Custom workflow templates may be used to enable the major aortic endograft manufactures' measurement specifications to be made as required for stent sizing.

Sac segmentation and volume determination with a "clockface" overlay to aid with documenting the orientation and location of branch vessels for fenestrated and branch device planning, may also be used.

The techniques described above can also be applied in the left atrium analysis mode. Measurements are automatically detected and captured into the integrated reporting system. These capabilities can be combined with other vessel analysis tools to provide a comprehensive and customized EP planning workflow for ablation and lead approach planning.

The techniques described above can also be utilized in calcium scoring. Semi-automated identification of coronary calcium is supported with Agatston, volume and mineral mass algorithms being totaled and reported on-screen. Results may be stored in an open-format database along with various other data relating to the patient and their cardiovascular history and risk factors.

The techniques described above can also be utilized in a time-volume analysis (TVA), which may include fully-automated calculation of left ventricular volume, ejection fraction, myocardial volume (mass) and wall thickening from multi-phasic data.

The techniques described above can also be utilized in the area of segmentation analysis and tracking (SAT), which includes supports analysis and characterization of masses and structures in various scans, including pulmonary CT examinations.

The techniques described above can also be utilized in the area of fly through which may include features of automatic segmentation and centerline extraction of the colon, with editing tools available to redefine these centerlines if necessary.

The techniques described above can also be utilized in the area of time-dependent analysis (TDA), which provides assessment tools for analyzing the time-dependent behavior of appropriate computerized tomographic angiography (CTA) and/or MRI examinations, such as within cerebral perfusion studies. Features include support for loading multiple time-dependent series at the same time, and a procedural workflow for selecting input and output function and regions of interest. An integrated reporting tool is provided as well as the ability to export the blood flow, blood volume and transit time maps to DICOM. The tools may also be used with time-dependent MR acquisitions to calculate various time-dependent parameters. The techniques described above can also be utilized in the area of CTA-CT subtraction, which includes automatic registration of pre- and post-contrast images, followed by subtraction or dense-voxel masking technique which removes high-intensity structures (like bone and surgical clips) from the CTA scan without increasing noise, and leaving contrast-enhanced vascular structures intact.

The techniques described above can also be utilized in dental analysis, which provides a CPR tool which can be applied for review of dental CT scans, offering the ability to generate "panoramic" projections in various planes and of various thicknesses, and cross-sectional MPR views at set increments along the defined curve plane.

The techniques described above can also be utilized in the area of multi-phase MR (basic, e.g. breast, prostate MR). Certain MR examinations (for example, breast, prostateMR) involve a series of image acquisitions taken over a period of time, where certain image structures become enhanced over time relative to other structures. This module features the ability to subtract a pre-enhancement image from all post-enhancement images to emphasize visualization of enhancing structures (for example, vascular structures and other enhancing tissue).

The techniques described above can also be utilized in parametric mapping (e.g. for multi-phase Breast MR), in which the parametric mapping module pre-calculates overlay maps where each pixel in an image is color-coded depending on the time-dependent behavior of the pixel intensity. The techniques described above can also be utilized in the area of SphereFinder (e.g. sphericity filter for lung and colon). SphereFinder pre-processes datasets as soon as they are received and applies filters to detect sphere-like structures. This is often used with lung or colon CT scans to identify potential areas of interest. The techniques described can also be utilized in fusion for CT/MR/PET/SPECT. Any two CT, PET, MR or SPECT series, or any two-series combination can be overlaid with one assigned a semi-transparent color coding and the other shown in grayscale and volume rendering for anatomical reference.

The techniques described above can also be utilized in the area of Lobular Decomposition. Lobular Decomposition is an analysis and segmentation tool that is designed with anatomical structures in mind. For any structure or organ region which is intertwined with a tree-like structure (such as an arterial and/or venous tree), the Lobular Decomposition tool allows the user to select the volume of interest, as well as the trees related to it, and to partition the volume into lobes or territories which are most proximal to the tree or any specific sub-branch thereof. This generic and flexible tool has potential research applications in analysis of the liver, lung, heart and various other organs and pathological structures. The techniques described above can also be utilized in the area of Volumetric Histogram. Volumetric Histogram supports analysis of a given volume of interest based on partition of the constituent voxels into populations of different intensity or density ranges. This can be used, for example, to support research into disease processes such as cancer (where it is desirable to analyze the composition of tumors, in an attempt to understand the balance between active tumor, necrotic tissue, and edema), or emphysema (where the population of low-attenuation voxels in a lung CT examination may be a meaningful indicator of early disease).

The techniques described above can also be utilized in the area of Motion Analytics. Motion Analytics provides a powerful 2D representation of a 4D process, for more effective communication of findings when interactive 3D or 4D display is not available. Any dynamic volume acquisition, such as a beating heart, can be subjected to the Motion Analysis, to generate a color-coded "trail" of outlines of key boundaries, throughout the dynamic sequence, allowing a single 2D frame to capture and illustrate the motion, in a manner that can be readily reported in literature. The uniformity of the color pattern, or lack thereof, reflects the extent to which motion is harmonic, providing immediate visual feedback from a single image.

The techniques described above can also be utilized to support other areas such as Multi-KV, enhanced multi-modality, findings workflow, and iGENTLE available from TeraRecon. Multi-KV: Support for Dual Energy and Spectral Imaging provides support for established applications of dual energy or spectral imaging CT data, such as removal of bone or contrast, as well as toolkits to support research and investigation of new applications of such imaging techniques.

While the machine learned medical imaging workflow selection system can be used to optimize workflows, similar machine learning training by users or groups of users can be used to improve display protocols.

The processes or methods depicted in the preceding figures may be performed by processing logic that includes hardware (e.g. circuitry, dedicated logic, etc.), firmware, software (e.g., embodied on a non-transitory computer readable medium), or a combination of both. Although the processes or methods are described above in terms of some sequential operations, it should be appreciated that some of the operations described may be performed in a different order. Moreover, some operations may be performed in parallel rather than sequentially.

In the foregoing specification, embodiments have been described with reference to specific exemplary embodiments thereof. It will be evident that various modifications may be made thereto without departing from the broader spirit and scope as set forth in the following claims. The specification and drawings are, accordingly, to be regarded in an illustrative sense rather than a restrictive sense.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. An algorithm can rely on predetermined formulas and/or can use machine learned information.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The techniques shown in the figures can be implemented using code and data stored and executed on one or more electronic devices. Such electronic devices store and communicate (internally and/or with other electronic devices over a network) code and data using computer-readable media, such as non-transitory computer-readable storage media (e.g., magnetic disks; optical disks; random access memory; read only memory; flash memory devices; phase-change memory) and transitory computer-readable transmission media (e.g., electrical, optical, acoustical or other form of propagated signals—such as carrier waves, infrared signals, digital signals).

What is claimed is:

1. A medical image interpretation system, comprising:
    an artificial intelligence findings system that comprises:
        an image identification engine that receives new image data pertaining to a patient and past diagnostic reports and past image data pertaining to the patient, the image identification engine using the past image data pertaining to the patient to identify for study, images of patient anatomical structures, anatomical anomalies and anatomical features within the new image data, wherein the image identification engine compensates for incorrect header data accompanying the past image data by analyzing the past image data apart from or in addition to any of the accompanying header data when identifying the images for study, and
        a findings engine that receives new image data and processes the new image data to generate findings based on the new image data and based on the images of patient anatomical structures, anatomical anomalies and anatomical features within the new image data that are identified for study;
    a diagnostic review system that presents the findings to a user, the findings as presented comprising data that includes images; and,
    an adjustment engine that receives notifications of changes to findings made by the user when using the medical image interpretation system.

2. A medical image interpretation system as in claim 1, wherein the image identification engine, based on the new image data and based on the images of patient anatomical structures, anatomical anomalies and anatomical features within the new image data that are identified for study, calls additional finding engines to produce findings, the additional findings engines being selected to be called by the image identification engine is based on the images of patient anatomical structures, anatomical anomalies and anatomical features within the new image data that are identified for study.

3. A medical image interpretation system as in claim 1, additionally comprising:
    a tracking module that tracks findings and adjustments made to the findings by the user when using the diagnostic review system, the tracking module producing tracking information based on the findings and adjustments made to the findings by the user and usage patterns ascertainable based on other users; and
    a machine learning engine that receives the tracking information and based on the tracking information adjusts categorization preferences that are used by the image identification engine when identifying for study, the images of patient anatomical structures, anatomical anomalies and anatomical features within the new image data.

4. A medical image interpretation system as in claim 1, wherein the findings presented to the user by the diagnostic review system include past diagnostic reports and image data for the patient that are relevant comparison information to the images of patient anatomical structures, anatomical anomalies and anatomical features within the new image data that are identified for study.

5. A medical image interpretation system as in claim 1, wherein the image identification engine extracts features from the new image data to match image data in an archive that includes image data with similar characteristic features.

6. A medical image interpretation system as in claim 1:
    wherein the image identification engine extracts features from the new image data to match image data in an archive that includes image data with similar characteristic features; and,
    wherein the diagnostic review system builds a display protocol using the new image data and the images on a computer screen to display the new image data and image data from the archive displayed in an order with one or more images on one or more displays as determined by the display protocol.

7. A medical image interpretation system as in claim 1, wherein the artificial intelligence findings system additionally comprises:
a tracking module that tracks findings and adjustments made to the findings by the user when using the diagnostic review system, the tracking module producing tracking information based on the findings and adjustments made to the findings by the user and usage patterns ascertainable based on other users.

8. A medical image interpretation system as in claim 7, wherein the diagnostic review system includes:
a viewer that displays the images incorporated into a physician interpretation workflow adapting itself based upon the tracking information;
wherein the diagnostic review system allows the user to view and confirm findings, with the tracking engine tracking whether the findings are unviewed, viewed, added, deleted, adjusted, unconfirmed, confirmed, reported or unreported;
wherein the diagnostic review system allows the user to modify the images to produce derived images;
wherein changes made to a diagnostic report are reflected in the images displayed by the viewer; and,
wherein changes made to the images displayed by the viewer are reflected in the diagnostic report.

9. A medical image interpretation system as in claim 1, wherein the image identification engine utilizes a neural network based on a deep learning framework.

10. A method for producing a diagnostic report from medical image data, the method comprising:
receiving new image data pertaining to a patient and past diagnostic reports and past image data pertaining to the patient;
using an image identification engine to identify for study, images of patient anatomical structures, anatomical anomalies and anatomical features within the new image data based on the past image data pertaining to the patient, wherein the image identification engine compensates for incorrect header data accompanying the past image data by analyzing the past image data apart from or in addition to any of the accompanying header data when identifying the images for study;
using a findings engine to process the new image data to generate findings based on the new image data and based on the images of patient anatomical structures, anatomical anomalies and anatomical features within the new image data that are identified for study;
using a diagnostic review system to present the findings to a user, the findings as presented comprising data that includes images; and,
providing, to an adjustment engine, notifications of changes to findings made by the user when using the medical image interpretation system.

11. A method as in claim 10, wherein using an image identification engine includes calling additional finding engines to produce findings, the additional findings engines being selected to be called by the image identification engine based on the images of patient anatomical structures, anatomical anomalies and anatomical features within the new image data that are identified study and based upon the expertise of each of the additional findings engines.

12. A method as in claim 10, additionally comprising:
using a tracking module to track findings and adjustments made to the findings by the user when using the diagnostic review system, the tracking module producing tracking information based on the findings and adjustments made to the findings by the user and usage patterns ascertainable based on other users; and
using a machine learning engine to receive the tracking information and based on the tracking information adjusting categorization preferences that are used by the image identification engine when identifying images for study.

13. A method as in claim 10, wherein the findings presented to the user by the diagnostic review system include past diagnostic reports and image data for the patient that are relevant comparison information to the images of patient anatomical structures, anatomical anomalies and anatomical features within the new image data that are identified for study.

14. A method as in claim 10, wherein the image identification engine extracts features from the new image data to match image data in an archive that includes image data with similar characteristic features.

15. A method as in claim 10:
wherein the image identification engine extracts features from the new image data to match image data in an archive that includes image data with similar characteristic features; and,
wherein the diagnostic review system builds a display protocol using the new image data and the images on a computer screen to display the new image data and image data from the archive displayed in an order with one or more images on one or more displays as determined by the display protocol.

16. A method as in claim 10, additionally comprising:
using a tracking module to track findings and adjustments made to the findings by the user when using the diagnostic review system, including producing tracking information based on the findings and adjustments made to the findings by the user and usage patterns ascertainable based on other users.

17. A method as in claim 16, wherein the diagnostic review system includes:
a viewer that displays the images incorporated into a physician interpretation workflow that is adapting itself based upon the tracking information;
wherein the diagnostic review system allows the user to view and confirm findings, with the tracking engine tracking whether the findings are unviewed, viewed, added, deleted, adjusted, unconfirmed, confirmed, reported or unreported;
wherein the diagnostic review system allows the user to modify the images to produce derived images;
wherein changes made to the diagnostic report are reflected in the images displayed by the viewer; and,
wherein changes made to the images displayed by the viewer are reflected in the diagnostic report.

18. A method as in claim 10 wherein the image identification engine utilizes a neural network based on a deep learning framework to identify for study, the images of patient anatomical structures, anatomical anomalies and anatomical features within the new image data based on the past image data pertaining to the patient.

19. A method for training an artificial intelligence findings system, the method comprising:
receiving new image data pertaining to a patient and past diagnostic reports and past image data pertaining to the patient;
identifying for study, images of patient anatomical structures, anatomical anomalies and anatomical features within the new image data based on the past image data pertaining to the patient, including:

compensating for incorrect header data accompanying the past image data by analyzing the past image data apart from or in addition to any of the accompanying header data when identifying the images for study;

generating findings based on the new image data and based on the images of patient anatomical structures, anatomical anomalies and anatomical features within the new image data that are identified for study;

presenting the findings to a user, the findings as presented comprising data that includes images; and, tracking findings and adjustments made to the findings by the user to produce tracking information based on the findings and adjustments made to the findings by the user and usage patterns ascertainable based on other users; and receiving the tracking information and based on the tracking information adjusting preferences that are used when identifying for study, the images of patient anatomical structures, anatomical anomalies and anatomical features within the new image data.

20. A method as in claim 19 using a neural network based on a deep learning framework when identifying images for study.

\* \* \* \* \*